(12) United States Patent
Chang et al.

(10) Patent No.: US 7,462,175 B2
(45) Date of Patent: Dec. 9, 2008

(54) DEVICES, SYSTEMS AND METHODS FOR TREATING DISORDERS OF THE EAR, NOSE AND THROAT

(75) Inventors: John Y. Chang, Mountain View, CA (US); Joshua Makower, Los Altos, CA (US); Julia D. Vrany, Sunnyvale, CA (US); Theodore C. Lamson, Pleasanton, CA (US); Amrish Jayprakash Walke, Milpitas, CA (US)

(73) Assignee: Acclarent, Inc., Menlo Park, CA (US)

( * ) Notice: Subject to any disclaimer, the term of this patent is extended or adjusted under 35 U.S.C. 154(b) by 524 days.

(21) Appl. No.: 11/037,548

(22) Filed: Jan. 18, 2005

(65) Prior Publication Data
US 2006/0095066 A1    May 4, 2006

Related U.S. Application Data

(63) Continuation-in-part of application No. 10/829,917, filed on Apr. 21, 2004, and a continuation-in-part of application No. 10/912,578, filed on Aug. 4, 2004, now Pat. No. 7,361,168, and a continuation-in-part of application No. 10/944,270, filed on Sep. 17, 2004.

(51) Int. Cl.
*A61M 31/00* (2006.01)

(52) U.S. Cl. .................................................. 604/510

(58) Field of Classification Search ......... 604/509–510, 604/94.01, 103.1, 103.04, 103.05, 96.01, 604/164.01, 164.09, 164.1, 164.11, 164.13, 604/164.08, 171, 173, 101.02
See application file for complete search history.

(56) References Cited

U.S. PATENT DOCUMENTS 705,346 A    7/1902   Hamilton 2,525,183 A    10/1950   Robison (Continued)

OTHER PUBLICATIONS

Strohm et al. Die Behandlung von Stenosen der oberen Luftwege mittels rontgenologisch gesteuerter Balloondilation Sep. 25, 1999.*

(Continued)

*Primary Examiner*—Kevin C Sirmons
*Assistant Examiner*—Deanna K Hall
(74) *Attorney, Agent, or Firm*—Robert D. Buyan; Stout, Uxa, Buyan & Mullins, LLP

(57) ABSTRACT

Sinusitis, mucocysts, tumors, infections, hearing disorders, choanal atresia, fractures and other disorders of the paranasal sinuses, Eustachian tubes, Lachrymal ducts and other ear, nose, throat and mouth structures are diagnosed and/or treated using minimally invasive approaches and, in many cases, flexible catheters as opposed to instruments having rigid shafts. Various diagnostic procedures and devices are used to perform imaging studies, mucus flow studies, air/gas flow studies, anatomic dimension studies and endoscopic studies. Access and occluding devices may be used to facilitate insertion of working devices such asendoscopes, wires, probes, needles, catheters, balloon catheters, dilation catheters, dilators, balloons, tissue cutting or remodeling devices, suction or irrigation devices, imaging devices, sizing devices, biopsy devices, image-guided devices containing sensors or transmitters, electrosurgical devices, energy emitting devices, devices for injecting diagnostic or therapeutic agents, devices for implanting devices such as stents, substance eluting or delivering devices and implants, etc.

21 Claims, 44 Drawing Sheets

U.S. PATENT DOCUMENTS

| | | | |
|---|---|---|---|
| 3,800,788 A | 4/1974 | White | |
| 3,859,993 A | 1/1975 | Bitner | |
| 4,102,342 A | 7/1978 | Akiyama et al. | |
| 4,437,856 A | 3/1984 | Valli | |
| 4,811,743 A * | 3/1989 | Stevens | 600/585 |
| 5,021,043 A | 6/1991 | Becker et al. | |
| 5,169,386 A | 12/1992 | Becker et al. | |
| 5,207,695 A | 5/1993 | Trout, III | |
| 5,346,075 A | 9/1994 | Nichols et al. | |
| 5,578,048 A | 11/1996 | Pasqualucci | |
| 5,928,192 A | 7/1999 | Maahs | |
| 5,997,562 A | 12/1999 | Zadno-Azizi et al. | |
| 6,716,813 B2 | 4/2004 | Lim et al. | |
| 6,776,772 B1 * | 8/2004 | Vrijer et al. | 604/101.02 |
| D501,677 S | 2/2005 | Becker | |
| D534,216 S | 12/2006 | Makower et al. | D19/62 |
| 2003/0100886 A1 * | 5/2003 | Segal et al. | 604/509 |
| 2004/0064083 A1 | 4/2004 | Becker | |
| 2004/0064150 A1 * | 4/2004 | Becker | 606/196 |
| 2005/0240147 A1 | 10/2005 | Makower et al. | 604/96.01 |
| 2005/0245906 A1 | 11/2005 | Makower et al. | 604/891.1 |
| 2006/0004323 A1 | 1/2006 | Chang et al. | 604/28 |
| 2006/0106361 A1 | 5/2006 | Muni et al. | 604/500 |
| 2006/0210605 A1 | 9/2006 | Chang et al. | 424/434 |
| 2007/0073269 A1 | 3/2007 | Becker | |
| 2007/0129751 A1 | 6/2007 | Muni et al. | 606/196 |
| 2007/0135789 A1 | 6/2007 | Chang et al. | 604/500 |
| 2007/0208301 A1 | 9/2007 | Evard et al. | 604/103.1 |

OTHER PUBLICATIONS

Göttman, et al.; Balloon Dilation of Recurrent Ostial Occlusion of the frontal sinus; Abstract No. B-04353, European Congress of Radiology, Mar. 2001.
Göttman, et al., Balloon dilatation of recurrent ostial occlusion of the front sinus; ECR, Mar. 2, 2001.
Göttman, et al., Successful Treatment of Recurrent Post-operative Frontal Sinus Stenoses by Balloon Dilatation; Cirse, Oct. 5, 2002.
Göttman, et al., Balloon dilatation in the nasal cavity and paranasal sinuses; Cirse, Sep. 25, 2004.
Robison, J. Mathews, M.D., Pressure Treatment of Purulent Maxillary Sinusitis, Texas State Journal of Medicine, May 1951, pp. 281-288.
Robison, J. Mathews, M.D., Pressure Treatment of Maxillary Sinusitis, J.A.M.A., May 31, 1952, pp. 436-440.
Strohm et al. Die Behandlung von Stenosen der oberen Luftwege mittels röntgenologisch gesteuerter Ballondilation Sep. 25, 1999.
U.S. Appl. No. 11/544,009, filed Oct. 4, 2006, Muni et al.
U.S. Appl. No. 11/928,097, filed Oct. 30, 2007, Chang et al.
U.S. Appl. No. 11/789,704, filed Apr. 24, 2007, Goldfarb et al.
U.S. Appl. No. 11/648,159, filed Dec. 29, 2006, Morriss et al.
U.S. Appl. No. 11/527,773, filed Sep. 25, 2006, Makower et al.
Office Action dated Dec. 10, 2007 in U.S. Appl. No. 10/912,578.
Office Action dated Nov. 28, 2007 in U.S. Appl. No. 11/234,395.
International Search Report, PCT International Application No. PCT/US06/02004.
Lanza, Donald C., Postoperative Care and Avoiding Frontal Recess Stenosis, International Advanced Sinus Symposium, Jul. 21-24, 1993.

* cited by examiner

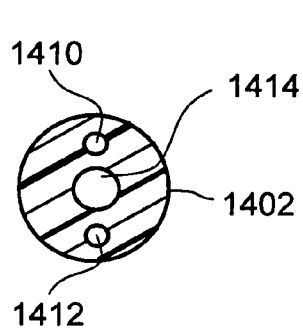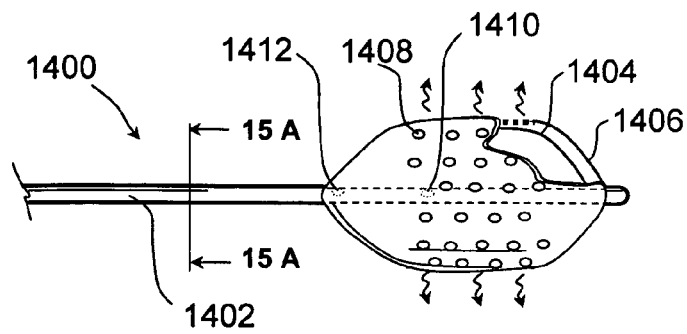
Fig. 15 A          Fig. 15
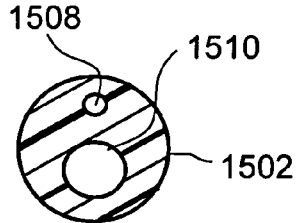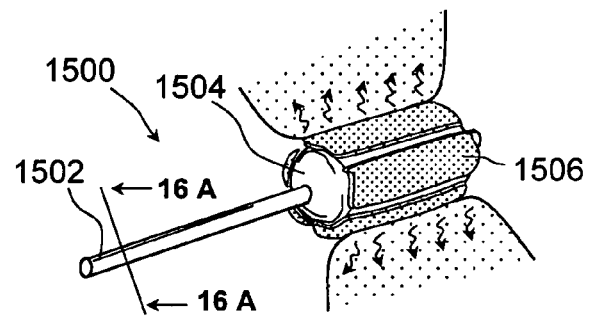
Fig. 16 A          Fig. 16
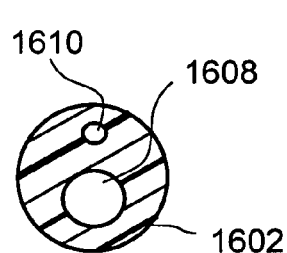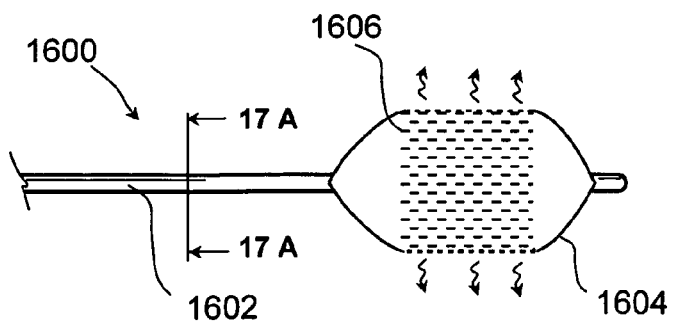
Fig. 17A          Fig. 17

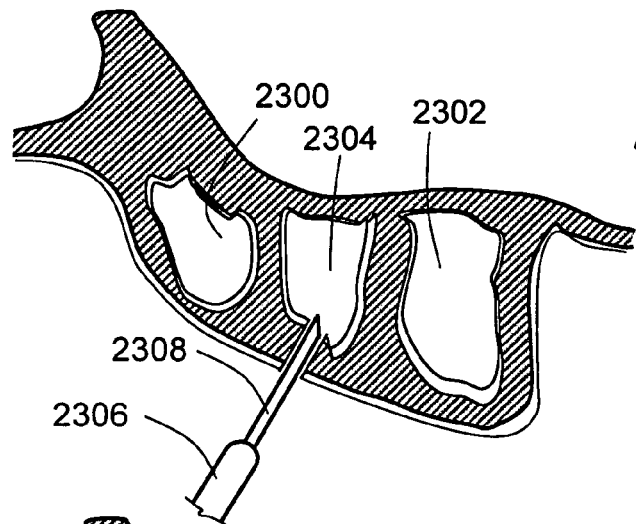
Fig. 24 A'
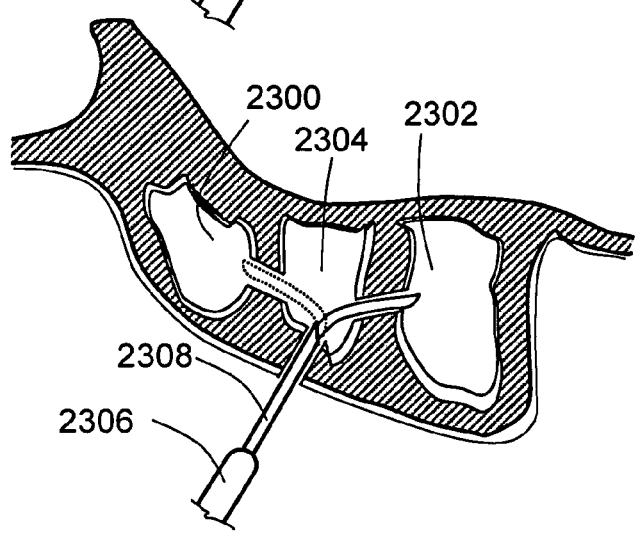
Fig. 24 A''
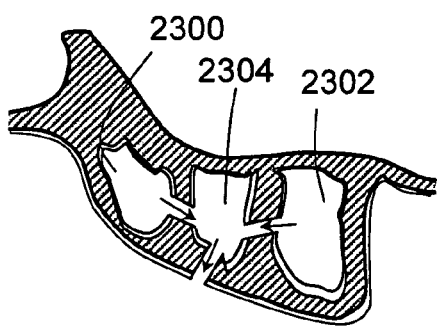
Fig. 24 A'''
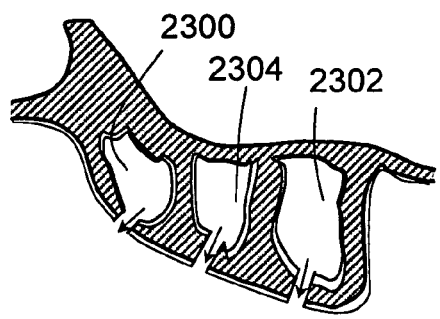
Fig. 24 A''''

DEVICES, SYSTEMS AND METHODS FOR TREATING DISORDERS OF THE EAR, NOSE AND THROAT

RELATED APPLICATION

This application is a continuation-in-part of 1) U.S. patent application Ser. No. 10/829,917 entitled "Devices, Systems and Methods for Diagnosing and Treating Sinusitis and Other Disorders of the Ears, Nose and/or Throat" filed on Apr. 21, 2004, 2) U.S. patent application Ser. No. 10/912,578 now U.S. Pat. No. 7,361,168 entitled "Implantable Device and Methods for Delivering Drugs and Other Substances to Treat Sinusitis and Other Disorders" filed on Aug. 4, 2004 and 3) U.S. patent application Ser. No. 10/944,270 entitled "Apparatus and Methods for Dilating and Modifying Ostia of Paranasal Sinuses and Other Intranasal or Paranasal Structures" filed on Sep. 17, 2004, the entireties of each such parent application being expressly incorporated herein by reference.

FIELD OF THE INVENTION

The present invention relates generally to medical devices, systems and methods and more particularly to minimally invasive devices, systems and methods for treating sinusitis and other ear, nose & throat disorders.

BACKGROUND OF THE INVENTION

Surgical treatments for sinusitis and other disorders of the ear, nose and throat have evolved slowly over the years. In current clinical practice, functional endoscopic sinus surgery (FESS) is often used to treat sinusitis or other disorders where drainage of mucous is impaired and/or chronic infections are present. In FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose. Other endoscopic intranasal procedures have been used to remove pituitary tumors, to treat Graves disease (i.e., a complication of hyperthyroidism which results in protrusion of the eyes) and surgical repair of rare conditions wherein cerebrospinal fluid leaks into the nose (i.e., cerebrospinal fluid rhinorrhea).

In some instances, sinus and ENT surgery has been performed with the assistance of electronic navigation devices (i.e., "image-guided FESS"). In such image guided surgical procedures, integrated anatomical information is supplied through CT-scan images or other anatomical mapping data taken before the operation. Data from a preoperative CT scan or other anatomical mapping procedure is downloaded into a computer and special sensors known as localizers are attached to the surgical instruments. Thus, using the computer, the surgeon can ascertain, in three dimensions, the precise position of each localizer-equipped surgical instrument at any given point in time. This information, coupled with the visual observations made through the standard endoscope, can help the surgeon to carefully position the surgical instruments to avoid creating CSF leaks and to avoid causing damage to nerves or other critical structures.

Although FESS continues to be the gold standard therapy for severe sinuses, it has several shortfalls. Often patients complain of the post-operative pain and bleeding associated with the procedure, and a significant subset of patients remain symptomatic even after multiple surgeries. Since FESS is considered an option only for the most severe cases (those showing abnormalities under CT scan), a large population of patients exist that can neither tolerate the prescribed medications nor be considered candidates for surgery. Further, because the methodologies to assess sinus disease are primarily static measurements (CT, MRI), patients whose symptoms are episodic are often simply offered drug therapy when in fact underlying mechanical factors may play a significant role. To date, there is no mechanical therapy offered for these patients, and even though they may fail pharmaceutical therapies, no other course of action is indicated. This leaves a large population of patients in need of relief, unwilling or afraid to take steroids, but not sick enough to qualify for surgery.

Some experimental or investigational procedures have also been performed in an effort to treat sinusitis by methods that are less invasive and/or less damaging to ancillary tissues than FESS: For example, European physicians have reported the use of a hydrophilic guidewire and standard PTCA balloon catheter to treat restenosis of surgically created openings in diseased frontal sinuses and stenotic nasal conae. Göttmann, D., Strohm, M., Strecker, E. P., Karlsruhe, D. E., Balloon dilatation of Recurrent Ostial Oclusion of the Frontal Sinus, Abstract No. B-0453, European Congress of Radiology (2001); Strohm, M., Göttmann, D., Treatment of Stenoses of Upper Air Routes by Balloon Dilation, Proceeding of the 83$^{rd}$ Annual Convention of the Association of West German ENT Physicians (1999). The interventions described in this abstract were conducted only on frontal sinuses that had previously been surgically modified and nasal conae. These techniques were not reported to be usable for the treatment of sinus ostia that has not previously been surgically altered or ostia of sinuses other than the easily accessible frontal sinuses. Also, in these reported cases, standard vascular guidewires and angioplasty balloon catheters were used. The techniques described in these publications have not been widely adopted by ENT surgeons, possibly due to the fact that they lacked important novel improvements and modifications as described in this patent application and prior U.S. patent application Ser. Nos. 10/829,917, 10/912,578 and 10/944,270, of which this application is a continuation-in-part.

Other methods and devices for sinus intervention using dilating balloons have been disclosed in U.S. Pat. No. 2,525,183 (Robison) and U.S. Patent Publication No. 2004/0064150 A1 (Becker). For example, U.S. Pat. No. 2,525,183 (Robison) discloses an inflatable pressure device which can be inserted following sinus surgery and inflated within the sinus. The patent does not disclose device designs and methods for flexibly navigating through the complex nasal anatomy to access the natural ostia of the sinuses. The discussion of balloon materials is also fairly limited to thin flexible materials like rubber which are most likely to be inadequate for dilating the bony ostia of the sinus.

U.S. patent publication No. 2004/0064150 A1 (Becker) discloses balloon catheters formed of a stiff hypotube to be pushed into a sinus. The balloon catheters have a stiff hypotube with a fixed pre-set angle that enables them to be pushed into the sinus. In at least some procedures wherein it is desired to position the balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to design a stiff-shaft balloon catheter that is optimally shaped for use in all individuals. Indeed, rigid catheters formed of hypotubes that have pre-set angles cannot be easily adjusted by the physician to different shapes to account for individual variations in the anatomy. In view of this, the Becker patent application describes the necessity of having available a set of balloon catheters, each having a particular fixed angle so that the physician can select the appropriate catheter for the patient's anatomy. The requirement to test multiple disposable catheters for fit is likely to be very expensive and impractical. Moreover, if such catheter are disposable items (e.g., not sterilizable and reusable) the need to test and discard a number of catheters before finding one that has the ideal bend angle could be rather expensive.

The prior art has not provided catheters, devices, systems and methods that are optimal for minimally invasive treatment of sinusitis, mucocysts, tumors, infections, hearing disorders, fractures, choanal atresia or other conditions of the paranasal sinuses, Eustachian tubes, Lachrymal ducts and other ear, nose, throat or mouth structures.

SUMMARY OF THE INVENTION

In general, the present invention provides methods, devices and systems for diagnosing and/or treating sinusitis, mucocysts, tumors, infections, hearing disorders, fractures, choanal atresia or other conditions of the paranasal sinuses, Eustachian tubes, llachrymal ducts, ducts of salivary glands and other ear, nose, throat or mouth structures.

In accordance with the present invention, there are provided methods wherein one or more flexible catheters or other flexible elongate devices as described herein are inserted in to the nose, nasopharynx, paranasal sinus, Eustachian tubes, middle ear, lachrymal ducts, ducts of salivary glands or other anatomical passageways of the ear, nose, throat or mouth to perform an interventional or surgical procedure. Examples of procedures that may be performed using these flexible catheters or other flexible elongate devices include but are not limited to: delivering contrast medium; performing an imaging study, delivering a therapeutically effective amount of a therapeutic substance; implanting a stent or a tissue remodeling device, substance delivery implant or other therapeutic apparatus; cutting, ablating, debulking, cauterizing, heating, dilating or otherwise modifying tissue such as nasal polyps, abberant or enlarged tissue, abnormal tissue, etc.; grafting or implanting cells or tissue; reducing, setting, affixing or otherwise treating a fracture; delivering a gene or gene therapy preparation; cutting, ablating, debulking, cauterizing, heating, freezing, lasing, forming an osteotomy or trephination in or otherwise modifying bony or cartilaginous tissue within paranasal sinus, nasopharynx, Eustachian tube, middle ear, Lachrymal duct or elsewhere within the ear, nose, throat or mouth; remodeling or changing the shape, size or configuration of a sinus ostium or other anatomical structure that affects drainage from one or more paranasal sinuses; removing puss or aberrant matter from the paranasal sinus or elsewhere within the nose; scraping or otherwise removing cells that line the interior of a paranasal sinus; removing all or a portion of a tumor; removing a polyp; delivering histamine, an allergen or another substance that causes secretion of mucous by tissues within a paranasal sinus to permit assessment of drainage from the sinus etc.

Still further in accordance with the invention, there are provided novel access, stabilizing and occluding devices. They may be used to facilitate insertion of working devices such as endoscopes, guidewires, catheters (e.g. balloon catheters), tissue cutting or remodeling devices, sizing devices, biopsy devices, image-guided devices containing sensors or transmitters, electrosurgical devices, energy emitting devices, devices for injecting diagnostic or therapeutic agents, devices for implanting devices such as stents, substance eluting devices, substance delivery implants, etc. into the paranasal sinuses and other structures in the ear, nose, throat or mouth for performing some or all of the procedures described herein.

Still further in accordance with the invention, there are presented several modalities for navigation and imaging of the interventional devices within the nose, nasopharynx, paranasal sinuses, Eustachian tubes, middle ear, lachrymal ducts, ducts of salivary glands or other anatomical passageways of the ear, nose, throat or mouth using endoscopic, fluoroscopic, radiofrequency localization, electromagnetic and other radiative energy based imaging and navigation modalities. These imaging and navigation technologies may also be referenced by computer directly or indirectly to pre-existing or simultaneously created 3-D or 2-D data sets which help the doctor place the devices within the appropriate region of the anatomy.

Still further in accordance with the invention, there are provided methods for improving drainage from a paranasal sinus that has a natural ostium that has not previously been surgically altered, said method comprising the steps of: A) providing an elongate guide (e.g., a wire, rod, probe, guidewire, flexible member, malleable member, tube, cannula, catheter, stylets, etc.) and a dilator (e.g., a dilation catheter, balloon catheter, expandable member, etc.); B) advancing the elongate guide to a position within or near the ostium; C) using the elongate guide to advance the dilatior to a position where the dilator is within the ostium; and D) using the dilator to dilate the natural ostium. The dilation of the natural ostium may, in at least some cases, result in breaking or rearrangement of bone that underlies the mucosa of the ostium.

Still further in accordance with the invention, there is provided a method for treating a mucocyst or other or other flowable-substance-containing structure located within a paranasal sinus, said method comprising the steps of A) providing a penetrator that is useable to form an opening in the mucocyst or other flowable-substance-containing structure; B) providing a compressor useable to compress the mucocyst or other flowable-substance-containing structure after an opening has been formed therein by the penetrator such that its contents will be forced out of the opening formed by the penetrator; C) advancing the penetrator into the paranasal sinus and using the penetrator to form an opening in the mucocyst or other flowable-substance-containing structure; and D) positioning the compressor in the paranasal sinus and using the compressor to compress the mucocyst or other flowable-substance-containing structure such that its contents will be forced out of the opening formed by the penetrator.

Still further in accordance with the invention, there is provided a method for dilating a Eustachian tube in a human or animal subject, said method domprising the steps of: A) providing a guide member (e.g., a guidewire) that is insertable through the nose and is advanceable into the Eustachian tube through the pharyngeal ostium of the Eustachian tube and a dilator that is advanceable over the guidewire and useable to dilate the Eustachian tube; B) inserting the guidewire into the Eustachian tube; C) advancing the dilator over the guide member and into the Eustachian tube; and D) using the dilator to dilate the Eustachian tube. In some embodiments of this method, the guide member (e.g., guidewire) may have an anchor (e.g., a balloon) for holding the guide member in a substantially fixed position within the Eustachian tube, thereby guarding against inadvertent advancement of the guide member or dilation catheter into the middle ear as may injure the bones of the middle ear. In some embodiments, marker(s) such as radiopaque markers may be provided on the guide memner and/or may be inserted into the adjacent ear canal next to the tympanic membrane to allow the operator to clearly view the location at which the Eustachian tube enters the middle ear, thereby further guarding against inadvertent advancement of the device(s) into the middle ear.

Still further in accordance with the invention, there is provided a method for modifying a bony structure within the nose or paranasal sinus human or animal subject, said method comprising the steps of: A) providing a direct viewing apparatus (e.g., a scope, rigid scope, flexible scope, camera, video camera, intranasal camera similar to an intraoral camera but sized for insertion into the nares or nasal cavity); B) inserting the direct viewing apparatus into the nose; C) advancing a guide device to a first location within the nasal cavity or paranasal sinus under direct viewing using the direct viewing apparatus; D) providing an indirect viewing apparatus (e.g., an imaging device, fluoroscope, fluoroscope with C-arm, magnetic resonance imaging device, tomographic device, CT scanner, electromagnetic navigational and/or guidance system, PET scanner, combination CT/PET scanner and optical coherence tomography device, etc.); E) advancing a working device (e.g., an endoscope, wire, probe, needle, catheter, balloon catheter, dilation catheter, dilator, balloon, tissue cutting or remodeling device, suction or irrigation device, imaging device, sizing device, biopsy device, image-guided device containing sensor or transmitter, electrosurgical device, energy emitting device such as laser, rf, etc., device for injecting diagnostic or therapeutic agent, device for implanting other articles such as stents, substance eluting or delivering device, implant, etc.) over the guide device to a second location location within the nasal cavity or paranasal sinus, under indirect viewing using the direct viewing apparatus; and F) using the working device to perform a therapeutic or diagnostic procedure.

Still further in accordance with the invention, there is provided a method for determining the position of a device within the body of a human or animal subject, said method comprising the steps of A) providing a device having an electromagnetic element (e.g., a sensor or electromagnetic coil) thereon; B) providing a plurality of fiducial markers which emit electromagnetic energy and an attachment substance or apparatus for removably attaching the fiducial markers to teeth, bones or other anatomical structures; C) using the attachment substance or apparatus to removably attach the fiducial markers to teeth, bones or other anatomical structures of the subject's body; D) performing an imaging procedure to obtain an image of a portion of the subjects body including the fiducial markers; and, thereafter, E) advancing the device into the subject's body and detecting the electromagnetic element on the device as well as the electromagnetic energy emitted by the fiducial markers; and F) using the image obtained in Step D and the information dectected in Step E to determine the current position of the device within the subject's body.

Further aspects, details and embodiments of the present invention will be understood by those of skill in the art upon reading the following detailed description of the invention and the accompanying drawings.

BRIEF DESCRIPTION OF THE DRAWINGS

FIG. 8E shows a perspective view of an embodiment of a guide catheter comprising two bent or angled or curved regions to facilitate access to the maxillary sinuses.

FIG. 8F shows a perspective view of a second embodiment of a guide catheter comprising two bent or angled or curved regions and a hypotube to facilitate access to the maxillary sinuses.

FIG. 8G shows a coronal section of the paranasal anatomy showing a method of accessing a maxillary sinus ostium using the guide catheter of FIG. 8F.

FIG. 8H shows a sagittal section of the paranasal anatomy showing the method of FIG. 8G to access a maxillary sinus ostium using the guide catheter of FIG. 8F.

FIG. 8I shows a perspective view of an example of a guide catheter comprising a common proximal portion and a plurality of detachable distal tips.

FIGS. 10A-10C show various steps of a method of using the probing device shown in FIG. 10 to access an anatomical region.

FIG. 14A shows a crossectional view through the plane 14A-14A of FIG. 14.

FIGS. 14B-14D show the various steps of dilating an anatomical opening using the balloon catheter in FIG. 14.

FIG. 15 shows a perspective view of a balloon catheter comprising a sleeve for delivering diagnostic or therapeutic agents.

FIG. 15A shows a crossectional view through plane 15A-15A of FIG. 15.

FIG. 16 shows a perspective view of a balloon catheter comprising one or more agent delivery reservoirs.

FIG. 16A shows a crossectional view through plane 16A-16A of FIG. 16.

FIG. 17 shows a perspective view of a balloon catheter comprising a balloon comprising one or more micropores.

FIG. 17A shows a crossectional view through the plane 17A-17A of FIG. 17.

FIGS. 18A-18C show the steps of a method of using the balloon catheter of FIG. 18 to dilate an anatomical region.

FIG. 21A shows a perspective view of the distal region of the cutting device of FIG. 21 wherein the cutting jaws are closed as seen from the distal end of the cutting device.

FIG. 21B shows a perspective view of one embodiment of the cutting jaws of the cutting device of FIG. 21.

FIG. 21C shows a crossectional view of the cutting device in FIG. 21 through cutting plane 21C-21C.

FIGS. 24A'-24A"" show a method of creating drainage channels for sinus secretions in Ethmoid sinus.

FIGS. 30A-30B show a sectional view of an anatomical region showing a method of expanding an anatomical opening using the drilling device of FIG. 30.

FIG. 31A shows a crossection through the outer balloon in the catheter of FIG. 31 through plane 31A-31A.

FIGS. 31B-31D show various steps of a method of providing an internal cast for a fractured bony cavity using the catheter shown in FIG. 31

FIG. 32A shows an enlarged view of region 32A in FIG. 32.

FIG. 33B shows a front view of a human head with a portion of the face removed to show an embodiment of a method of introducing a guidewire into a Eustachian tube.

FIG. 35A shows an enlarged view of an embodiment of a low profile proximal region of the guidewire in FIG. 35.

FIG. 35B shows a perspective view of a method of advancing a diagnostic or therapeutic device over the guidewire in FIG. 35.

FIG. 35C shows a perspective view of an embodiment of a guidewire comprising a sensor having a diagnostic or therapeutic device preloaded on the guidewire.

FIG. 35D shows a perspective view of a second embodiment of a guidewire comprising a sensor having a diagnostic or therapeutic device preloaded on the guidewire.

DETAILED DESCRIPTION

The following detailed description, the accompanying drawings and the above-set-forth Brief Description of the Drawings are intended to describe some, but not necessarily all, examples or embodiments of the invention. The contents of this detailed description, the accompanying drawings and the above-set-forth Brief Description of the Drawings do not limit the scope of the invention in any way.

A number of the drawings in this patent application show anatomical structures of the ear, nose and throat. In general, these anatomical structures are labeled with the following reference letters:

| | |
|---|---|
| Nasal Cavity | NC |
| Nasopharynx | NP |
| Frontal Sinus | FS |
| Frontal Sinus Ostium | FSO |
| Ethmoid Sinus | ES |
| Ethmoid Air Cells | EAC |
| Sphenoid Sinus | SS |
| Sphenoid Sinus Ostium | SSO |
| Maxillary Sinus | MS |
| Maxillary sinus ostium | MSO |
| Mucocyst | MC |
| Eustachian tube | ET |
| Cochlea | C |
| Tympanic cavity | TC |
| Middle turbinate | MT |
| Inferior turbinate | IT |
| Uncinate | UN |

Figure 1:
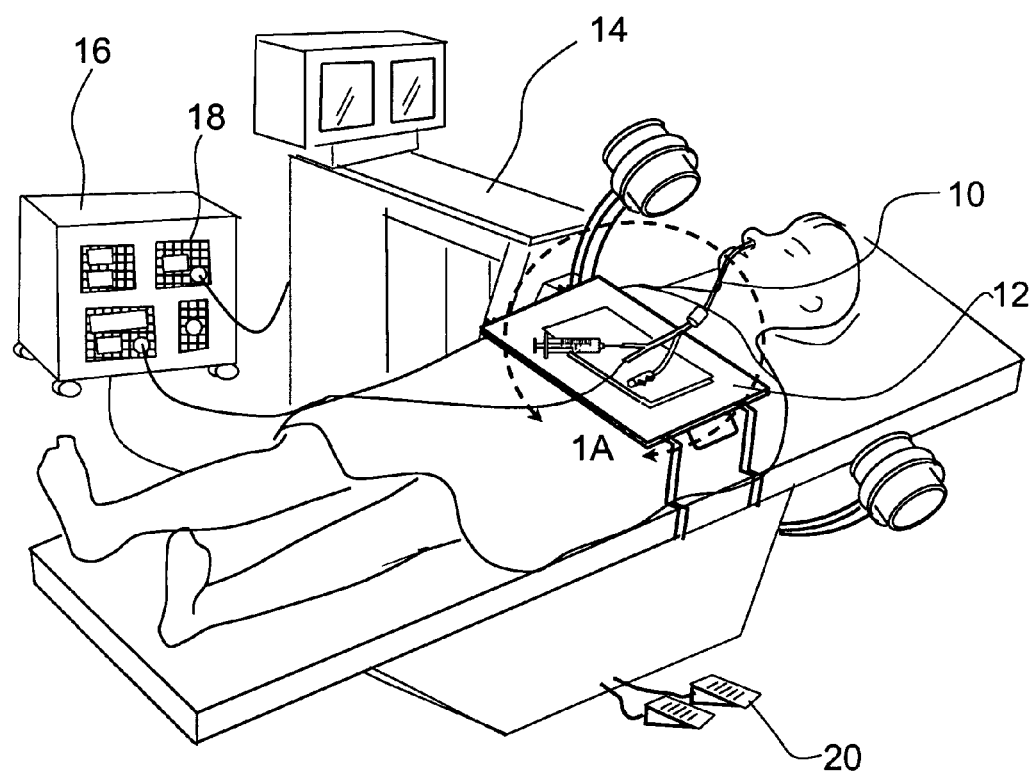
FIG. 1 shows a schematic diagram of the general working environment of an example of a system for catheter-based minimally invasive sinus surgery being used to perform a sinus surgery on a human patient.

FIG. 1 shows a schematic diagram of the general working environment of an example of a system for catheter-based minimally invasive sinus surgery being used to perform a sinus surgery on a human patient. The human patient is treated by a working device 10. Working device 10 may be connected to one or more auxiliary devices located on a treatment tray 12. A C-arm fluoroscope 14 provides fluoroscopic visualization of anatomical regions during the procedure. An instrument console 16 comprising one or more functional modules 18 may also be present. Examples of functional modules that can be used with the invention are:

1. Suction pump for delivering a controlled amount of negative pressure or vacuum to a suction device,
2. Irrigation pump to deliver saline, antibiotic solution or other suitable irrigation medium,
3. Power module to supply power to drills or other electrical devices,
4. Storage modules for storing instruments, medications etc.,
5. Energy delivery module to provide radiofrequency, laser, ultrasound or other therapeutic energy to a surgical device,
6. Fluoroscope, MRI, CT, Video, Endoscope or Camera or other imaging modules to connect or interact with devices used during various diagnostic or therapeutic procedures,
7. Display module e.g. a LCD, CRT or Holographic screen to display data from various modules such as an endoscope, fluoroscope or other data or imaging module,
8. Remote control module to enable an operator to control one or more parameters of one or more functional modules 18,
9. Programmable Microprocessor that can store one or more operation settings for one or more functional modules 18 etc., and
10. Stabilization device for holding various apparatuses during the procedure which may include a stabilization arm, table, clip, intranasal or extranasal inflatable support or robotically controlled apparatus,
11. Rotary drive module for rotating rotatable device such as a drill or auger (e.g., a motor having a rotation drive shaft or drive cable attached thereto.

One or more functional modules 18 may be connected to the working device 10. Instrument console module 16 can be controlled by console control means 20, e.g. a foot pedal controller, a remote controller etc. Instrument console 16 may be fitted with wheels to enable an operator to change the position of the instrument console 16 in an operating area. In one embodiment, instrument console module 16 and C-arm fluoroscope 14 are integrated in a single unit.

Figure 1A:
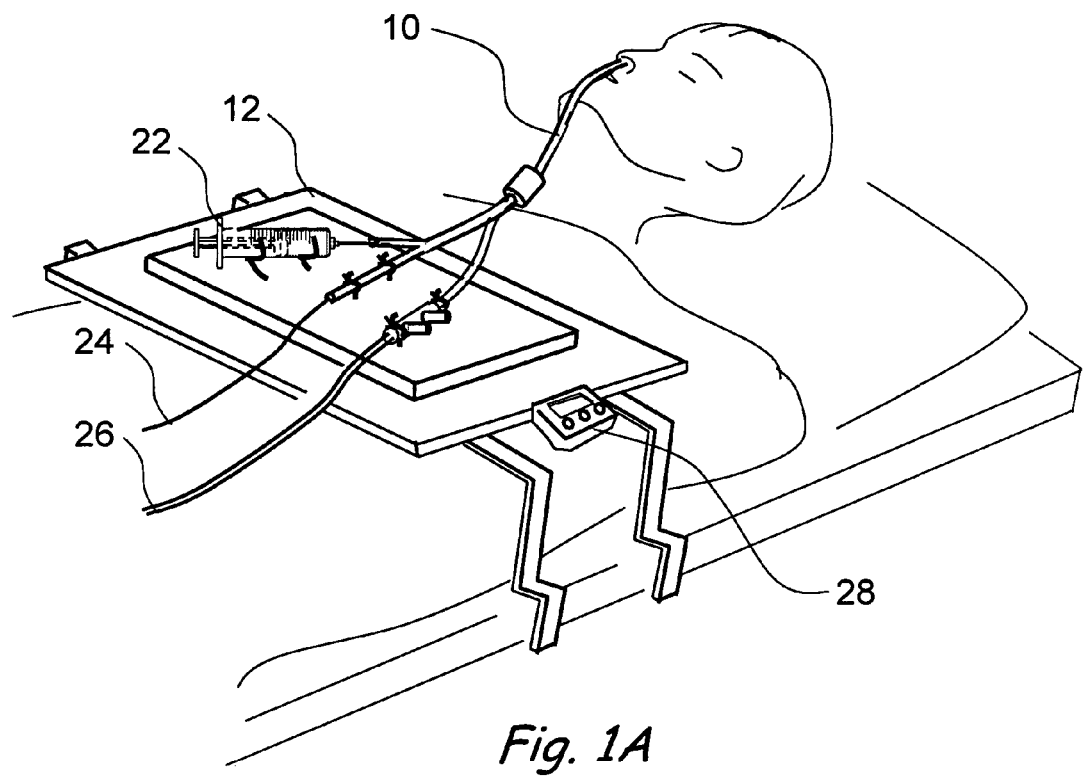
FIG. 1A shows a magnified view of region 1A of FIG. 1 showing a system for catheter-based minimally invasive sinus surgery of a human patient.

FIG. 1A shows a magnified view of region 1A of FIG. 1 showing a system for catheter-based minimally invasive sinus surgery of a human patient. In FIG. 1A, a balloon catheter is used as an example of working device 10. Working device 10 has attachments for a variety of auxiliary devices such as a balloon inflation syringe 22, a guidewire 24 and a suction or irrigation tube 26. Working device 10 and the auxiliary devices may be detachably attached to treatment tray 12. Treatment tray 12 may comprise one or more treatment tray controllers 28 to control one or more treatment parameters. Treatment tray 12 may comprise one or more storage modules to store devices used during a surgery e.g. irrigation bottles, swabs etc.

Figure 1B:
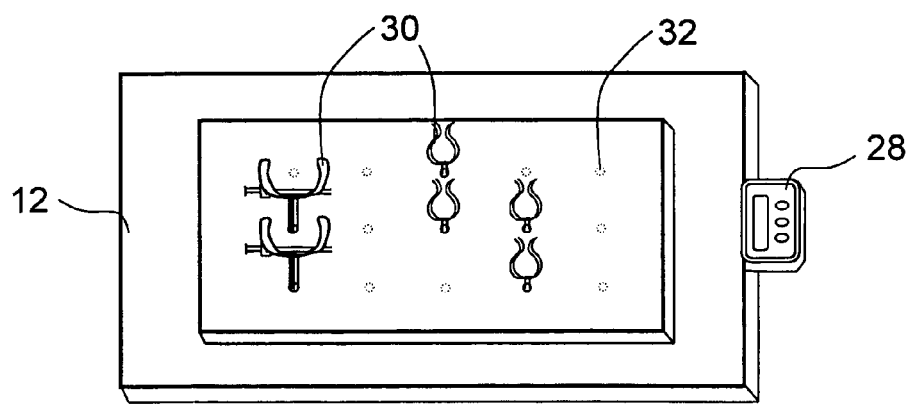
FIG. 1B shows a perspective view of a treatment tray for catheter-based minimally invasive sinus surgery of a human patient.

FIG. 1B shows a perspective view of a treatment tray for catheter-based minimally invasive sinus surgery of a human patient. Treatment tray 12 comprises one or more device holders 30 to detachably hold devices during the surgery. In one embodiment, device holders 30 are detachably attached to device holder slots 32 on treatment tray 12. Thus the position of device holders 30 on treatment tray 12 can be changed by removing a device holder 30 from a device holder slot 32 and transferring to a new device holder slot 32.

Figure 2A:
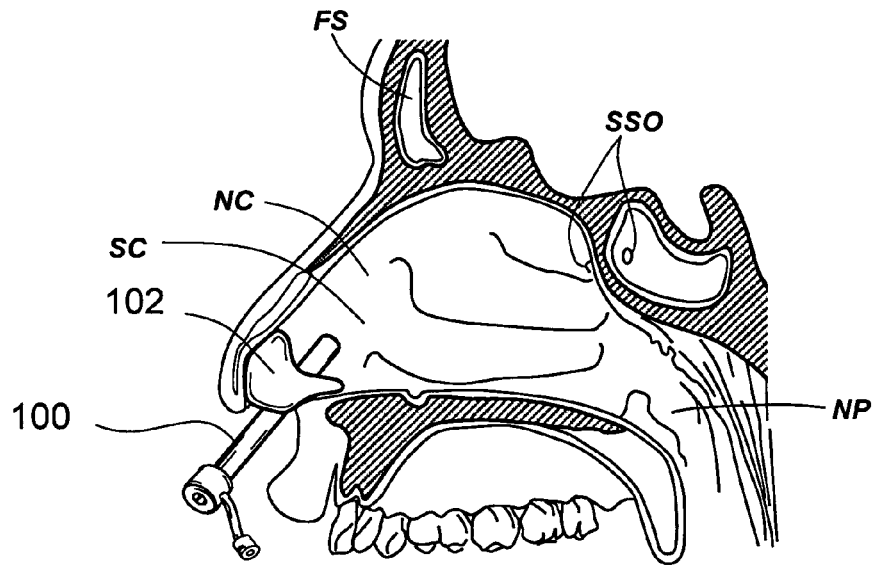
FIG. 2A shows a portion of a stabilizing device comprising a stabilizing member.

FIG. 2A shows a portion of a stabilizing device 100 comprising a stabilizing member 102. Stabilizing member 102 comprises a lumen through which working device 10 can be introduced. In this example, stabilizing member 102 is located in a nostril. Alternatively, stabilizing member 102 may be located in other suitable regions of the head e.g. the nasal passages.

Figure 2B:
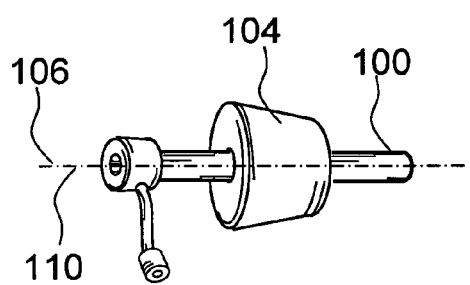
FIGS. 2B-2D show various alternate embodiments of stabilizing member of FIG. 2A.
Figure 2C:
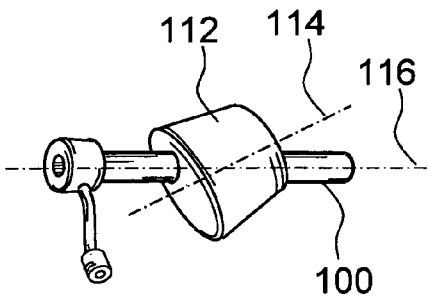
Figure 2D:
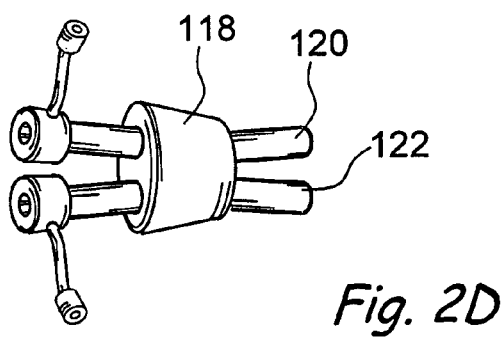

Stabilizing member 102 may be oriented to stabilizing device 100 in a variety of orientations. Also, the stabilizing member can be used to stabilize more than one working device. FIGS. 2B-2D show various alternate embodiments of stabilizing member 102 of FIG. 2A. FIG. 2B shows an embodiment of a radially symmetrical stabilizing member 104, wherein the axis 106 of stabilizing member 104 is substantially parallel to the axis 110 of stabilizing device 100. FIG. 2C shows an embodiment of a radially symmetrical stabilizing member 112. The axis 114 of stabilizing member 112 is substantially non-parallel to the axis 116 of stabilizing device 100. FIG. 2D shows an embodiment of a stabilizing member 118, wherein stabilizing member 118 comprises two lumens enclosing a first stabilizing device 120 and a second stabilizing device 122. Suitable materials that can be used for constructing the stabilizing members are:

Foam materials such as polyurethane foam, polyvinyl chloride foam, Thermal-Reactive Foam™ etc.,
Inflatable members such as compliant or non-compliant balloons, Moldable materials such as silicone rubber or wax, Metals such as stainless steel or super-elastic or shape memory metals such as Nitinol Thermoplastic elastomers such as block copolymers e.g. styrene-butadiene-styrene (SBS) rubber or ionomers etc.

The stabilizing members may be pre-molded to a pre-defined shape.

Figure 2E:
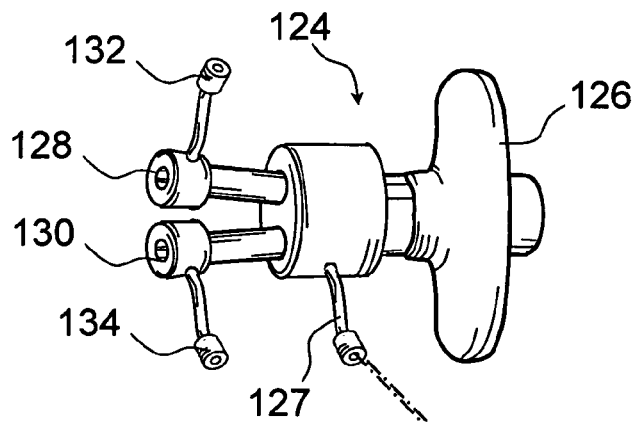
FIG. 2E-2G show perspective views of various embodiments of inflatable occluding devices.
Figure 2F:
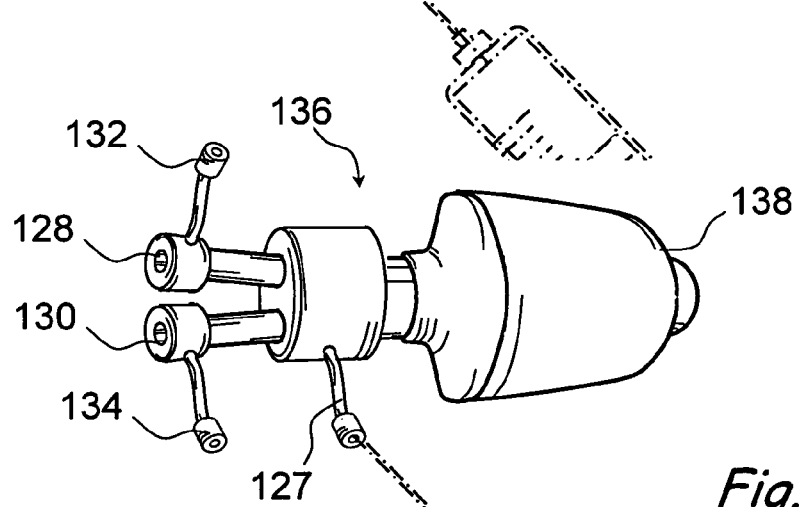
Figure 2G:
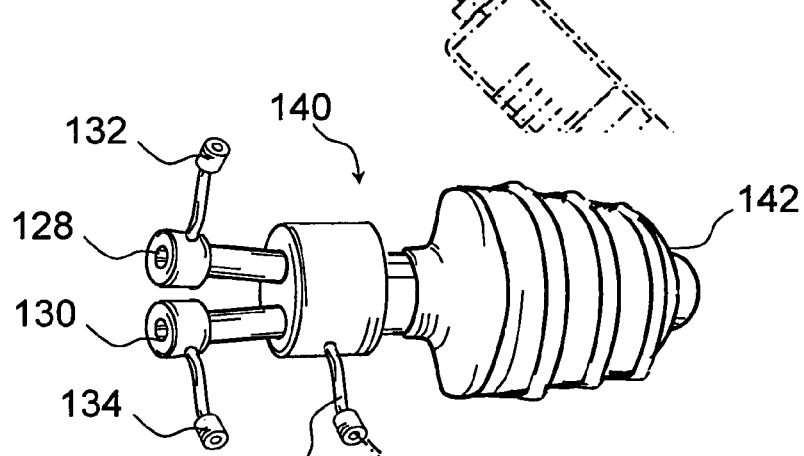

FIGS. 2E-2G show perspective views of various embodiments of inflatable occluding devices. FIG. 2E shows a partial view of an occluding device 124 comprising an inflatable occluding member 126. Inflatable occluding member 126 may be made of compliant materials e.g. silicone rubber, or non-compliant materials e.g. polyethylene terephthalate (PET). Inflatable occluding member 126 can be inflated through an inflation port 127 located on the occluding device 124. Occluding device 124 can have one or more device insertion ports. The device insertion ports can be used to insert a variety of diagnostic or therapeutic devices such as endoscopes, guidewires, catheters etc. In this example, occluding device 124 has a first device insertion port 128 and a second device insertion port 130. The device insertion ports may comprise one or more flush ports. In this example, occluding device 124 comprises a first flush port 132 located on first device insertion port 128 and a second flush port 134 located on second device insertion port 130. Such an occluding device may be used for occluding one or two nostrils to provide a gas-tight or liquid-tight seal against the nostril or to stabilize devices that are passed through the device insertion ports on the occluding device.

The inflatable occluding member may be made of variety of shapes. FIG. 2F shows an occluding device 136 comprising an inflatable occluding member 138 of an elongated shape wherein the diameter of the inflatable occluding member 138 tapers along the length of occluding device 136. Inflatable occluding member 138 may also be spherical, disk shaped, cylindrical, conical etc.

The inflatable occluding member may comprise a variety of surface features. For example, FIG. 2G shows an occluding device 140 comprising an inflatable occluding member 142. Inflatable occluding member comprises a series or parallel circular ribs on its surface. Other surface features such as coatings (e.g. friction increasing coatings, abrasion resisting coatings, puncture resisting coatings, conductive coatings, radiopaque coatings, echogenic coatings, thrombogenicity reducing coatings and drug releasing coatings etc.), braids, grooves etc. may also be present on inflatable occluding member 142.

Figure 3A:
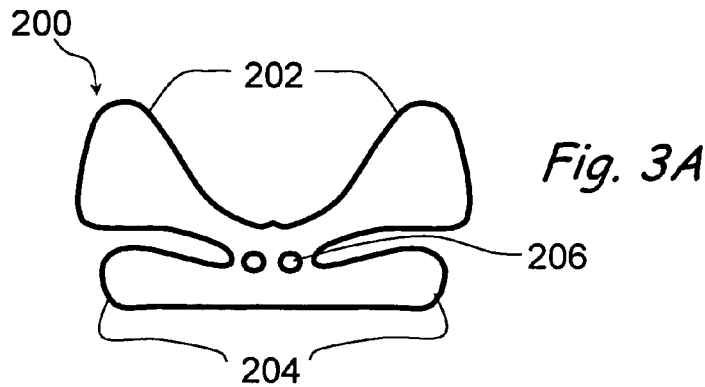
FIGS. 3A-3D' show embodiments of stabilizing members comprising an adhesive element.

FIGS. 3A-3D' show embodiments of stabilizing members comprising an adhesive element. FIG. 3A shows front view of an embodiment of a stabilizing member 200 comprising a pair of upper wings 202 and a pair of lower wings 204. In this embodiment, upper wings 202 are larger than lower wings 204. Stabilizing member 200 further comprises one or more orifices 206 through which one or more working devices can be introduced. Stabilizing member 200 is made of a light weight, flexible material that conforms to the contours of the patient's body. Examples of such materials are woven and non-woven fabrics, plastic films (e.g. polyvinylchloride films, polypropylene films etc.), cellulose, paper etc. Stabilizing member 200 may have a porous structure for increased transmission of water vapor produced in perspiration from the skin under stabilizing member 200. One surface of stabilizing member 200 is coated with an adhesive to enable stabilizing member 200 to adhere to a surface on a patient's body. A non-allergenic adhesive is used to minimize skin irritation. Examples of such adhesives are non-allergenic pressure-sensitive adhesives such as silicone pressure sensitive adhesives, rubber pressure sensitive adhesives and acrylic or hydrogel pressure sensitive adhesives. Stabilization member 200 may also be lubricated with a silicone or other biocompatible lubricant at the orifice to allow easier introduction and removal of devices.

Figure 3B:
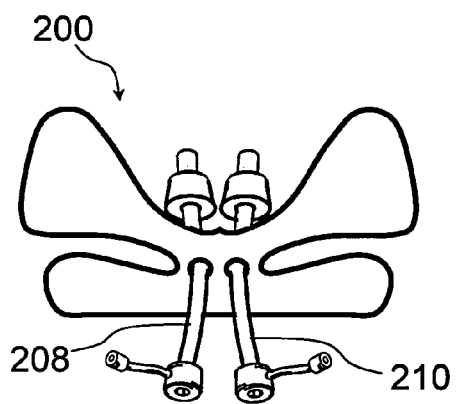
Figure 3C:
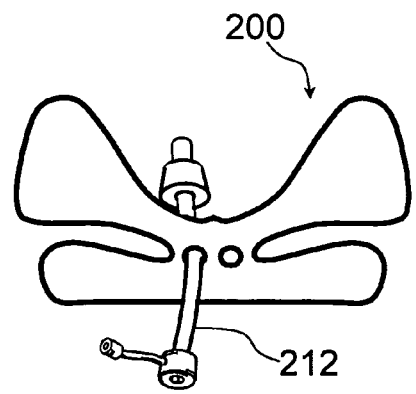

Stabilizing member 200 may be used to stabilize one or more working devices. FIG. 3B shows a front view of stabilizing member 200 of FIG. 3A with two working devices: a first working device 208 and a second working device 210. FIG. 3C shows a front view of the stabilizing member 200 of FIG. 3A with a single working device 212.

Figure 3D:
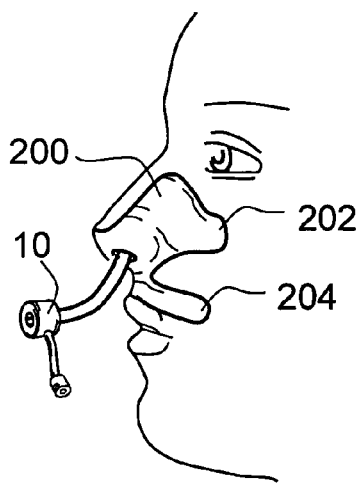
Figure 3D:
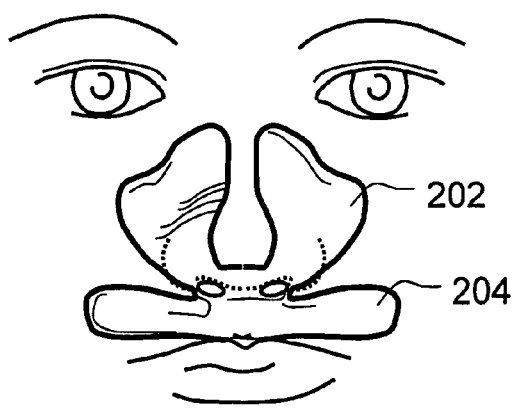

FIG. 3D shows a side view of stabilizing member 200 of FIG. 3A attached to a patient's body. Upper wings 202 are attached on the nose of the patient. Lower wings 204 are attached above the upper lip of the patient. A working device 10 is introduced through the orifice 206 into the patient's nose. FIG. 3D' shows a front view of stabilizing member 200 of FIG. 3A attached to a patient's body.

Figure 4A:
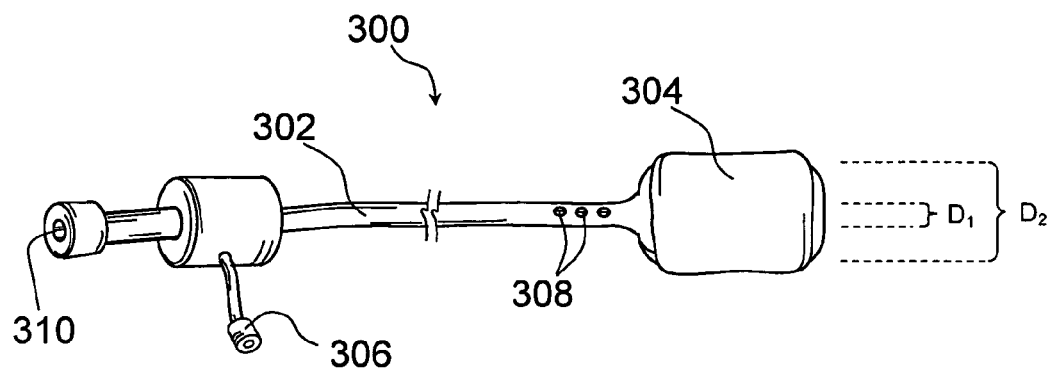
FIGS. 4A and 4B show perspective views of an occluding device in deflated and inflated states respectively.
Figure 4B:
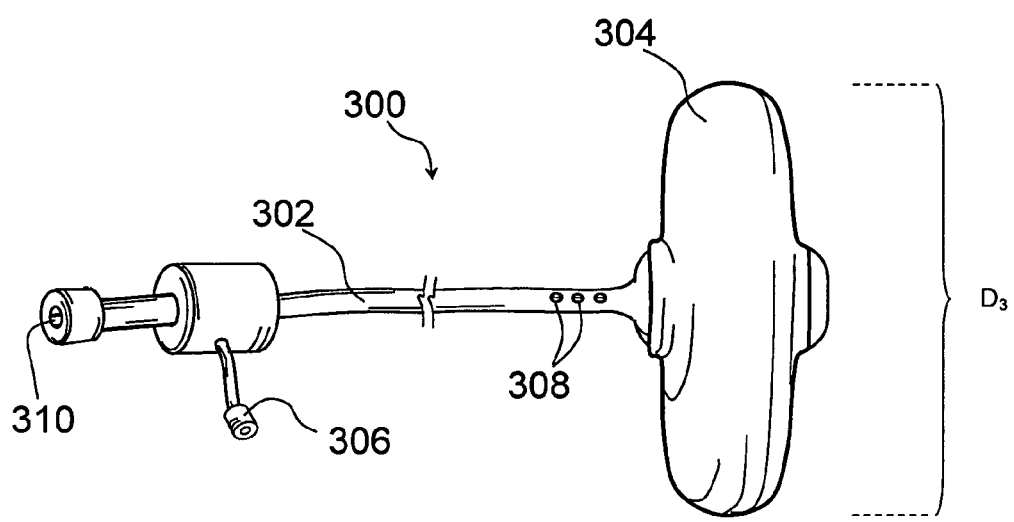

FIGS. 4A and 4B show perspective views of an occluding device in deflated and inflated states respectively. Occluding device 300 comprises a shaft 302 and an inflatable balloon 304 located on distal region of shaft 302. Shaft 302 has a diameter $D.sub.1$ and inflatable balloon 304 has a diameter $D.sub.2$ in the deflated state, wherein $D.sub.2$ is greater then $D.sub.1$. Inflatable balloon 304 can be made of compliant materials e.g. polyurethane, silicone etc. or non-compliant materials e.g. polyethylene terephthalate etc. Inflatable balloon 304 can be inflated through balloon inflation port 306 located on proximal region of occluding device 300. The inflated diameter $D.sub.3$ of the inflatable balloon is greater than $D.sub.2$ and is particularly suitable for occluding the Nasopharynx. Occluding device 300 further comprises a series of aspiration ports 308 located proximal to inflatable balloon 304. Aspiration ports 308 are connected to an aspiration lumen 310 to aspirate contents proximal to inflatable balloon 304.

Figure 5:
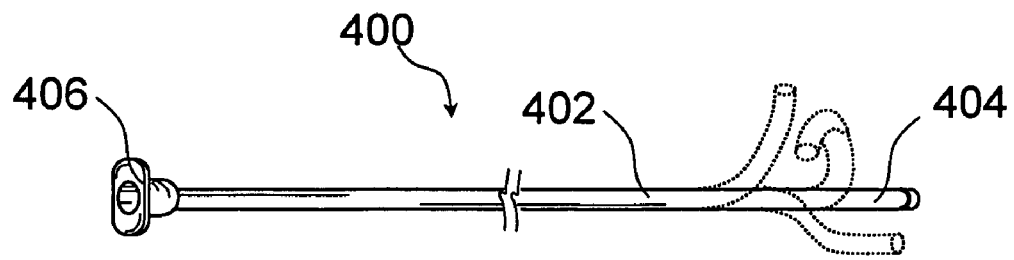
FIG. 5 shows a perspective view of a guide catheter comprising a plastically deformable (malleable) region.

Any diagnostic or therapeutic device disclosed herein may comprise one or more malleable regions. For example, FIG. 5 shows a perspective view of a guide catheter comprising a plastically deformable (malleable) region. Guide catheter 400 comprises a shaft 402 comprising a malleable region 404 located on distal region of shaft 402. Shaft 402 may comprise stiffening elements e.g. a braid, hypotube etc. Malleable region 404 may comprise malleable metallic tubes, rods (e.g. rods embedded in shaft 402 etc.), wires etc. Examples of metals that can be used for constructing malleable region 404 are malleable stainless steel, fully annealed stainless steel, copper, aluminum etc. Guide catheter 400 further comprises a threaded luer 406 located on proximal end of shaft 402. In this example, malleable region 404 is located on distal end of guide catheter 400. Malleable region 404 can also be located on proximal region or any other intermediate region on shaft 402. Shaft 402 may also comprise more than one malleable regions. Such a design comprising one or more malleable regions can be used for any of the devices mentioned herein such as catheters with working elements, guide catheters, guide catheters with a pre-set shape, steerable guide catheters, steerable catheters, guidewires, guidewires with a preset shape, steerable guidewires, ports, introducers, sheaths or other diagnostic or therapeutic devices.

Figure 6:
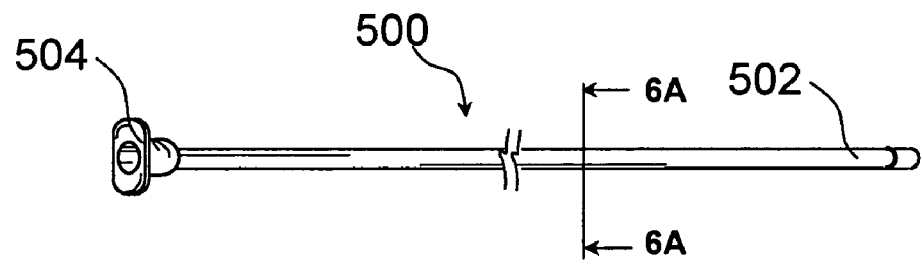
FIG. 6 shows a perspective view of a guide catheter comprising a lubricious layer.
Figure 6A:
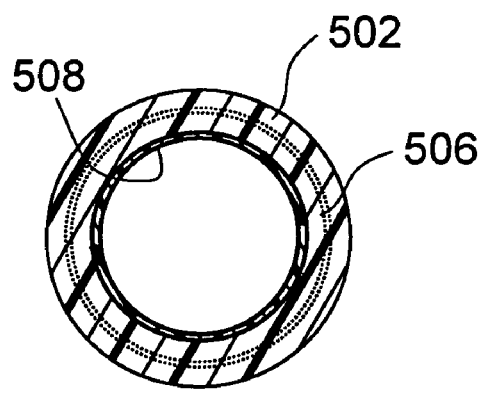
FIG. 6A shows a crossecional view of the guide catheter of FIG. 6 through the plane 6A-6A.

FIG. 6 shows a perspective view of a guide catheter comprising a lubricious layer. Guide catheter 500 comprises a shaft 502 comprising a threaded luer 504 located on the proximal end of the shaft 502. FIG. 6A shows a crossectional view of the guide catheter of FIG. 6 through the plane 6A-6A. Shaft 502 comprises a braid 506 embedded in the shaft. Shaft 502 further comprises a lubricious layer 508 located on the inner surface of shaft 502. Lubricious layer 508 may be made of suitable materials such as Teflon liners, Teflon coatings or Teflon sheaths. Such a design comprising one or more lubricious layers can be used for any of the devices mentioned herein such as catheters with working elements, guide catheters, guide catheters with a pre-set shape, steerable guide catheters, steerable catheters, guidewires, guidewires with a pre-set shape, steerable guidewires, ports, introducers, sheaths or other diagnostic or therapeutic devices.

Figure 7:
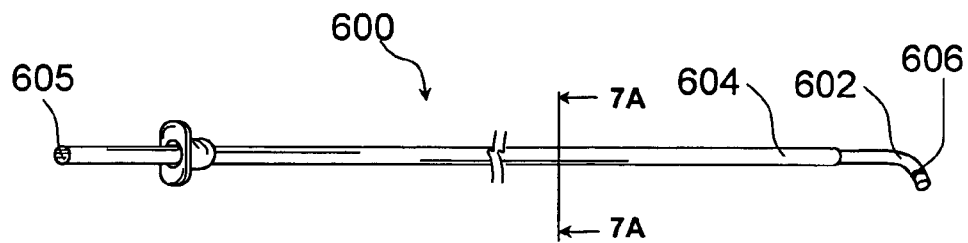
FIG. 7 shows perspective view of an embodiment of a guide catheter comprising a straight hypotube.

FIG. 7 shows perspective view of an embodiment of a guide catheter comprising a straight hypotube. Guide catheter 600 comprises a tubular element 602 and a hypotube 604 attached to the external surface of tubular element 602. Suitable materials for constructing hypotube 604 are Stainless Steel 304, Nitinol etc. In one embodiment, hypotube 604 is annealed to the external surface of tubular element 602. Tubular element 602 can be made from a variety of materials including Pebax, HDPE etc. Tubular element 602 may comprise a braid or a jacket. In an embodiment, tubular element 602 comprises a lubricious coating 605 on its inner surface. The lubricious coating 605 can be made of suitable lubricious materials such as Teflon. In an embodiment, tubular element 602 comprises a bent or angled region near the distal end of tubular element 602. The bent or angled region may enclose an angle from 0 degrees to 180 degrees. Further this bent or angled region may be further bent out of plane to present a compound three-dimension end shape. Hypotube 604 can be malleable or substantially stiff. A malleable hypotube can be used in situations where the guide catheter 600 has to be bent or distorted to optimize its shape to conform to a patient's anatomy. Examples of materials that can be used to make a malleable hypotube are malleable stainless steel, fully annealed stainless steel, copper, aluminum etc. A substantially stiff hypotube can be used in situations where extra support is needed for introduction or removal or devices through guide catheter 600. Examples of materials that can be used to make a substantially stiff hypotube are Stainless Steel 304, Nitinol etc. Hypotube 604 may be bent to a two-dimensional or three-dimensional shape. Distal tip of tubular element 602 may comprise a radio-opaque marker 606 e.g. a standard radio-opaque marker band. The proximal region of tubular element 602 comprises a threaded luer.

Figure 7A:
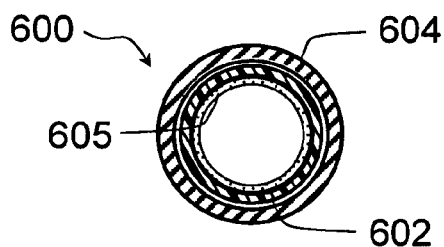
FIG. 7A shows a crossection of the guide catheter of FIG. 7 through plane 7A-7A.

FIG. 7A shows a crossectional view of guide catheter 600 of FIG. 7 through plane 7A-7A. The crossection of guide catheter 600 shows an outer hypotube 604 enclosing a tubular member 602 which in turn comprises a lubricious coating 605 located on the inner surface of tubular member 602.

Figure 8:
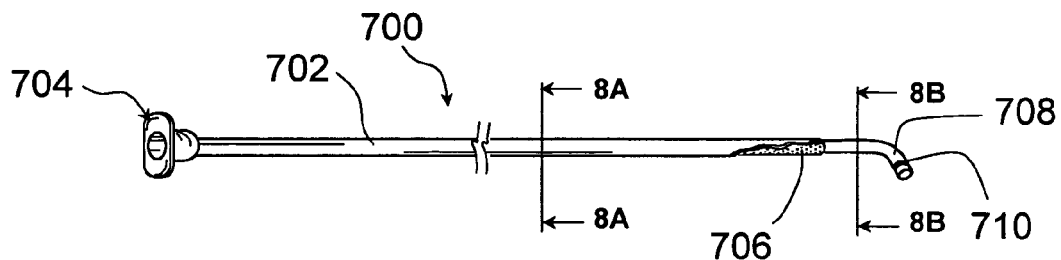
FIG. 8 shows perspective view of a second embodiment of a guide catheter comprising a straight hypotube.
Figure 8A:
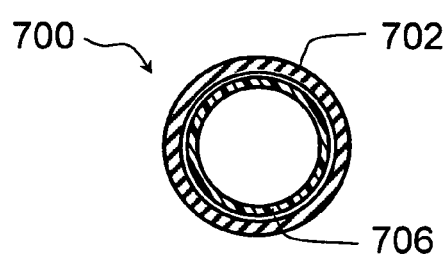
FIG. 8A shows a crossection of the guide catheter of FIG. 8 through plane 8A-8A.
Figure 8B:
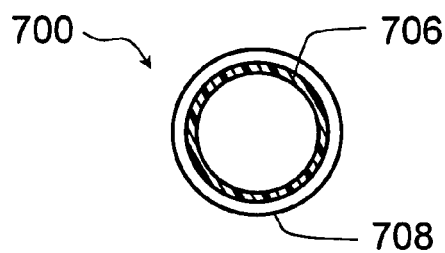
FIG. 8B shows a crossection of the guide catheter of FIG. 8 through plane 8B-8B.

FIG. 8 shows a perspective view of a second embodiment of a guide catheter comprising a straight hypotube. Guide catheter 700 comprises a hypotube 702. Proximal end of hypotube 702 may comprise a threaded luer 704. Hypotube 702 encloses a tubular liner 706 that protrudes from the distal end of hypotube 702. Suitable materials for constructing tubular liner 706 are PTFE, Nylon, PEEK etc. Distal region of tubular liner 706 is covered with a tubular element 708. Tubular element 708 may be constructed of suitable materials such as Pebax, HDPE, Nylon etc. and may comprise a braid. Proximal end of tubular element 708 may be bonded to distal end of hypotube 702 or may overlap distal region of hypotube 702. In one embodiment, distal region of tubular element 708 comprises a bent or angled region. In another embodiment, stiffness of tubular element 708 varies along the length of tubular element 708. Tubular element 708 may comprise a radio-opaque marker band 710 near distal end of tubular element 708. FIG. 8A shows a crossectional view of guide catheter 700 of FIG. 8 through plane 8A-8A showing hypotube 702 and tubular liner 706. FIG. 8B shows a crossectional view of guide catheter 700 of FIG. 8 through plane 8B-8B showing tubular element 708 and tubular liner 706.

Figure 8C:
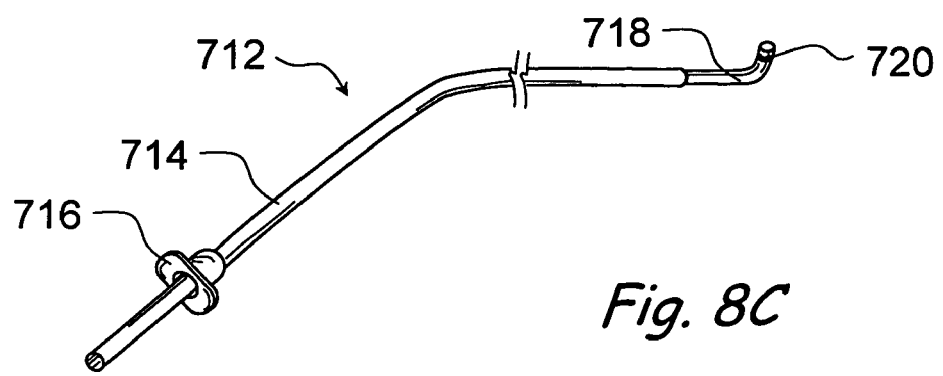
FIG. 8C shows a perspective view of an embodiment of a guide catheter comprising a curved or bent hypotube to facilitate access to the frontal sinuses.
Figure 8D:
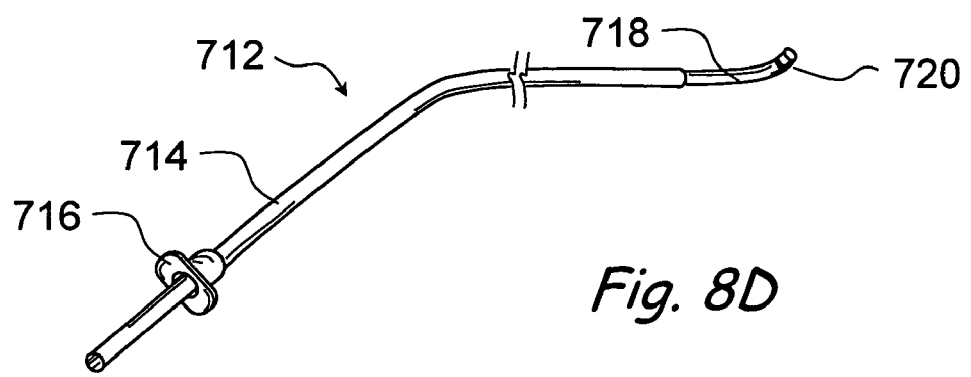
FIG. 8D shows a perspective view of a second embodiment of a guide catheter comprising a curved or bent hypotube to facilitate access to the sphenoid sinuses.
Figure 8:
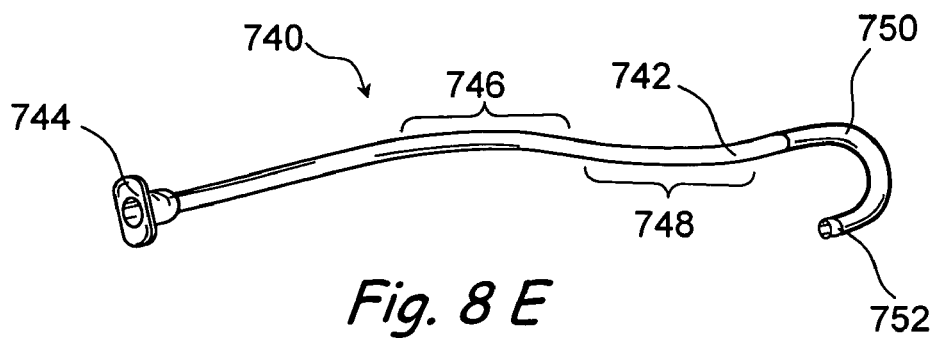
Figure 8:
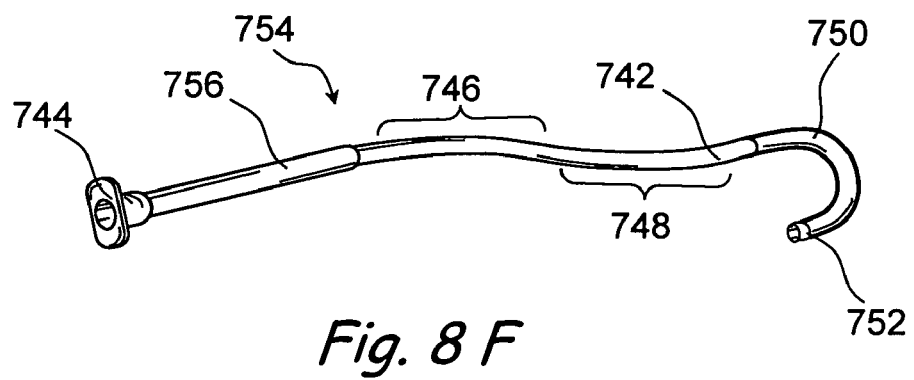
Figure 8:
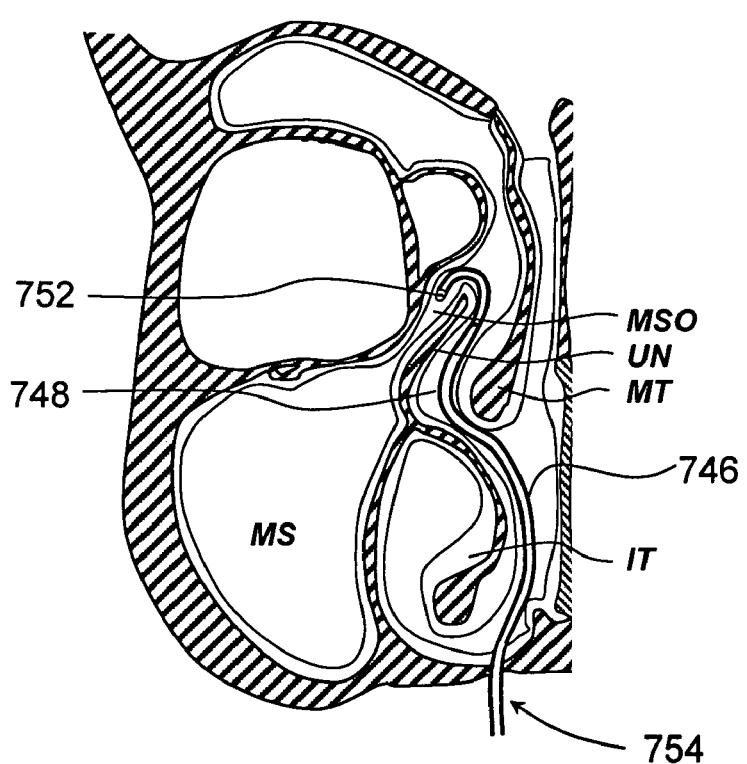
Figure 8:
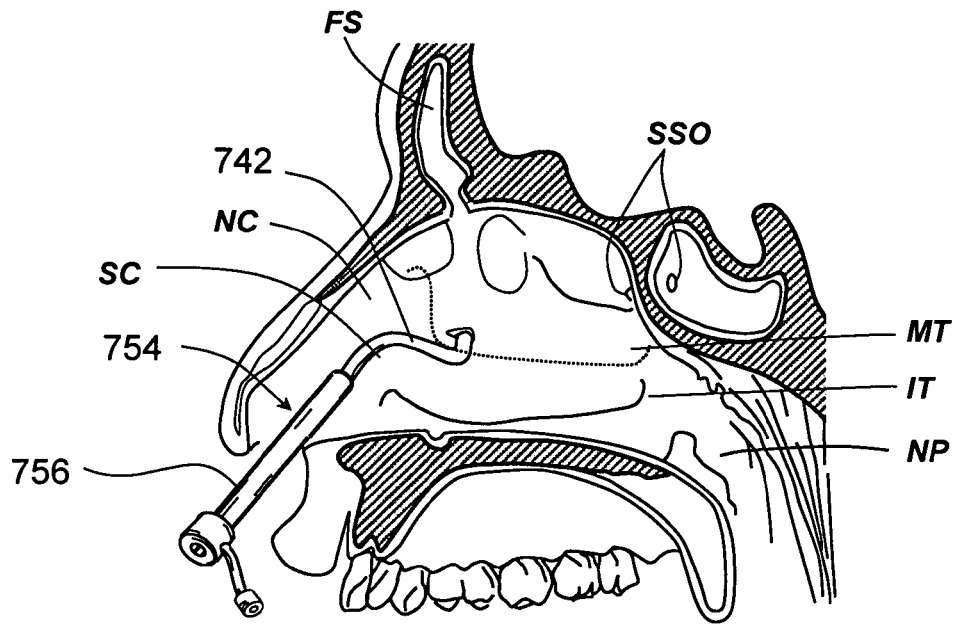
Figure 8:
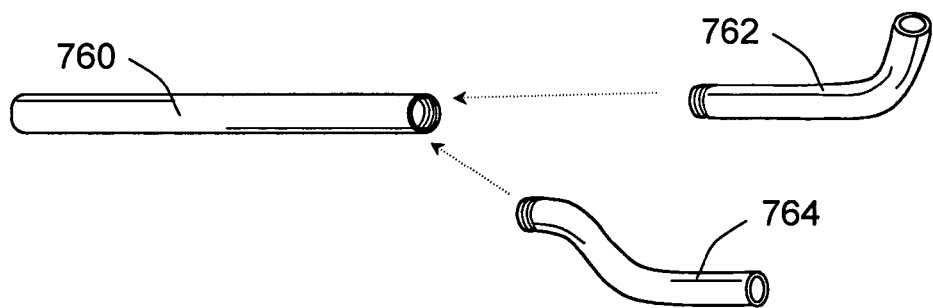

The hypotubes disclosed above may be malleable or non-malleable. They may also comprise one or more bent or angled regions. For example, FIG. 8C shows a perspective view of an embodiment of a guide catheter comprising a curved or bent hypotube to facilitate access to the frontal sinuses. Guide catheter 712 comprises a hypotube 714 comprising a threaded luer 716 at the proximal end of hypotube 714. Hypotube 714 may comprise one or more bent or angled regions. In this embodiment, the bent or angled region encloses an angle ranging from 60 degrees to 180 degrees. Hypotube 714 may be malleable or non-malleable. In this example, hypotube 714 encloses a tubular element 718. Tubular element 718 may be constructed of suitable materials such as Pebax, HDPE etc. The distal region of tubular element 718 comprises a bent or angled region. In this embodiment, the bent or angled region encloses an angle ranging from 60 degrees to 170 degrees to facilitate access to the frontal sinuses using guide catheter 712. Distal region of tubular element 718 may comprise a radio-opaque marker 720. FIG. 8D shows a perspective view of a second embodiment of a guide catheter comprising a curved or bent hypotube to facilitate access to the sphenoid sinuses. The catheter construction is similar to the catheter in FIG. 8C except the bent or angled region of hypotube 714 encloses an angle ranging from 90 degrees to 180 degrees and the bent or angled region of tubular element 718 encloses an angle ranging from 120 degrees to 180 degrees.

FIG. 8E shows a perspective view of an embodiment of a guide catheter comprising two bent or angled or curved regions to facilitate access to the maxillary sinuses. Guide catheter 740 comprises a tubular element 742 comprising a threaded luer 744 at the proximal end of tubular element 742. Tubular element 742 further comprises a proximal bent, curved or angled region 746 enclosing an angle ranging from 90 degrees to 180 degrees and a distal bent, curved or angled region 748 enclosing an angle ranging from 90 degrees to 180 degrees. Tubular element 742 can be constructed from a variety of biocompatible materials such as Pebax, HDPE, Nylon, PEEK etc. and may comprise a braid. The inner surface of tubular element 742 may comprise a lubricious layer e.g. a Teflon layer. A curved region 750 is attached to the distal end of tubular element 742. Curved region 750 may enclose an angle ranging from 75 degrees to 180 degrees. The stiffness of curved region 750 is more than the stiffness of tubular element 742 so that there is no significant change to the shape of curved region 750 during the operation of guide catheter 740. The distal end of curved region 750 comprises a soft, atraumatic tip 752. The distal end of curved region 750 may also comprise a radioopaque marker. Guide catheter 740 may be further bent out of plane to present a compound three-dimension end shape. FIG. 8F shows a perspective view of a second embodiment of a guide catheter comprising two bent or angled or curved regions and a hypotube to facilitate access to the maxillary sinuses. The construction of guide catheter 754 is similar to guide catheter 740 in FIG. 8E except that guide catheter 754 further comprises a hypotube 756 on the outer surface of the proximal region of guide catheter 754.

FIG. 8G shows a coronal section of the paranasal anatomy showing a method of accessing a maxillary sinus ostium using guide catheter 754 of FIG. 8F. Guide catheter 754 is introduced through a nostril and advanced in the paranasal anatomy such that atraumatic tip 752 is located inside or adjacent to a maxillary sinus ostium MSO. Proximal bent, curved or angled region 746 allows guide catheter 754 to be positioned around the inferior turbinate IT. Similarly, distal bent, curved or angled region 748 allows guide catheter 754 to be positioned around the middle turbinate MT. A guidewire or a suitable diagnostic or therapeutic device may then be introduced through the lumen of guide catheter 754 into the maxillary sinus MS. FIG. 8H shows a sagittal section of the paranasal anatomy showing the method of FIG. 8G to access a maxillary sinus ostium using guide catheter 754 of FIG. 8F.

FIG. 8I shows a perspective view of an example of a guide catheter comprising a common proximal portion and a plurality of detachable distal tips. Distal end of common proximal portion 760 attaches to proximal end of a first detachable tip 762 by an attachment mechanism. First detachable tip 762 comprises an angled, curved or bent region enclosing an angle of 80-110 degrees suitable for access to the frontal and ethmoid sinuses. Similarly, distal end of common proximal portion 760 attaches to proximal end of a second detachable tip 764 by an attachment mechanism. Second detachable tip comprises two angled, curved or bent regions enclosing angles of 80-110 degrees and 80-110 degrees respectively. Such a design is suitable for access to the maxillary sinuses. Examples of attachment mechanisms are screw mechanisms, snap fitting mechanisms, slide fit mechanisms etc. Distal end of first detachable tip 762 and second detachable tip 764 may comprise a radioopaque marker such as a radioopaque band. Such a design comprising detachable distal regions can be used in a variety of diagnostic or therapeutic devices discloses herein. It can be used for easy access to one or more anatomical regions in the ear, nose, throat or mouth by using multiple detachable distal tips, wherein each detachable tip is optimized for access to a particular anatomical region.

Figure 9:
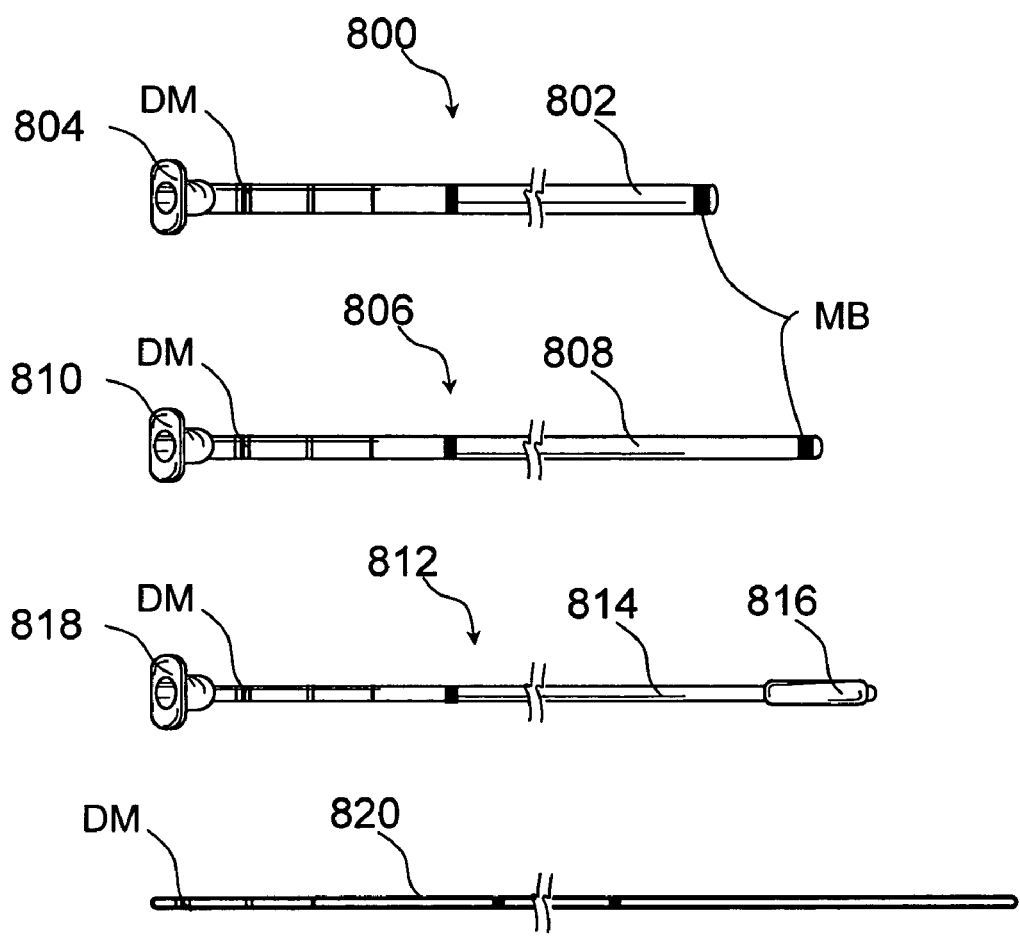
FIG. 9 shows a perspective view of a set of devices to dilate or modify ostia or other openings in the ear, nose, throat or mouth structures.

FIG. 9 shows a perspective view of a set of devices to dilate or modify ostia or other openings in the ear, nose, throat or mouth structures. Guide catheter 800 comprises a shaft 802 comprising a threaded luer 804 at proximal end of shaft 802. Distal end of shaft 802 comprises a radio-opaque marker band MB to enable the physician to identify the tip of shaft 802 in a fluoroscopic image. The distal end of shaft 802 may be substantially straight or may comprise one or more bent or angled regions. One or more distance markings DM may also be located on the shaft 802. An optional subselective catheter 806 may also be present in the set of devices. Subselective catheter 806 comprises a shaft 808 comprising a threaded luer 810 at the proximal end of shaft 808. Inner diameter of shaft 808 is smaller than inner diameter of shaft 802. Distal end of the shaft 808 comprises a radio-opaque marker band MB to enable the physician to identify the tip of shaft 808 in a fluoroscopic image. Distal end of shaft 808 may be substantially straight or may comprise one or more bent or angled regions. One or more distance markings DM may also be located on the shaft 808. Working device 812 comprises a shaft 814 comprising a working element 816 located on distal region of shaft 814 and a threaded luer 818 located on proximal end of shaft 814. In this example, the working element 816 is a dilating balloon. Other examples of working elements include dilating stents, suction or irrigation devices, needles, polypectomy tools, brushes, brushes, energy emitting devices such as ablation devices, laser devices, image-guided devices containing sensors or transmitters, endoscopes, tissue modifying devices such as cutters, biopsy devices, devices for injecting diagnostic or therapeutic agents, drug delivery devices such as substance eluting devices, substance delivery implants etc. The distal end of shaft 814 may be substantially straight or may comprise a bent or angled region. One or more distance markings DM may also be located on shaft 814. The set of devices further comprises a guidewire 820. Guidewire 820 may be substantially straight or may comprise a bent or angled region. One or more distance markings DM may also be located on guidewire 820. In one embodiment of a method using the abovementioned set of devices, guide catheter 800 is introduced into a patient's body so that distal end of guide catheter 800 is in the vicinity of an anatomical opening (e.g. an ostium) of an anatomical region (e.g. a paranasal sinus). Thereafter, guidewire 820 is introduced through guide catheter 800 into the anatomical region e.g. the paranasal sinus. If necessary, guide catheter 800 may be removed and the smaller subselective catheter 806 may be introduced over guide wire 820 into the paranasal sinus. Thereafter, working device 812 is introduced over guidewire 820 into the paranasal sinus and a diagnostic or therapeutic procedure is performed by working device 812. In another embodiment of a method using the abovementioned set of devices, subselective catheter 806 is introduced into a patients body so that distal end of subselective catheter 806 is in the vicinity of an anatomical opening (e.g. an ostium) of an anatomical region (e.g. a paranasal sinus). Thereafter, guidewire 820 is introduced through subselective catheter 806 into the anatomical region e.g. the paranasal sinus. Thereafter, subselective catheter 806 is removed. Larger guide catheter 800 is then introduced over guide wire 820. Working device 812 is then introduced over guidewire 820 into the paranasal sinus and a diagnostic or therapeutic procedure is performed by working device 812. This method embodiment enables a user to introduce larger working device 812 in the anatomical region.

Figure 10:
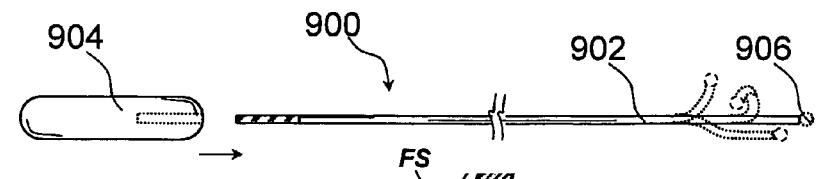
FIG. 10 shows a perspective view of a probing device.
Figure 10:
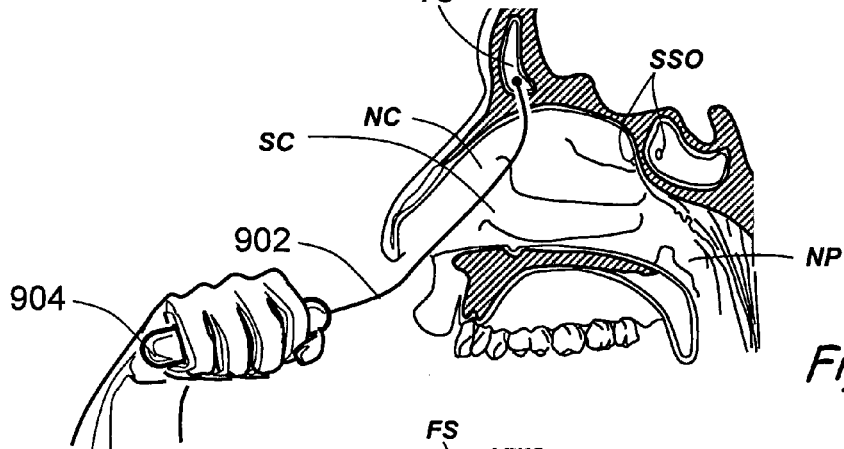
Figure 10:
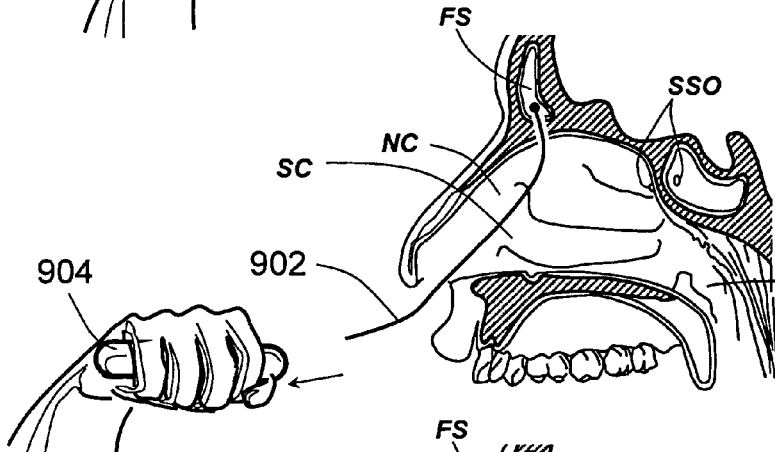
Figure 10:
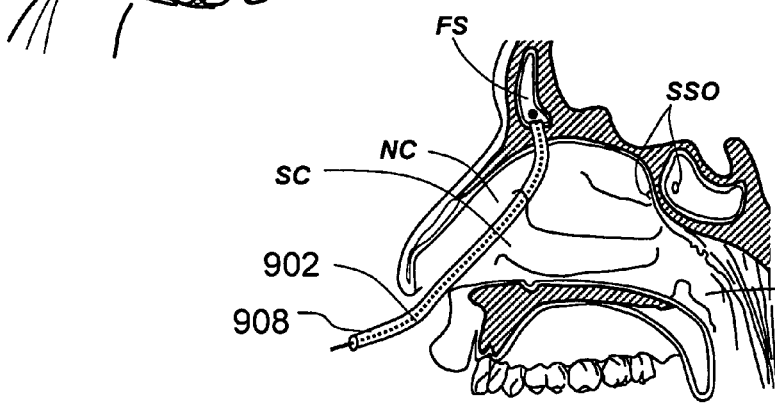

FIG. 10 shows a perspective view of a probing device. The probing device 900 comprises a probing element 902 and a detachable handle 904. Probing element 902 comprises an atraumatic tip 906 located on the distal end of probing element 902. In one embodiment, atraumatic tip 906 is spherical. Probing element 902 can be made from a variety of biocompatible materials such as metals (e.g. stainless steel, titanium, Nitinol etc.) or polymers (e.g. Pebax, polyethylene etc.). Probing element 902 may be rigid or flexible or malleable. In the embodiment shown in FIG. 10, the distal region of the probing element 902 is malleable. This enables a physician to adjust probing device 900 for a patient's unique anatomy. Probing element 902 may comprise one or more curved or angled regions. Length of probing element 902 can range from 10 centimeters to 30 centimeters. Detachable handle can be attached to the probing element 902 by a variety of attachment mechanisms including screw arrangement, clipping mechanism etc. The tip of the probing element may further be modified to include a marker, sensor or transmitter capable of being tracked using one or more imaging modalities, such as x-ray, electromagnetic, radio-frequency, ultrasound, radiation, optics, and/or similar modalities.

FIGS. 10A-10C show various steps of a method of using the probing device shown in FIG. 10 to access an anatomical region. In FIG. 10A, probing device 900 is advanced in to a patient's frontal sinus ostium through the nasal cavity. Atraumatic tip 906 prevents the probing device 900 from perforating and damaging healthy tissues. Thereafter, in FIG. 10B, detachable handle 904 is detached from probing element 902. Thereafter, in FIG. 10C, a working device 908 e.g. a catheter is advanced over the probing element 902 into the patient's frontal sinus ostium. Working device 908 can then be used to perform a diagnostic or therapeutic procedure or introduce other devices. In this example, probing device 900 was used to access the patient's frontal sinus ostium. Other anatomical locations in the patient's body e.g. ostia of other paranasal sinuses, ostia of lachrymal ducts, regions in the Eustachian tube, ducts of salvary glands, etc. may be accessed by similar methods. It is also possible that working device 908 may be preloaded over probing element 902 and maintained in a retracted position relative to the probing element until distal portion of the probing element 902 is introduced into a desired location. Further, multiple working devices may be inserted within working device 908 or over working device 908 once it is properly positioned.

Figure 11:
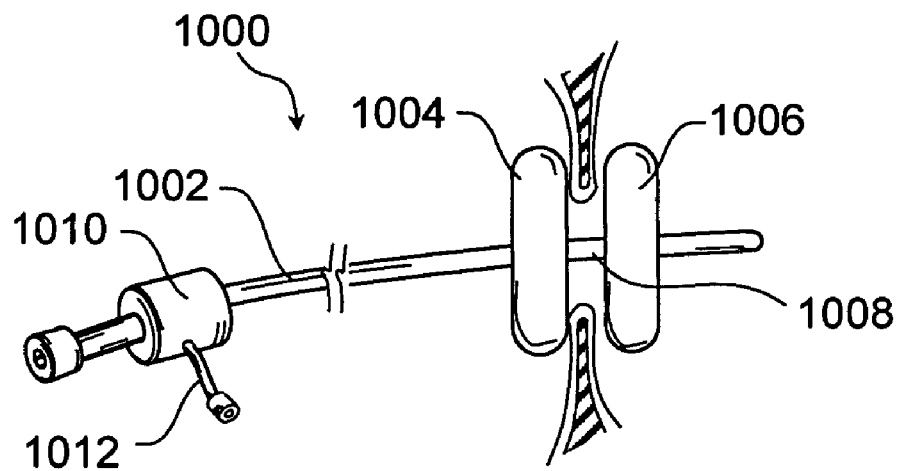
FIG. 11A shows a perspective view of a first embodiment of a dual balloon catheter that can be used to perform a diagnostic or therapeutic procedure.
FIG. 11B shows a perspective view of a second embodiment of a dual balloon catheter that can be used to perform a diagnostic or therapeutic procedure.
FIGS. 11C-11E show perspective views of third, fourth and fifth embodiments respectively of dual balloon catheters for dilating an anatomical region.
FIGS. 11F-11J show the various steps of a method of dilating an anatomical region using the catheter of FIG. 11D.
Figure 11:
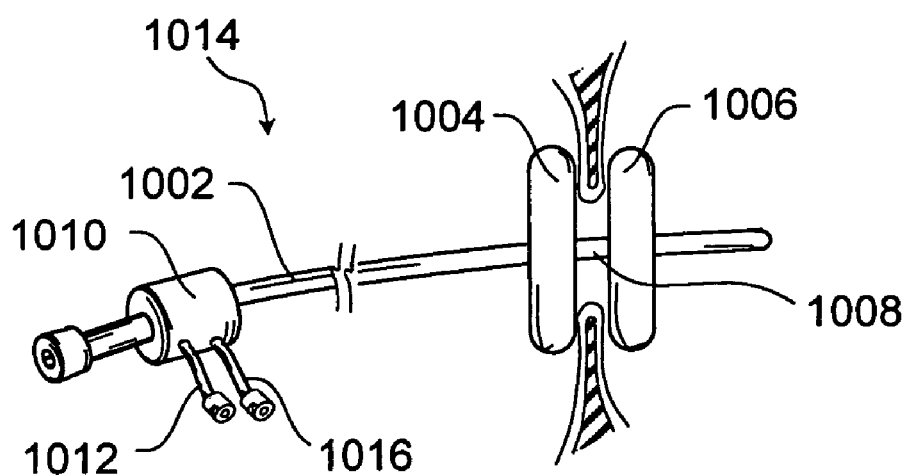
Figure 11:
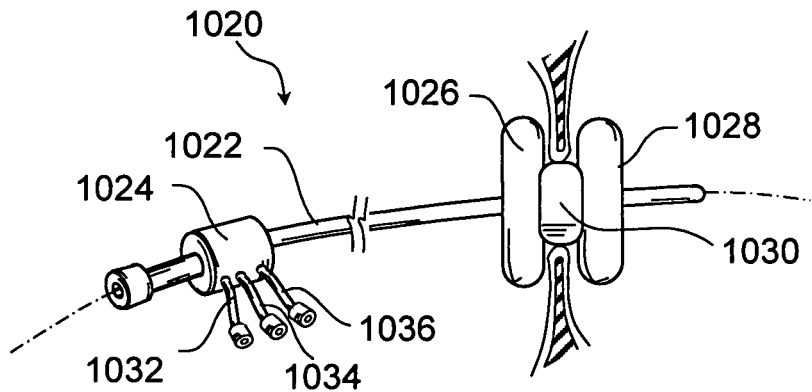
Figure 11:
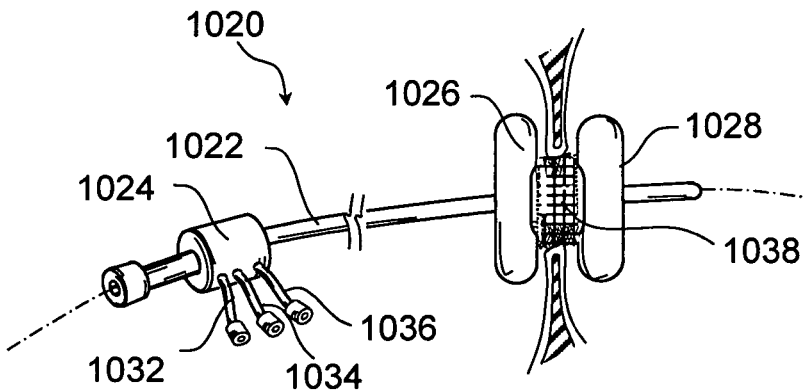
Figure 11:
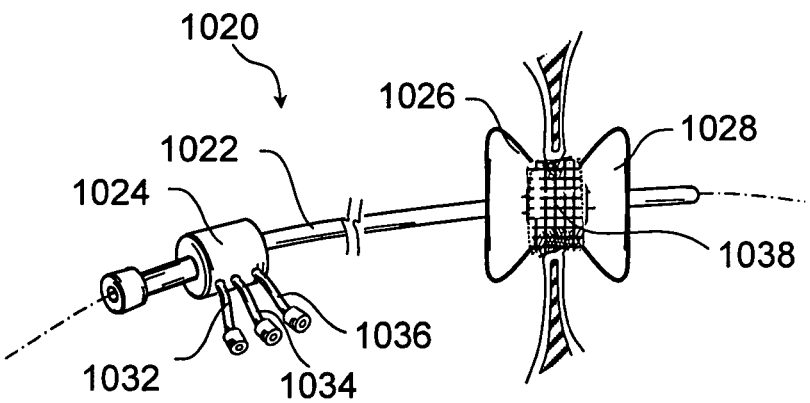
Figure 11:
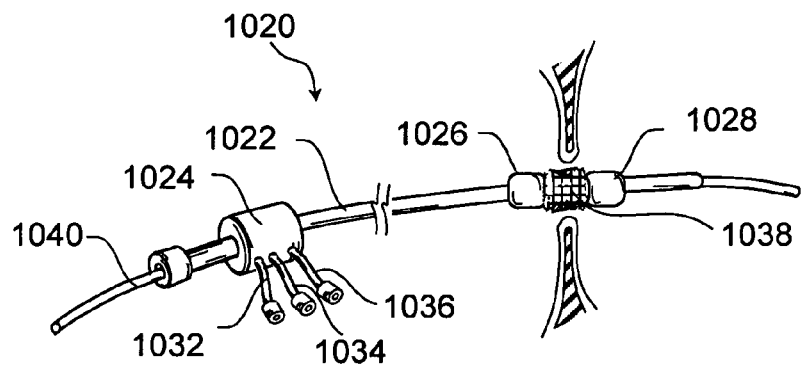
Figure 11:
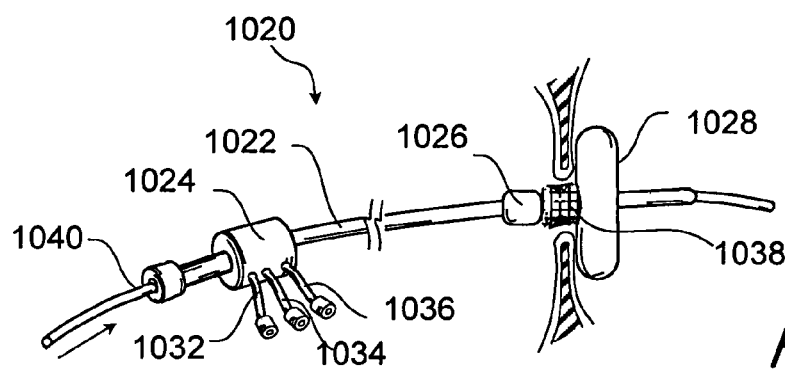
Figure 11:
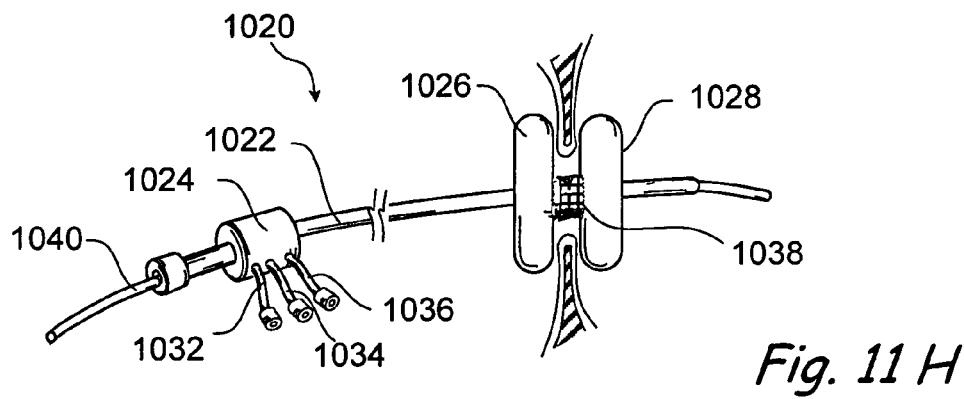
Figure 11:
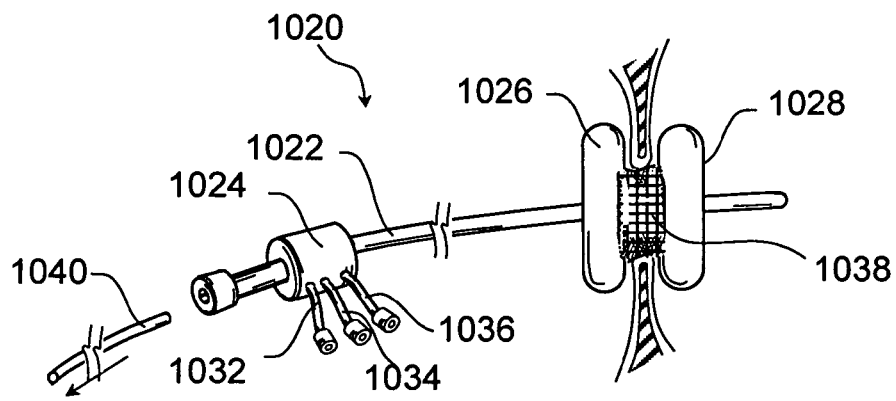
Figure 11:
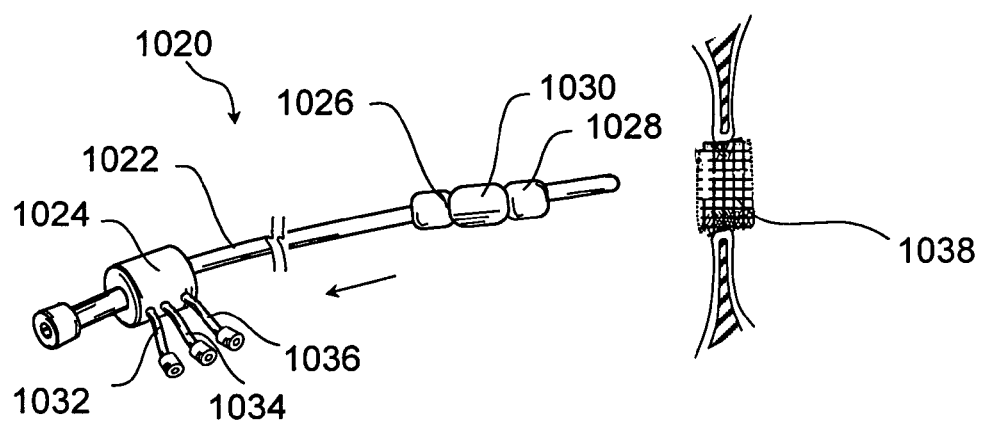

FIG. 11A shows a perspective view of a first embodiment of a dual balloon catheter that can be used to perform a diagnostic or therapeutic procedure. Catheter 1000 comprises a catheter shaft 1002 and a proximal balloon 1004 and a distal balloon 1006 located on catheter shaft 1002. A variety of diagnostic or therapeutic modules may be located in the inter-balloon region 1008 located between proximal balloon 1004 and distal balloon 1006. Examples of such diagnostic or therapeutic modules are dilating or occluding balloons, dilating stents, suction or irrigation devices, needles, polypectomy tools, energy emitting devices like ablation devices, laser devices, image-guided devices containing sensors or transmitters, imaging devices, endoscopes, tissue modifying devices like cutters, biopsy devices, devices for injecting diagnostic or therapeutic agents, lavage devices, drug delivery devices such as substance eluting devices, substance delivery implants etc. etc. A catheter hub 1010 is located on the proximal end of catheter shaft 1002. Catheter hub 1010 comprises a balloon inflation port 1012 that can be used to inflate both proximal balloon 1004 and distal balloon 1006.

FIG. 11B shows a perspective view of a second embodiment of a dual balloon catheter that can be used to perform a diagnostic or therapeutic procedure. The catheter 1014 shown in this embodiment further comprises a second balloon inflation port 1016. Balloon inflation port 1012 is used to inflate proximal balloon 1004 and second balloon inflation port 1016 is used to inflate distal balloon 1006. In one embodiment of a method using catheter 1014, distal balloon 1006 is inflated before proximal balloon 1004.

FIGS. 11C-11E show perspective views of third, fourth and fifth embodiments respectively of dual balloon catheters for dilating an anatomical region. In FIG. 11C, catheter 1020 comprises a catheter shaft 1022 comprising a catheter hub 1024 at the proximal end of catheter shaft 1022. The distal region of catheter shaft 1022 comprises a proximal balloon 1026 and a distal balloon 1028. Proximal balloon 1026 and distal balloon 1028 can be made from compliant or non-compliant materials. Catheter shaft 1022 further comprises a dilating balloon 1030 located between proximal balloon 1026 and distal balloon 1028. Dilating balloon 1030 is constructed from suitable non-compliant materials such as Polyethylene terephthalate etc. The balloons are inflated through three balloon inflation ports located on catheter hub 1024. A first balloon inflation port 1032 is used to inflate proximal balloon 1026, a second balloon inflation port 1034 is used to inflate distal balloon 1028 and a third balloon inflation port 1036 is used to inflate dilating balloon 1030. FIG. 11D shows a perspective view of catheter 1020 in FIG. 11C further comprising a stent 1038 disposed on dilating balloon 1030. Several types of stent designs can be used to construct stent 1038 such as metallic tube designs, polymeric tube designs, chain-linked designs, spiral designs, rolled sheet designs, single wire designs etc. These designs may have an open celled or closed celled structure. A variety of fabrication methods can be used for fabricating stent 1038 including but not limited to laser cutting a metal or polymer element, welding metal elements etc. A variety of materials can be used for fabricating stent 1038 including but not limited to metals, polymers, foam type materials, plastically deformable materials, super elastic materials etc. Some non-limiting examples of materials that can be used to construct stent 1038 are Nitinol, stainless steel, titanium, polyurethane, gelfilm, polyethylene and silicones e.g. silastic. A variety of features can be added to stent 1038 including but not limited to radiopaque coatings, drug elution mechanisms etc. FIG. 11E shows a perspective view of catheter 1020 in FIG. 11C wherein proximal balloon 1026 and distal balloon 1028 are conical. Dual balloon catheters may also be used to deploy self-expanding stents at a target anatomical region.

FIGS. 11F-11J show the various steps of a method of dilating an anatomical region using the catheter of FIG. 11D. In FIG. 11F, catheter 1020 is introduced into an anatomical region to be dilated. In one embodiment, catheter 1020 is introduced over a guidewire 1040. In FIG. 11G, distal balloon 1028 is inflated through second balloon inflation port 1034. Thereafter, catheter 1020 is pulled in the proximal direction till distal balloon 1028 gets lodged in the anatomical region to be dilated. Thereafter in FIG. 11H, proximal balloon 1026 is inflated through first balloon inflation port 1032. This enables catheter 1020 to be securely lodged in the anatomical region to be dilated. Thereafter in FIG. 11I, dilating balloon 1030 is inflated through third balloon inflation port 1036. Inflated dilation balloon 1030 exerts an outward force on the anatomical region and causes it to dilate. This step also deploys stent 1038. Thereafter in FIG. 11J, proximal balloon 1026, distal balloon 1028 and dilating balloon 1030 are deflated and catheter 1020 is removed by pulling catheter 1020 in the proximal direction.

Figure 12:
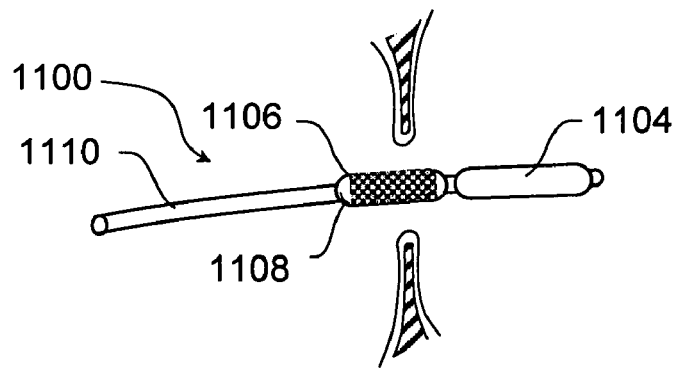
FIGS. 12A-12C show the various steps of a method of deploying a stent in the ear, nose, throat or mouth using a working catheter comprising a locating mechanism.
FIGS. 12D-12H show the various steps of a method of dilating an anatomical opening in the ear, nose, throat or mouth using a combination of a dilating device and an anchoring device.
Figure 12:
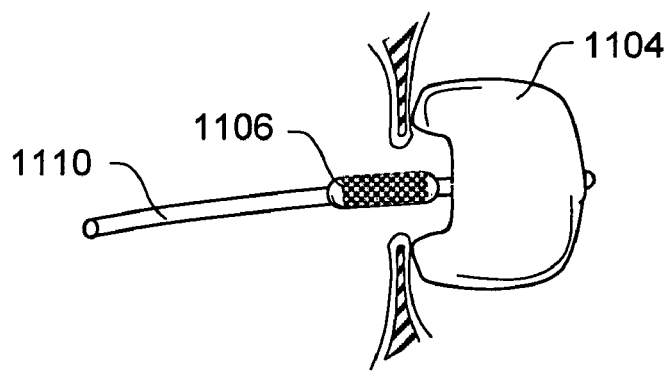
Figure 12:
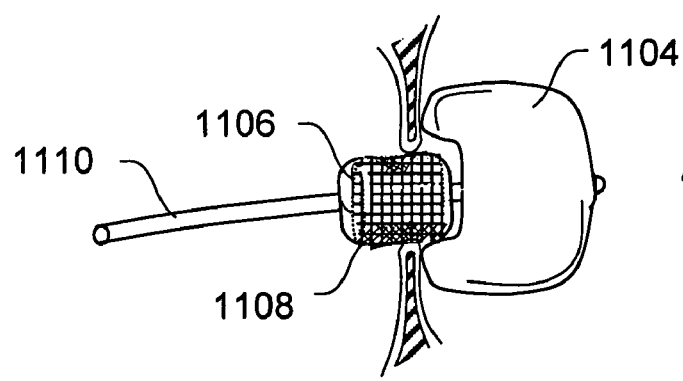
Figure 12:
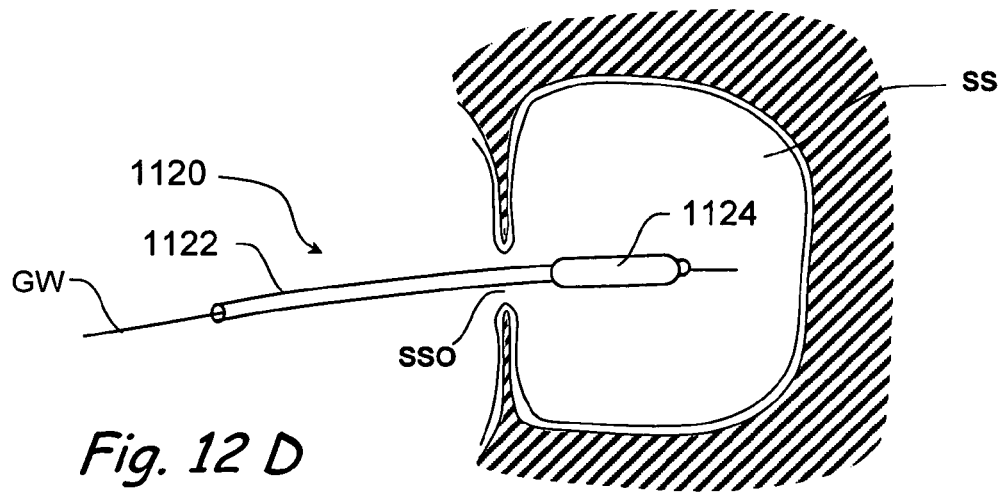
Figure 12:
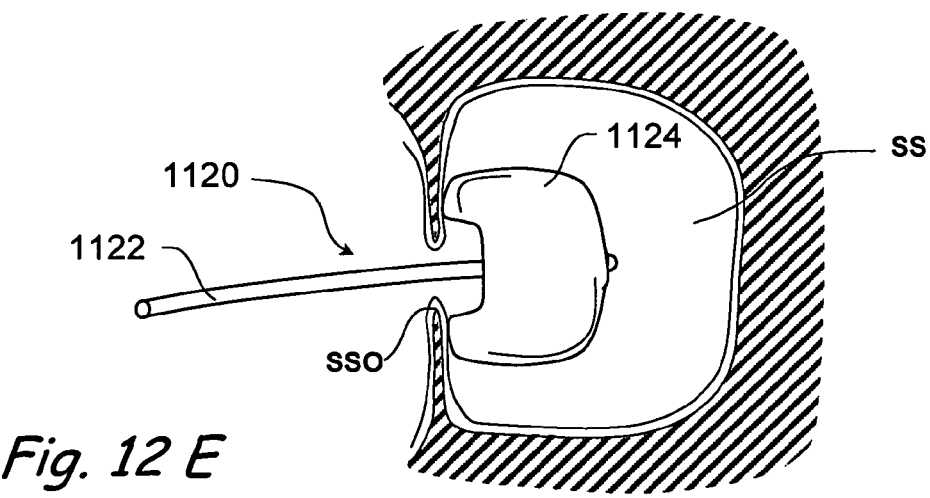
Figure 12:
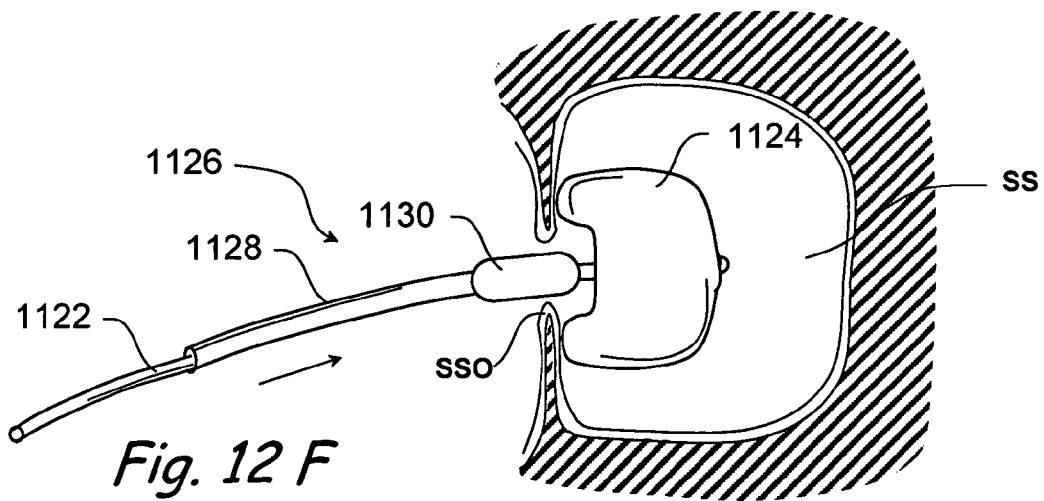
Figure 12:
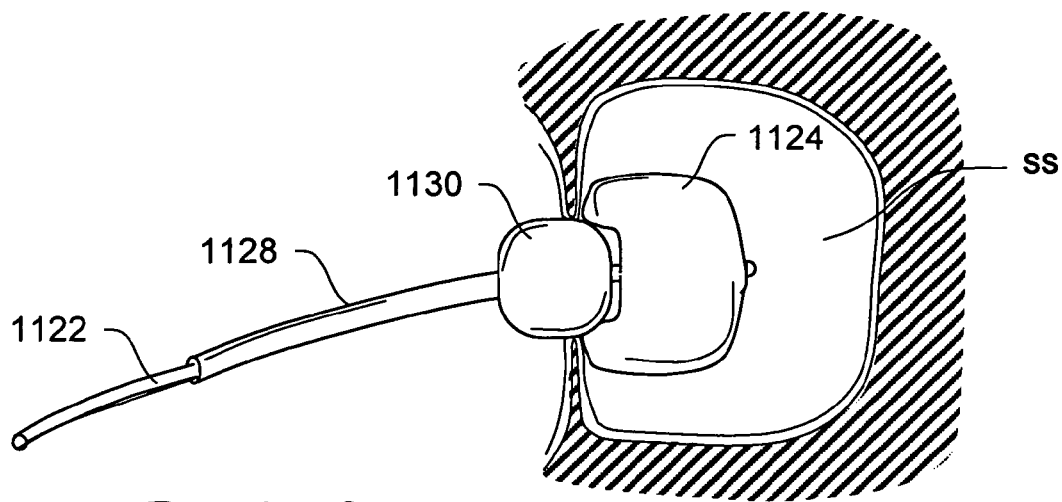
Figure 12:
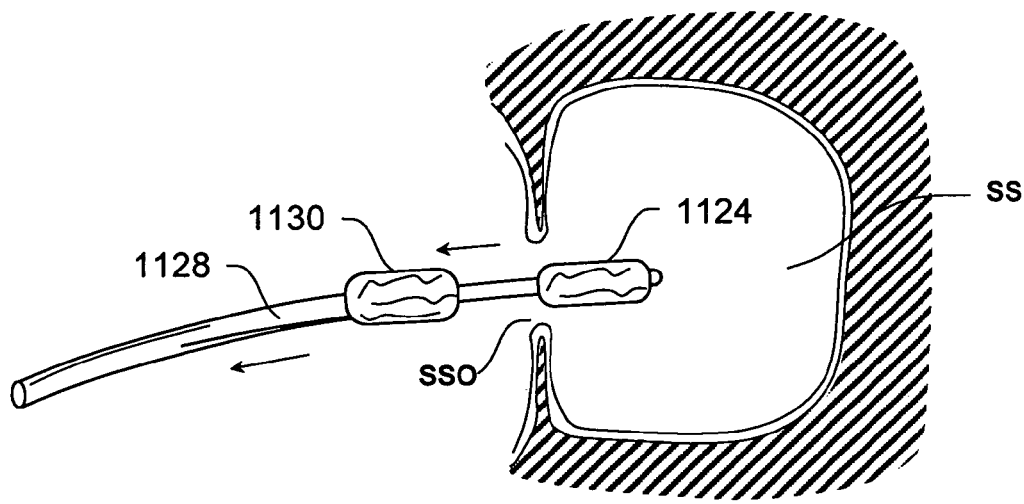

FIGS. 12A-12C show the various steps of a method of deploying a stent in the ear, nose, throat or mouth using a working catheter comprising a locating mechanism. In this example, the locating mechanism is a locator balloon. A working device 1100 is provided that comprises a locator balloon 1104 and a stent 1106 located on a stent deploying balloon 1108 located on a catheter shaft 1110. Locator balloon 1104 is located on the distal region of the catheter shaft 1110 and stent 1106 is located proximal to the locator balloon 1104. In FIG. 12A, the working device 1100 is inserted into an anatomical region through an anatomical opening 1111 such that the locator balloon 1104 is located distal to anatomical opening 1111. Examples of the anatomical region are paranasal sinuses, Eustachian tubes, lachrymal ducts and other structures in the ear, nose, throat or mouth etc. Examples of anatomical opening 1111 are ostia of paranasal sinuses, ostia of lachrymal ducts etc. In FIG. 12B, locator balloon 1104 is inflated. The inflated diameter of the locater balloon is greater than the diameter of the anatomical opening. Working device 1100 is then pulled in the proximal direction such that locator balloon 1104 presses against the anatomical opening 1111. This enables stent 1106 to be positioned accurately in a desired location relative to anatomical opening 1111. In FIG. 12C, stent deploying balloon 1108 is inflated to deploy stent 1106. Thereafter, stent deploying balloon 1108 and locator balloon 1104 are deflated and the working device 1100 is removed by pulling it out in the proximal direction. Similar working catheters comprising locating mechanisms can also be used to deploy self-expanding stents.

In this example, the locating mechanism was a locator balloon. Other examples of locating device are deployable elements such as wire meshes, radially projecting wires, deployable devices located on guidewires (e.g. balloons, wire meshes etc.), devices deployed on pull-elements (e.g. radially expandable elements etc.) etc.

FIGS. 12D-12H show the various steps of a method of dilating an anatomical opening in the ear, nose, throat or mouth using a combination of a dilating device and an anchoring device. In this example, the dilating device is a dilating balloon catheter and the anchoring device is an anchoring balloon catheter. In FIG. 12D, an anchoring balloon catheter 1120 comprising a catheter shaft 1122 and an anchoring balloon 1124 is inserted over a guidewire GW into an anatomical opening. In one embodiment, shaft 1122 of anchoring balloon catheter 1120 is coated with a lubricious coating such as Teflon. In this example the anatomical opening is the sphenoid sinus ostium SSO of a sphenoid sinus SS. In FIG. 12E, anchoring balloon 1124 is inflated. The inflated diameter of anchoring balloon 1124 is greater than the diameter of the anatomical opening. Thereafter, anchoring balloon catheter 1120 is pulled in the proximal direction so that anchoring balloon 1124 is anchored in the anatomical opening. In FIG. 12F, a dilating balloon catheter 1126 comprising a shaft 1128 and a dilating balloon 1130 is advanced in the proximal direction over shaft 1122 of anchoring balloon catheter 1120. Dilating balloon catheter 1126 is advanced till the distal portion of dilating balloon catheter 1126 touches anchoring balloon 1124. This design accurately positions dilating balloon 1130 in a target location in the anatomical opening. Thereafter, in FIG. 12G, dilating balloon 1130 is inflated to dilate the anatomical opening. Thereafter, in FIG. 12H, the dilating balloon 1130 and anchoring balloon 1124 are deflated and dilating balloon catheter 1126 and anchoring balloon catheter 1120 are withdrawn from the anatomical opening by pulling them in the proximal direction. Dilating balloon 1130 can be made of suitable non-compliant materials e.g. polyethylene terephthalate etc. Anchoring balloon 1124 can be made of suitable compliant materials e.g. polyurethane, silicone etc. or non-compliant materials e.g. polyethylene terephthalate etc. Examples of anchoring devices are catheters comprising balloons, deployable elements such as wire meshes, radially projecting wires; deployable devices located on guidewires (e.g. balloons, wire meshes etc.); devices deployed on pull-elements (e.g. radially expandable elements etc.) etc.

Such a combination of an anchoring device and a working device inserted along the anchoring device can be used for a variety of other methods and devices disclosed herein for treating anatomical openings such as ostia of paranasal sinuses, ostia of lachrymal ducts, ducts of salvary glands, Eustachian tubes and other ear, nose, throat or mouth structures etc.

Figure 13:
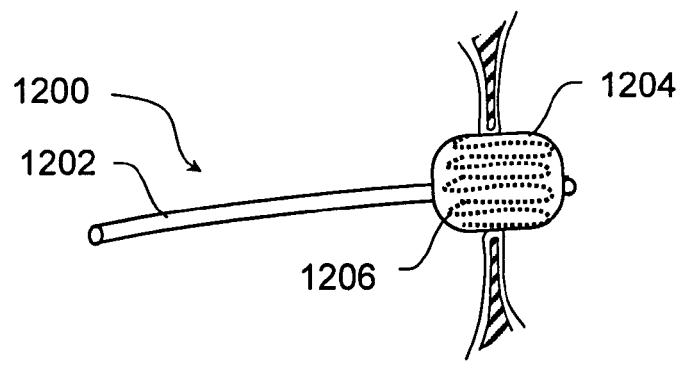
FIG. 13 shows a perspective view of a dilating device comprising an electrode element to reduce restenosis.

FIG. 13 shows a perspective view of a dilating device comprising an electrode element to reduce restenosis. Dilating device 1200 comprises a shaft 1202 and a dilating element 1204 located on the distal region of shaft 1202. Examples of dilating elements are non-compliant dilating balloons, mechanically expandable elements etc. Dilating device 1200 further comprises an electrode element 1206 located on dilating element 1204. Electrode element 1206 in combination with one or more surface electrodes attached to a surface of a patient's body delivers electrical energy to an anatomical region to be dilated. The electrical energy causes a controlled destruction of the adjacent anatomical region thereby reducing the risk to restenosis of the dilated region. Electrode element 1206 may have a variety of configurations including meshes, wires wound in a spiral configuration, wires wound in a sinusoidal configuration etc. Electrode element 1206 can be constructed from a variety of biocompatible metallic materials such as platinum-iridium alloys (e.g. 90% platinum/10% iridium) etc. Dilating device 1200 may further comprise an insulating layer between electrode element 1206 and dilating element 1204. In one embodiment, electrode element 1206 is located on a sheath that can be advanced over dilating device 1200 such that electrode element 1206 is located above dilating element 1204.

Figure 14:
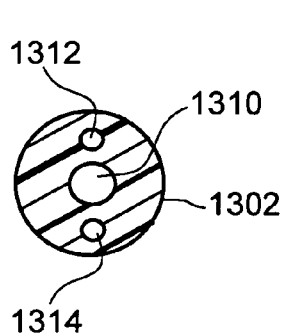
FIG. 14 shows a perspective view of an embodiment of a balloon catheter comprising a sizing balloon and a dilating balloon.
Figure 14:
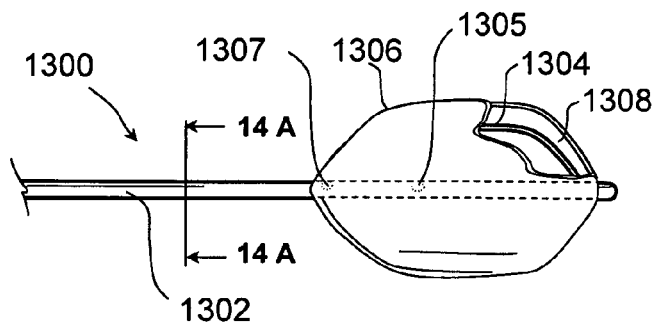
Figure 14:
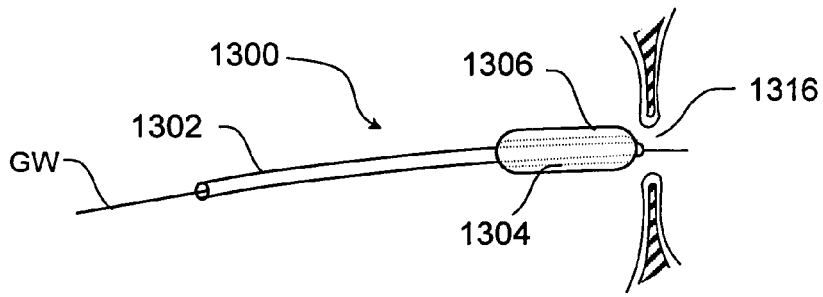
Figure 14:
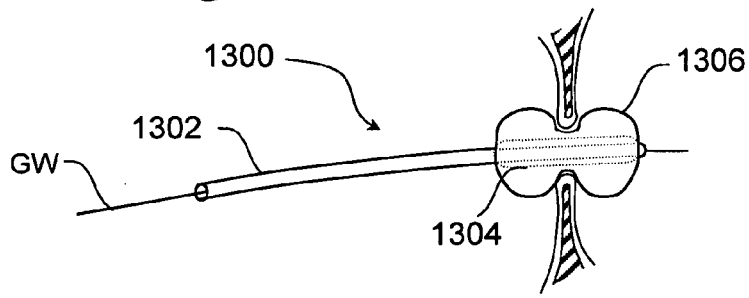
Figure 14:
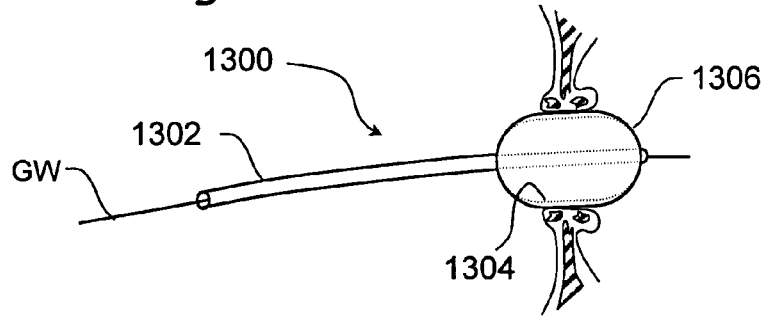

FIG. 14 shows a perspective view of an embodiment of a balloon catheter comprising a sizing balloon and a dilating balloon. A portion of the sizing balloon has been removed to show the dilating balloon underneath the sizing balloon. Balloon catheter 1300 comprises a shaft 1302 and a dilating balloon 1304 located on distal region of shaft 1302. Dilating balloon 1304 can be made of suitable non-compliant materials e.g. polyethylene terephthalate, Nylon etc. Dilating balloon 1304 is inflated through a first balloon inflation opening 1305. Balloon catheter 1300 further comprises a sizing balloon 1306 located around dilating balloon 1304. Sizing balloon 1306 is made from a compliant or semi-compliant material such as crosslinked polyethylene or other polyolefins, polyurethane, flexible polyvinylchloride, Nylon etc. Sizing balloon 1306 is inflated through a second balloon inflation opening 1307. Dilating balloon 1304 and sizing balloon 1306 enclose an inter-balloon volume 1308. FIG. 14A shows a crossection of the balloon catheter in FIG. 14 through plane 14A-14A. Shaft 1302 comprises a guidewire lumen 1310, a first inflation lumen 1312 that terminates distally in first balloon inflation opening 1305 of FIG. 14, and a second inflation lumen 1314 that terminates distally in second balloon inflation opening 1307 of FIG. 14.

FIGS. 14B-14D show the various steps of dilating an anatomical opening using the balloon catheter in FIG. 14. In FIG. 14B, balloon catheter 1300 is introduced over a guidewire GW into an anatomical opening 1316 to be dilated. Examples of the types of anatomical openings 1316 that may be dilated by this invention include ostia of paranasal sinuses, Eustachian tubes, ostia of lachrymal ducts, etc. Thereafter, in FIG. 14C, sizing balloon 1306 is inflated using an imageable inflating medium. Examples of suitable imageable inflating media are saline with a radioopaque contrast agent, carbon dioxide gas etc. Distal region of balloon catheter 1300 is subsequently imaged using a suitable imaging modality such as fluoroscopy or X-rays. This enables an operator to accurately estimate the size of anatomical opening 1316. Such a balloon catheter is also suited for estimating the diameter of the narrowest region in a tubular anatomical region e.g. a Eustachian tube prior to performing a diagnostic or therapeutic procedure such as balloon dilation. On the basis of information obtained during step 14C, balloon catheter 1300 may be repositioned and step 14C repeated if necessary. Thereafter, in step 14D, sizing balloon 1306 is deflated. Also in step 14D, dilating balloon 1304 is inflated to dilate a target region in anatomical opening 1316. Thereafter, dilating balloon 1304 is deflated and balloon catheter 1300 is withdrawn from anatomical opening 1316. In one embodiment, sizing balloon 1306 may be reinflated after a balloon dilation procedure to obtain feedback about the performance of the balloon dilation procedure.

FIG. 15 shows a perspective view of a balloon catheter 1400 for delivering diagnostic or therapeutic agents. This balloon catheter 1400 comprises a catheter shaft 1402 which may be flexible, malleable or rigid, and a dilating balloon 1404 located on the distal region of shaft 1402. Dilating balloon 1404 can be made of any suitable compliant or non-compliant materials (e.g. polyethylene terephthalate etc.). An outer balloon or sheath 1406 covers the dilating balloon 1404, as shown in the cut-away view of FIG. 15. Sheath 1406 can be made of suitable non-compliant materials e.g. polyethylene terephthalate etc. or compliant or semi-compliant materials such as crosslinked polyethylene or other polyolefins, polyurethane, flexible polyvinylchloride, Nylon etc. Sheath 1406 comprises one or more pores 1408 through which diagnostic or therapeutic agents can be delivered to the surrounding anatomy. Pores 1408 may have a pore size ranging from sub-micron to a few microns. Dilating balloon 1404 is inflated by a balloon inflation lumen 1410. The diagnostic or therapeutic agents can be delivered to the region between sheath 1406 and dilating balloon 1404 by an agent delivery lumen 1412. In this particular embodiment, sheath 1406 is attached to shaft 1402. FIG. 15A shows a crossection through the plane 15A-15A of FIG. 15 showing shaft 1402 comprising balloon inflation lumen 1410, agent delivery lumen 1412 and a guidewire lumen 1414.

FIG. 16 shows a perspective view of a balloon catheter comprising one or more agent delivery reservoirs. Balloon catheter 1500 comprises a shaft 1502 and a balloon 1504 located on the distal region of shaft 1502. Balloon 1504 may be made from suitable compliant or semi-compliant material such as crosslinked polyethylene or other polyolefins, polyurethane, flexible polyvinylchloride, Nylon, etc., or from non-compliant materials such as polyurethane, etc. Balloon catheter 1500 further comprises one or more agent delivery reservoirs 1506 located on balloon 1504. Agent delivery reservoirs 1506 contain one or more diagnostic or therapeutic agents absorbed in a matrix. Examples of diagnostic or therapeutic agents are contrast agents, pharmaceutically acceptable salt or dosage form of an antimicrobial agent (e.g., antibiotic, antiviral, anti-parasitic, antifungal, etc.), a corticosteroid or other anti-inflammatory (e.g., an NSAID), a decongestant (e.g., vasoconstrictor), a mucous thinning agent (e.g., an expectorant or mucolytic), an anesthetic agent with or without vasoconstrictor (e.g., Xylocaine with or without epinephrine, Tetracaine with or without epinephrine), an analgesic agent, an agent that prevents of modifies an allergic response (e.g., an antihistamine, cytokine inhibitor, leucotriene inhibitor, IgE inhibitor, immunomodulator), an allergen or another substance that causes secretion of mucous by tissues, anti-proliferative agents, hemostatic agents to stop bleeding, cytotoxic agents e.g. alcohol, biological agents such as protein molecules, stem cells, genes or gene therapy preparations etc. When balloon 1504 is inflated to dilate an anatomical region, it exerts pressure on agent delivery reservoirs 1506. This pressure squeezes out the one or more diagnostic or therapeutic agents absorbed in the matrix and causes them to be released into the anatomical region. In one embodiment, agent delivery reservoirs 1506 comprise diagnostic or therapeutic agents absorbed in a porous matrix formed of a porous material such as a flexible or rigid polymer foam, cotton wadding, gauze, etc. Examples of biodegradable polymers that may be foamed or otherwise rendered porous include polyglycolide, poly-L-lactide, poly-D-lactide, poly (amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. Examples of non-biodegradable polymers that may be foamed or otherwise rendered porous include polyurethane, polycarbonate, silicone elastomers etc. FIG. 16A shows a crossection view through plane 16A-16A of FIG. 16 showing shaft 1502 comprising a balloon inflation lumen 1508 and a guidewire lumen 1510.

FIG. 17 shows a perspective view of a balloon catheter comprising a balloon comprising one or more micropores or openings. Balloon catheter 1600 comprises a shaft 1602 comprising a dilating balloon 1604 located on the distal region of shaft 1602. Dilating balloon 1604 can be made of suitable non-compliant materials e.g. polyethylene terephthalate etc. Dilating balloon 1604 comprises one or more micropores 1606 of a pore size ranging from submicron (e.g. 0.5 micron) to a few microns. Micropores 1606 can be formed on material of dilating balloon 1604 by various processes including mechanical punching, mechanical drilling, irradiation e.g. directing a laser beam or an ion or electron beam at the balloon material etc. Dilating balloon 1604 is inflated using an inflating medium comprising one or more diagnostic or therapeutic agents to be delivered to a target anatomical region such as ostia of paranasal sinuses, ostia of lachrymal ducts, ducts of salvary glands, Eustachian tubes etc. Examples of diagnostic or therapeutic agents are contrast agents, pharmaceutically acceptable salt or dosage form of an antimicrobial agent (e.g., antibiotic, antiviral, anti-parasitic, antifungal, etc.), an anesthetic agent, an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), an allergen or another substance that causes secretion of mucous by tissues, anti-proliferative agents, hemostatic agents to stop bleeding, cytotoxic agents e.g. alcohol, biological agents such as protein molecules, stem cells, genes or gene therapy preparations etc. When dilating balloon 1604 is inflated, a portion of the inflating medium seeps out of dilating balloon 1604 through micropores 1606 and thus is delivered to the adjacent anatomical regions. Thus dilation and agent delivery can be achieved in a single step. FIG. 17A shows a crossectional view through the plane 17A-17A of FIG. 17 showing shaft 1602 comprising a guidewire lumen 1608 and a balloon inflation lumen 1610.

Figure 18:
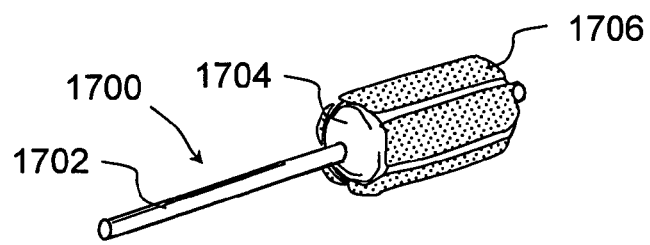
FIG. 18 shows a balloon catheter comprising a balloon having an outer coating of diagnostic or therapeutic agents.
Figure 18:
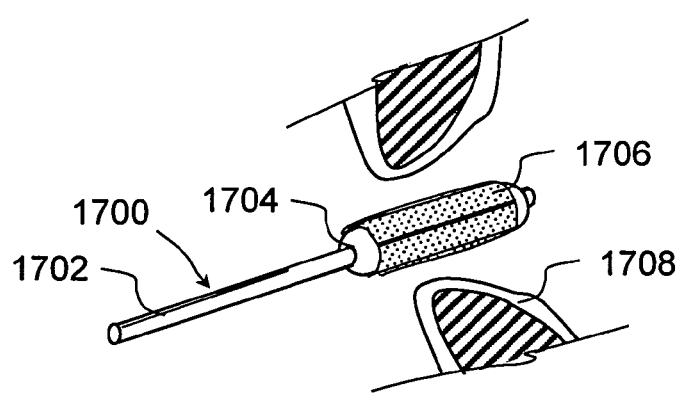
Figure 18:
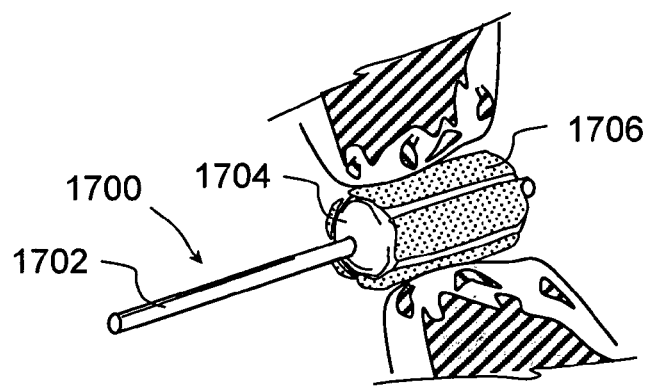
Figure 18:
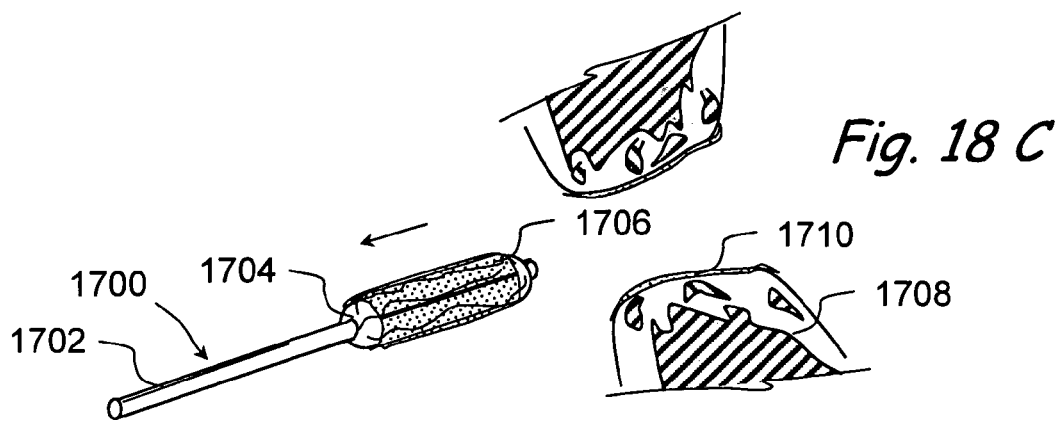

FIG. 18 shows a balloon catheter comprising a balloon having an outer coating of diagnostic or therapeutic agents. Balloon catheter 1700 comprises a shaft 1702 and a dilating balloon 1704 located on the distal region of shaft 1702. Dilating balloon 1704 can be made of suitable non-compliant materials e.g. polyethylene terephthalate etc. Dilating balloon 1704 comprises a coating 1706 of one or more diagnostic or therapeutic agents on the outer surface of dilating balloon 1704. Coating 1706 may comprise diagnostic or therapeutic agents located in a suitable carrier medium. In one embodiment, the carrier medium is a hydrogel. In another embodiment, the carrier medium is a solid having the consistency of wax e.g. sterile bone wax. In another embodiment, the carrier containing the agents can be deposited on the outer surface of dilating balloon 1704 just before balloon catheter 1700 is used for performing a diagnostic or therapeutic procedure. Coating 1706 may be present on the surface of dilating balloon 1704 in a variety of configurations. In one embodiment, coating 1706 is in the form of parallel strips of a carrier medium comprising one or more diagnostic or therapeutic agents. The coating may also be in the form of an annular layer, a plurality of discrete spots etc. When dilating balloon 1704 is inflated to dilate an anatomical region, coating 1706 comes into contact with the adjacent anatomical region. A portion of coating 1706 is deposited on the adjacent anatomical region which delivers the diagnostic or therapeutic agents to the adjacent anatomical region. Thus dilation and agent delivery can be achieved in a single step. In one embodiment, coating 1706 comprises a hemostatic material with a consistency of bone-wax.

FIGS. 18A-18C show the steps of a method of using the balloon catheter of FIG. 18 to dilate an anatomical region. In FIG. 18A, balloon catheter 1700 is introduced in an anatomical region 1708. Balloon catheter 1700 is positioned such dilating balloon 1704 is located in the target region to be dilated. Thereafter, in FIG. 18B, dilating balloon 1704 is inflated. This dilates anatomical region 1708 and deposits a portion of coating 1706 on the dilated region. Thereafter, in FIG. 18C, dilating balloon 1704 is deflated and balloon catheter 1700 is withdrawn from anatomical region 1708 leaving behind a deposited layer 1710 of coating 1706 on the dilated anatomical region 1708.

Figure 19:
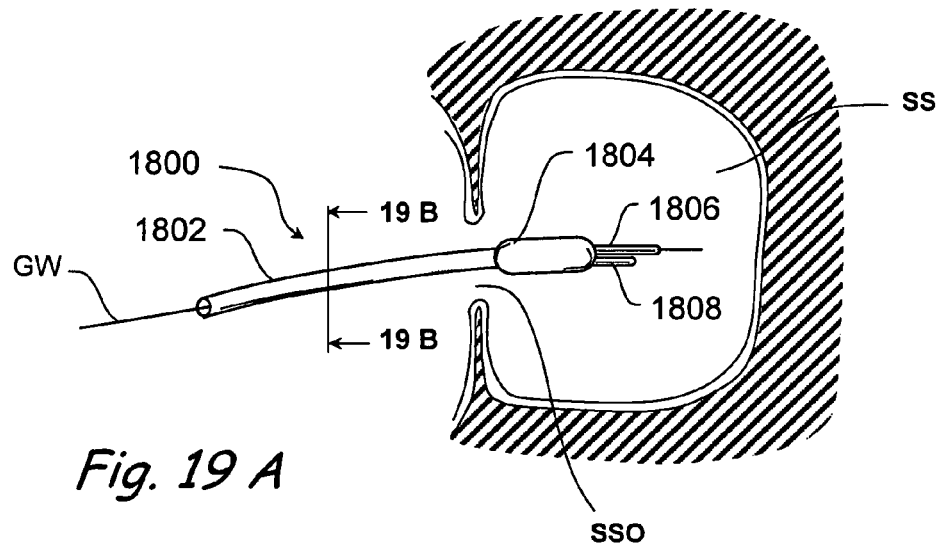
FIG. 19A shows a perspective view of a lavage catheter.
FIG. 19B shows a crossectional view through the plane 19B-19B of FIG. 19A.
FIG. 19C shows the method of operation of lavage catheter of FIG. 19A to lavage an anatomical region.
Figure 19:
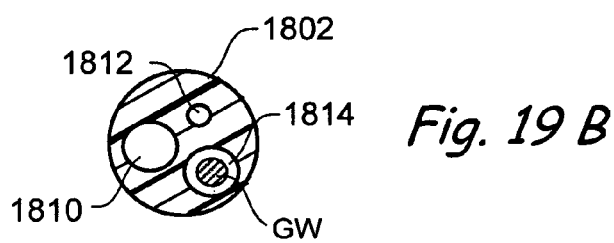
Figure 19:
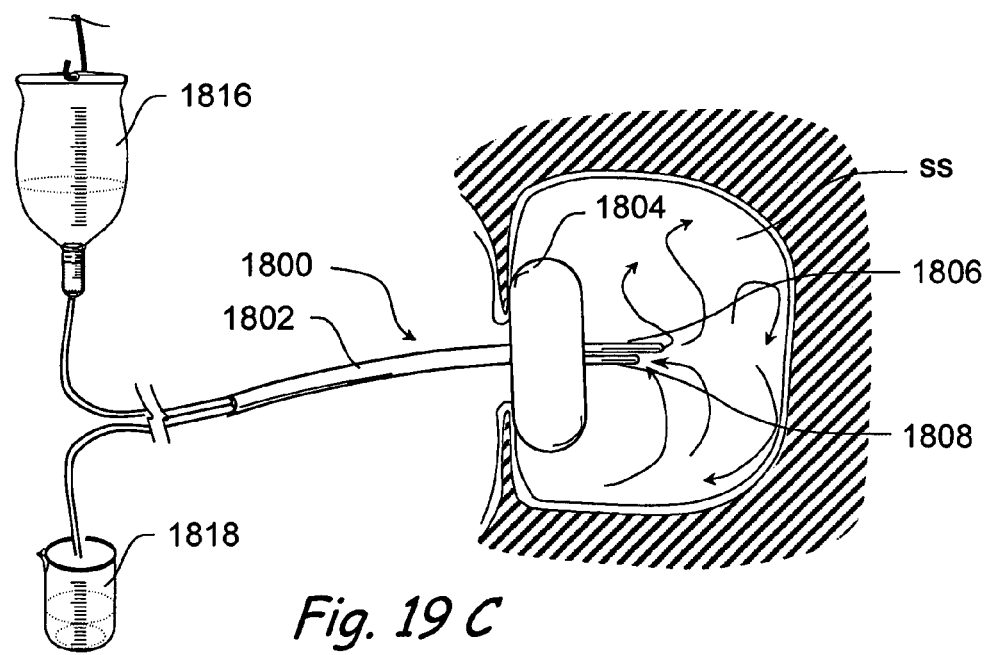

FIG. 19A shows a perspective view of a lavage catheter. Lavage catheter 1800 comprises a shaft 1802 and an occluding balloon 1804 located on the distal region of shaft 1802. Occluding balloon 1804 can be made of suitable compliant materials e.g. polyurethane, silicone etc. or non-compliant materials e.g. polyethylene terephthalate etc. Lavage catheter 1800 further comprises a flushing tip 1806 and an aspiration tip 1808 located on the distal end of shaft 1802. In FIG. 19A, lavage catheter 1800 is introduced over a guidewire GW into an anatomical region e.g. a sphenoid sinus SS through an anatomical opening e.g. a sphenoid sinus ostium SSO. FIG. 19B shows a crossectional view through the plane 19B-19B of FIG. 19A. Shaft 1802 comprises an aspiration lumen 1810, a flushing lumen 1812 and a guidewire lumen 1814. Distal end of aspiration lumen 1810 opens at the distal end of aspiration tip 1808 and distal end of flushing lumen 1812 opens at the distal end of flushing tip 1806.

FIG. 19C shows the method of operation of lavage catheter 1800 of FIG. 19A to lavage an anatomical region. In FIG. 19C, occluding balloon 1804 is inflated and lavage catheter 1800 is pulled in the proximal direction till occluding balloon occludes the anatomical opening e.g. sphenoid sinus ostium SSO. Thereafter, a flushing medium introduced in the anatomical region through flushing tip 1806. The flushing medium may be introduced in lavage catheter 1800 from a flushing medium container 1816 e.g. a saline bag connected to the proximal region of lavage catheter 1800. The flushing medium is aspirated from the anatomical region through aspiration tip 1808. The proximal end of lavage catheter 1800 may be connected to a collection vessel 1818 to collect the aspirated flushing medium. In one embodiment, collection vessel 1818 is further connected to wall suction.

Figure 20:
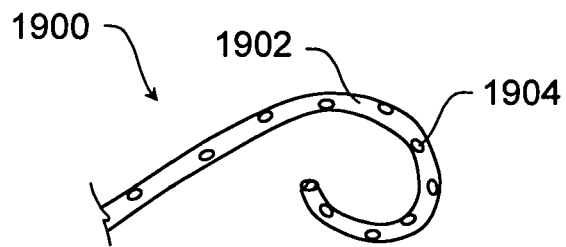
FIG. 20A shows a perspective view of the distal end of a second embodiment of a lavage catheter.
FIG. 20B shows a perspective view of the distal end of the lavage catheter of FIG. 20A introduced in an anatomical region.
FIG. 20C shows an embodiment of the lavage cattheter of FIG. 20A being used to lavage an anatomical region.
FIG. 20D shows a sagittal section of a human head showing the general working environment of the lavage devices of FIGS. 20A-20C.
Figure 20:
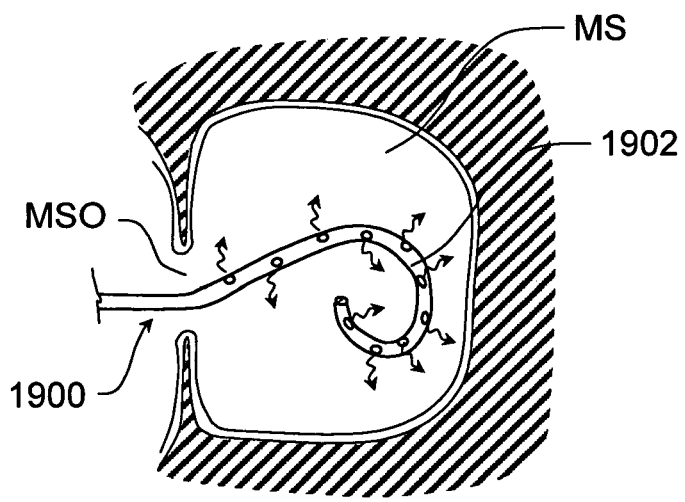
Figure 20:
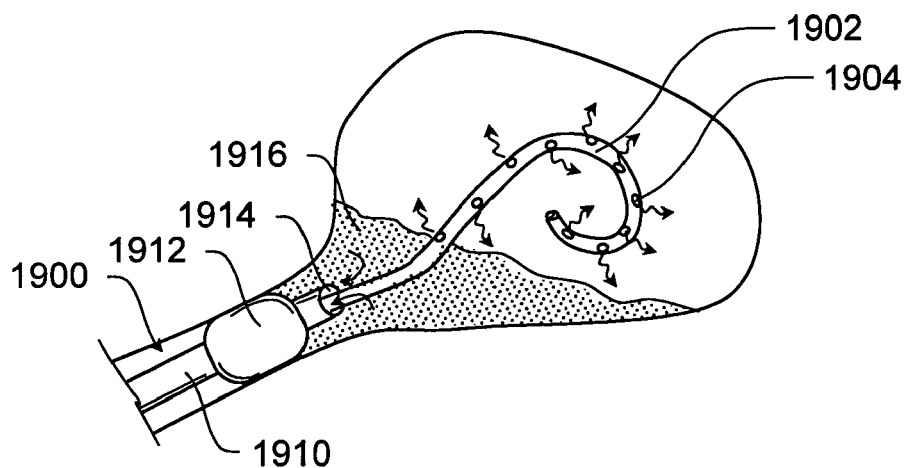
Figure 20:
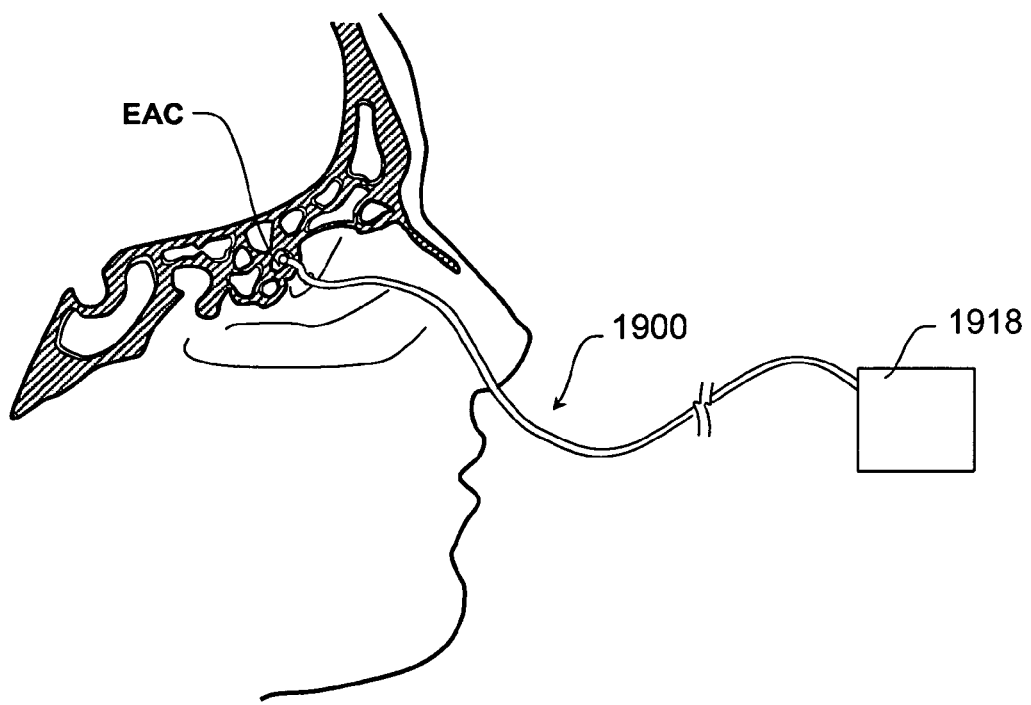

FIG. 20A shows a perspective view of the distal end of a second embodiment of a lavage catheter. Lavage catheter 1900 comprises a tubular member 1902 comprising a one or more openings 1904 located on the distal region of tubular member 1902. Tubular member 1902 may be made from a variety of materials such as silicone elastomers, Pebax, HDPE etc. Distal region of tubular member 1902 may comprise a curved or bent region. Tubular member 1902 comprises a first lumen connected to openings 1904. Suitable diagnostic or therapeutic fluids can be introduced or removed through openings 1904. Examples of such fluids are saline, pharmaceutically acceptable salt or dosage form of an antimicrobial agent (e.g., antibiotic, antiviral, anti-parasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), an allergen or another substance that causes secretion of mucous by tissues, a contrast agent, an anesthetic agent with or without vasoconstrictor (e.g., Xylocaine with or without epinephrine, Tetracaine with or without epinephrine), an analgesic agent, hemostatic agents to stop bleeding, anti-proliferative agents, cytotoxic agents e.g. alcohol, biological agents such as protein molecules, stem cells, genes or gene therapy preparations etc. In one embodiment, tubular member 1902 comprises a second lumen that acts as a guidewire lumen.

FIG. 20B shows a perspective view of the distal end of the lavage catheter of FIG. 20A introduced in an anatomical region. In this example, the anatomical region is a maxillary sinus MS comprising a maxillary sinus ostium MSO. Lavage catheter 1900 may be introduced into the anatomical region by an over-the-wire method, through a cannula, or by a variety of methods disclosed in this patent application and in the patents documents incorporated herein by reference. Other examples of anatomical regions that can be treated using lavage catheter 1900 are other paranasal sinuses, lachrymal ducts, Eustachian tubes, and other hollow organs in the ear, nose, throat or mouth.

FIG. 20C shows an embodiment of the lavage catheter of FIG. 20A being used to lavage an anatomical region. In this embodiment, lavage catheter 1900 further comprises an outer sheath 1910 comprising an occluding balloon 1912 located on the distal region of outer sheath 1910. Occluding balloon 1912 may be made from suitable compliant or semi-compliant material such as crosslinked polyethylene or other polyolefins, polyurethane, flexible polyvinylchloride, Nylon etc. or from non-compliant materials such as polyurethane etc. Outer sheath 1910 covers tubular member 1902 such that outer sheath and tubular member 1902 enclose a suction lumen 1914 between them. Tubular member 1902 is used to introduce a lavage fluid 1916 into the anatomical region through openings 1904. Suction lumen 1914 is used to remove lavage fluid 1916 from the anatomical region.

FIG. 20D shows a sagittal section of a human head showing the general working environment of the lavage devices of FIGS. 20A-20C. Distal end of lavage catheter 1900 is introduced into an anatomical region such as Ethmoid air cell EAC. Lavage catheter 1900 may be introduced into the EAC by an over-the-wire method, through a cannula, or by a variety of methods disclosed in this patent application and in the patents documents incorporated herein by reference. Proximal end of lavage catheter 1900 is detachably connected to a irrigation and suction apparatus 1918. Irrigation and suction apparatus 1918 provides lavage fluid 1916 to lavage catheter 1900 and also provides suction to remove lavage fluid 1916 from the EAC. Lavage catheter 1900 may similarly be used to diagnose or treat other paranasal sinuses, lachrymal ducts, ducts of salvary glands, Eustachian tubes, and other hollow organs in the ear, nose, throat or mouth.

Figure 21:
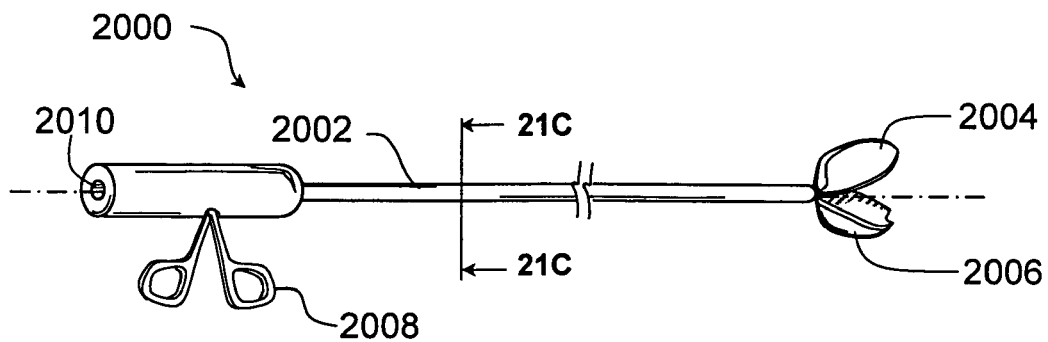
FIG. 21 shows a perspective view of a cutting device comprising cutting jaws.
Figure 21:
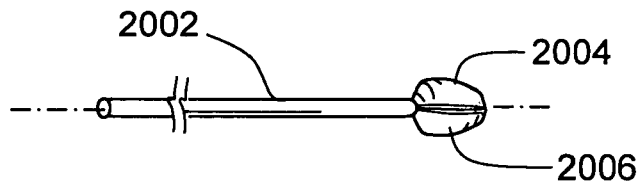
Figure 21:
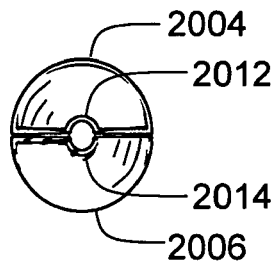
Figure 21:
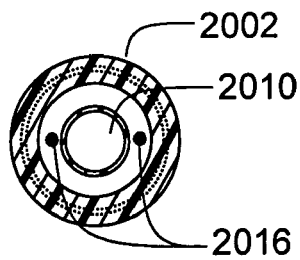

FIG. 21 shows a perspective view of a cutting device comprising cutting jaws. Cutting device 2000 comprises a shaft 2002 comprising an upper jaw 2004 and a lower jaw 2006 located on the distal end of shaft 2002. Proximal region of shaft 2002 comprises a scissor-like device with handles or other suitable control apparatus 2008 that is useable to control the movement of upper jaw 2004 and/or lower jaw 2006. Upper jaw 2004 and lower jaw 2006 are hinged together so that they can be opened or closed by scissor handles 2008 to bite, grip or cut tissue. In one embodiment, the edges of upper jaw 2004 and lower jaw 2006 are provided with a series of cutting teeth. Alternately, the edges of upper jaw 2004 and lower jaw 2006 may be provided with sharp edges, blunt gripping teeth etc. Shaft 2002 comprises a lumen 2010. This enables cutting device 2000 to be advanced over an access device such as a guidewire to access a target anatomical region. Examples of materials that can be used to construct cutting device 2000 are stainless steel 304, stainless steel 316, titanium, titanium alloys etc.

FIG. 21A shows a perspective view of the distal region of the cutting device of FIG. 21 wherein the cutting jaws are closed.

FIG. 21B shows a perspective view of one embodiment of the jaws of the cutting device of FIG. 21. Upper jaw 2004 comprises an upper jaw notch 2012. In one embodiment, upper jaw notch 2012 is semicircular in shape. Similarly, lower jaw 2006 comprises a lower jaw notch 2014. In one embodiment, lower jaw notch 2014 is semicircular in shape.

This design enables a guidewire to pass through a gap in the distal end of the cutting device 2000 even when upper jaw 2004 and lower jaw 2006 are closed. In another embodiment, a guidewire passes through an opening located on either upper jaw 2004 or lower jaw 2006. Upper jaw 2004 and lower jaw 2006 can also be square, ovoid, trapezoidal or circular in shape.

FIG. 21C shows a crossectional view of the cutting device in FIG. 21 through plane 21C-21C. Shaft 2002 of cutting device 2000 comprises a lumen 2010 for an access device such as a guidewire. Shaft 2002 further comprises one or more pull wires 2016 that connect upper jaw 2004 and lower jaw 2006 to control apparatus 2008. When the control apparatus 2008 is moved, pull wires 2016 transmit the movement to upper jaw 2004 and lower jaw 2006 causing them to open or close.

Figure 22:
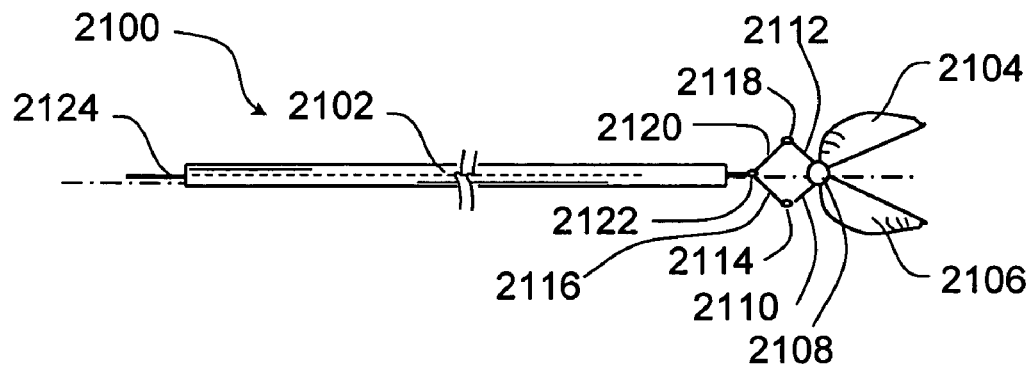
FIG. 22A shows a perspective view of an alternate embodiment of a device comprising cutting or gripping jaws.
FIG. 22B shows a perspective view of the device of FIG. 22A wherein the cutting or gripping jaws of the cutting device are in a closed configuration.
Figure 22:
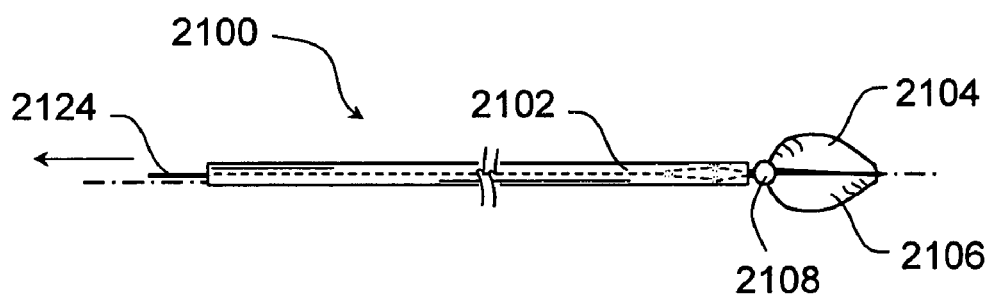

FIG. 22A shows a perspective view of an alternate embodiment of a device comprising cutting or gripping jaws. Cutting device 2100 comprises a shaft 2102. Distal end of cutting device 2100 comprises an upper jaw 2104 and a lower jaw 2106 that are hinged together at a first hinge 2108. Proximal end of upper jaw 2104 comprises a first elongate member 2110 and proximal end of second jaw 2106 comprises a second elongate member 2112. The proximal end of first elongate member 2110 is connected to a second hinge 2114 which in turn is connected to a third elongate member 2116. Proximal end of second elongate member 2112 is connected to a third hinge 2118 which in turn is connected to a fourth elongate member 2120. The proximal ends of third elongate member 2116 and fourth elongate member 2120 are connected by a fourth hinge 2122 to pull wire 2124 that passes through shaft 2102. FIG. 22A shows cutting device 2100 wherein the upper jaw 2104 and lower jaw 2106 are in an open configuration. When pull wire 2124 is pulled in the proximal direction, fourth hinge 2122 is pulled inside shaft 2102. This causes the distal ends of third elongate member 2116 and fourth elongate member 2120 to come closer to each other. This in turn causes the proximal ends of first elongate member 2110 and second elongate member 2112 to come closer to each other. This in turn causes upper jaw 2104 and lower jaw 2106 close. Similarly, pushing pull wire 2124 in the distal direction causes upper jaw 2104 and lower jaw 2106 to open. In one embodiment, cutting device 2100 comprises a spring mechanism located between pull wire 2124 and shaft 2102 that biases upper jaw 2104 and lower jaw 2106 in an open or closed configuration.

FIG. 22B shows a perspective view of the device of FIG. 22A wherein the jaws of the cutting device are in a closed configuration.

Figure 23:
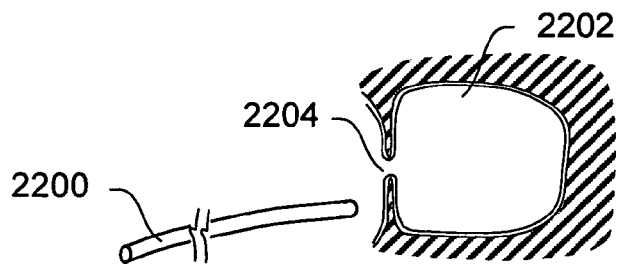
FIGS. 23A-23C show the various steps of a method of puncturing an anatomical region using a flexible, rotating drill shaft.
FIG. 23D shows a sectional view of an embodiment of a drilling device.
Figure 23:
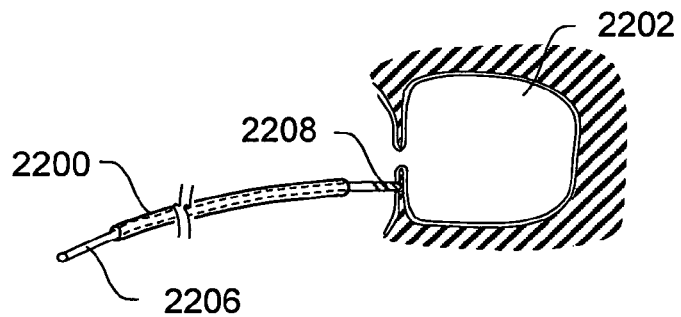
Figure 23:
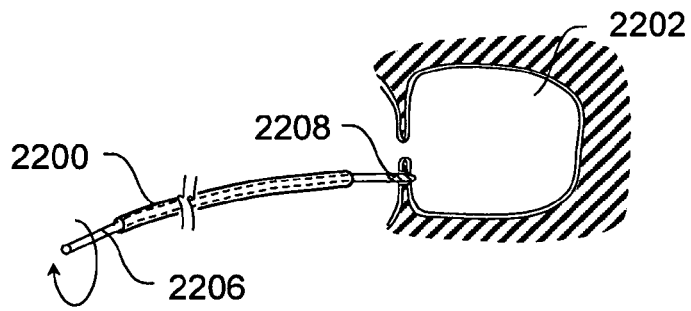
Figure 23:
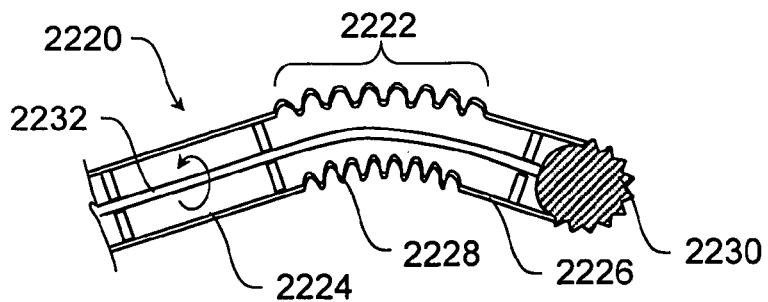

FIGS. 23A-23C show the various steps of a method of puncturing an anatomical region using a flexible, rotating drill shaft. In FIG. 23A, an access catheter 2200 is introduced through a nostril to a location adjacent to an anatomical region 2202 to be punctured. In this example, anatomical region 2202 is a maxillary sinus having a maxillary sinus ostium 2204. Other examples of the types of anatomical regions 2202 are other paranasal sinuses, lachrymal ducts, bony structures in the ear, nose, throat or mouth etc. Access catheter 2200 can be made of suitable biocompatible materials having a sufficient stiffness such as malleable stainless steel tubes; titanium tubes; fully annealed stainless steel tubes; copper tubes; aluminum tubes; tubular elements made of Pebax, HDPE etc. comprising a hypotube; etc. One or more regions of access catheter 2200 may be shapeable or malleable to allow a user to adjust the shape of access catheter 2200 to a patient's unique anatomy. A substantially stiff access catheter 2200 can be used in situations where extra support is needed for introduction or removal or devices through access catheter 2200. In an embodiment, a lubricious coating e.g. a Teflon coating is present on the inner surface of access catheter 2200. The lubricious coating can be made of suitable lubricious materials such as Teflon. In FIG. 23B, a flexible drill shaft 2206 is introduced through access catheter 2200. Access catheter 2200 helps to align flexible drill shaft 2206 in the anatomical region 2202 in a desired orientation. Flexible drill shaft 2206 can be designed for efficient transfer of unidirectional or bidirectional torque. Flexible drill shaft 2206 can be made from a suitable material having a high torsional stiffness such as heat treated spring steel. Proximal end of flexible drill shaft 2206 is connected to a reversible drive motor that is used to rotate flexible drill shaft 2206 at a desired angular velocity. Flexible drill shaft 2206 comprises a drill bit 2208 located on the distal end of flexible drill shaft 2206. Drill bit 2208 can range from 0.5 mm-5 mm in diameter. Drill bit 2208 may be made from suitable materials such as tungsten carbide, carbon steel, diamond powder coated metal etc. Drill bit 2208 can have a drill bit design such as twist drill bit, masonry drill bit, spur point bit, step drill bit etc. Flexible drill shaft 2206 is introduced through access catheter 2202 till drill bit 2208 ntouches a target location on anatomical region 2202 to be punctured. In FIG. 23C, flexible drill shaft 2206 is rotated so that drill bit 2208 punctures anatomical region 2202. Such a method and device can be used for a minimally invasive puncturing of suitable anatomical regions for drainage, aeration, introduction of diagnostic or therapeutic devices etc. Such a device and method can also be used for enlarging or clearing natural or artificial openings in anatomical regions. After a desired opening is created or enlarged, access catheter 2200 and flexible drill shaft 2206 are withdrawn from the anatomy. In one embodiment, flexible drill shaft 2206 is a non-rotating shaft having high column strength and comprising a puncturing tip at the distal end of flexible drill shaft 2206. In another embodiment, flexible drill shaft 2206 acts as an ultrasonic drill by connecting the proximal end of flexible drill shaft to an ultrasonic generator. In another embodiment, access catheter 2200 comprises one or more bearings that reduce friction between access catheter 2200 and flexible drill shaft 2206.

Figure 24:
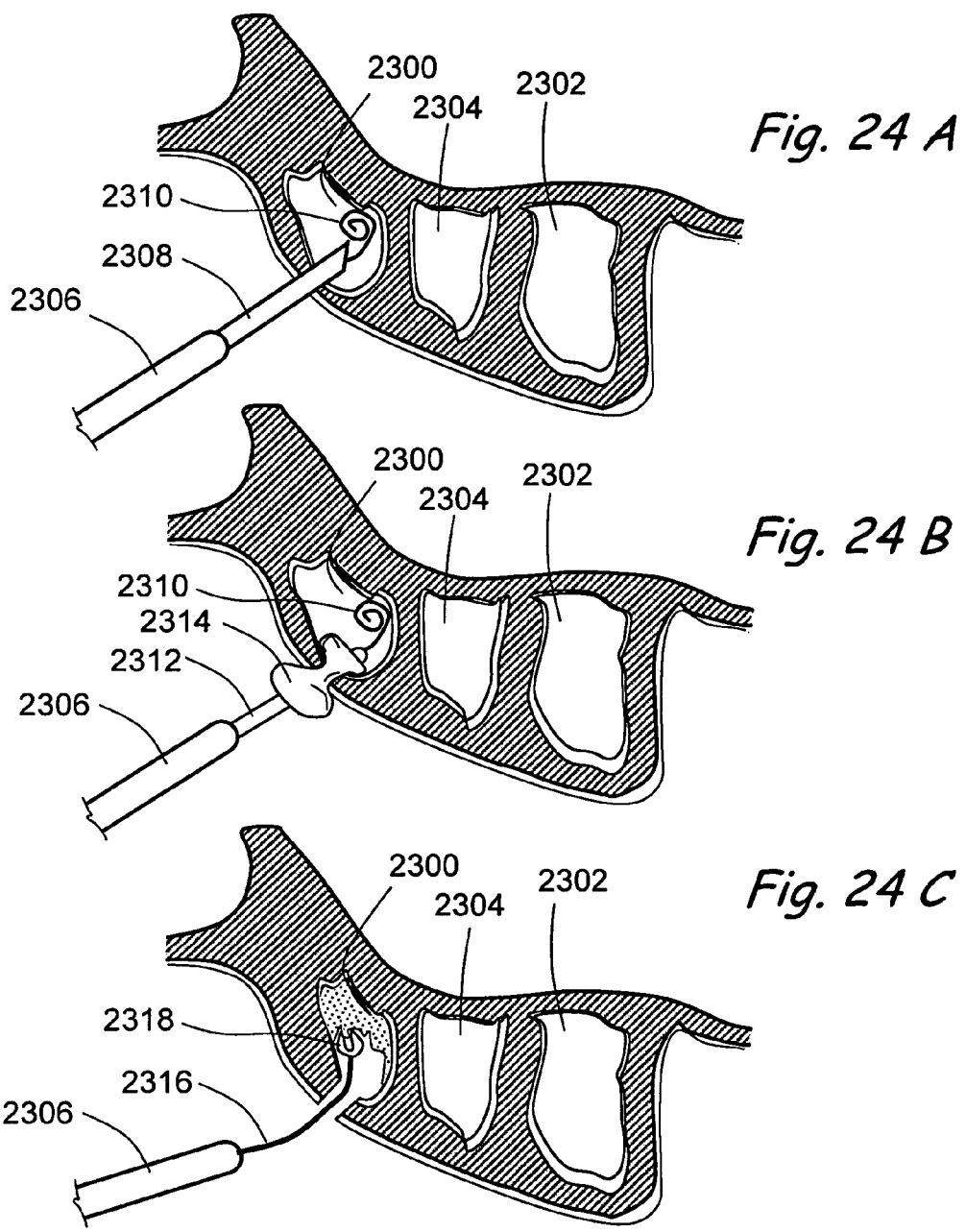
FIGS. 24A-24C show a sagittal section of an Ethmoid sinus showing various methods of treating Ethmoid sinus diseases by a minimally invasive approach.

FIG. 23D shows a sectional view of an embodiment of a drilling device. Drilling device 2220 comprises a shaft 2222 comprising a proximal rigid portion 2224 and a distal rigid portion 2226. Shaft 2222 may comprise a deformable (e.g., corrugated, plastically deformable, malleable, etc.) portion 2228 between proximal rigid portion 2224 and distal rigid portion 2226. Plastically deformable region 2228 allows the shape of drilling device 2220 to be adjusted to facilitate advancement of the device through tortous anatomy, to access to a target anatomical location and/or to achieve a desired positioning or attitude of the bit 2230 within the subject's body. Proximal rigid portion 2224, distal rigid portion 2226 and plastically deformable or malleable region 2228 can be made of suitable biocompatible materials such as stainless steel e.g. fully annealed stainless steel, copper, aluminum etc. Drilling device 2220 further comprises a rotating drill bit 2230 located at distal end of a rotatable drive member of shaft 2222. Rotating drill bit 2230 can be made from suitable materials such as tungsten carbide, carbon steel, diamond powder coated metal etc. Rotating drill bit 2230 can be an abrasive coated spherical ball or a twist (e.g., helical) drill bit, masonry drill bit, spur point bit, step drill bit etc. Proximal region of rotating drill bit 2230 is in contact with distal end of shaft 2222. In order to reduce friction between rotating drill bit 2230 and shaft 2222, the contact surfaces between rotating drill bit 2230 and shaft 2222 comprise a lubricious coating e.g. a Teflon coating. Proximal region of rotating drill bit 2230 is also attached to a flexible drive shaft 2232 that supplies torque to the rotating drill bit 2230. In one embodiment, flexible drive shaft 2232 comprises a coil assembly with high torsional stiffness and column strength. In another embodiment, flexible drive shaft 2232 comprises a heat treated spring steel cable. Proximal end of flexible drive shaft 2232 is connected to a reversible drive motor. In one embodiment, rotating drill bit 2230 and flexible drive shaft 2232 comprise a coaxial lumen to enable drilling device 2220 to be introduced over a guidewire into a target anatomy. Such a device can be used for a minimally invasive puncturing of suitable anatomical regions for drainage, aeration, introduction of diagnostic or therapeutic devices etc. Such a device can also be used for enlarging or clearing natural or artificial openings in anatomical regions. It will be appreciated by those of skill in the art that, although this device 2220 is referred to herein as a "drilling device" it may be used for numerous purposes other than "drilling." For example, this device 2220 may be used to cut, grind, polish or create grooves or depressions in bone, cartilage or other tissue and/or may be used as a screw driver. Thus, in some applications, this drilling device 2220 may alternatively be aptly referred to as a cutter, grinder, rotating rasp, rotating brush, dremmel, polisher, burnisher, boring tool, grooving tool, etc. Also, in some embodiments, the bit may comprise a drive bit that is useable to drive a permanent or resorbable bone screw or other type of screw or anchor. Also, the bit 2230 may be interchangeable and a variety of different bits 2220 may be provided to accomplish various different applications (e.g., grinding, polishing, burnishing, grooving, boring, rasping, debulking, forming indentations or depressions, driving screws, etc.). FIGS. 24A-24C show a sagittal section of an Ethmoid sinus showing various methods of treating Ethmoid sinus diseases by a minimally invasive approach. FIG. 24A shows a sagittal section of an Ethmoid sinus comprising an anterior Ethmoid air cell 2300, a posterior Ethmoid air cell 2302 and an intermediate Ethmoid air cell 2304 located between anterior Ethmoid air cell 2300 and posterior Ethmoid air cell 2302. A guide catheter 2306 is introduced to a region inferior to the basal lamella of a middle turbinate. Guide catheter 2306 may comprise a design selected from the various guide catheter designs disclosed herein and in the patent documents incorporated herein by reference. Thereafter, an introducer needle 2308 is introduced through guide catheter 2306. Introducer needle 2308 comprises a lumen through which devices such as guidewires can be introduced. Introducer needle 2308 can be made of suitable biocompatible materials such as Stainless steel, Nitinol, polymers, polymer-metal composites etc. Introducer needle 2308 is advanced through guide catheter 2306 such that the distal tip of introducer needle 2308 punctures a wall of an Ethmoid air cell e.g. anterior Ethmoid air cell 2300 and enters the Ethmoid air cell. Thereafter, a guidewire 2310 is introduced through introducer needle 2308 into the Ethmoid air cell e.g. anterior Ethmoid air cell 2300. Thereafter, introducer needle 2308 is removed from the anatomy. In FIG. 24B, a working device is introduced over guidewire 2310 into the Ethmoid air cell. An example of a working device is a balloon catheter 2312 comprising a dilating balloon 2314. Thereafter, the working device is used to perform a diagnostic or therapeutic procedure e.g. balloon dilation of the introducer needle puncture site to create a drainage channel for sinus secretions. Similarly, other working devices such as dilating or occluding balloons, dilating stents, suction or irrigation devices, needles, polypectomy tools, brushes, energy emitting devices such as ablation devices, laser devices, image-guided devices containing sensors or transmitters, imaging devices, endoscopes, tissue modifying devices such as cutters, biopsy devices, devices for injecting diagnostic or therapeutic agents, lavage devices, drug delivery devices such as substance eluting devices, substance delivery implants etc. may be used to perform diagnostic or therapeutic procedures. The method shown in FIGS. 24A-24B may also be used to create an opening of a suitable diameter to facilitate insertion of other working devices into the Ethmoid air cells. For example, FIG. 24C shows a method of treating Ethmoid sinus diseases by a rongeur. In this method, rongeur 2316 having a distal cutting tip 2318 is introduced through guide catheter 2306 into an Ethmoid air cell via the introducer needle puncture site. Thereafter, rongeur 2316 is used to remove tissue from the Ethmoid air cell.

FIGS. 24A'-24A''' show a method of creating drainage channels for sinus secretions in Ethmoid sinus. In FIG. 24A', guide catheter 2306 is introduced to a region inferior to the basal lamella of a middle turbinate. Thereafter, introducer needle 2308 is advanced through guide catheter 2306 such that the distal tip of introducer needle 2308 punctures a wall of an Ethmoid air cell e.g. an intermediate Ethmoid air cell 2304 and enters the Ethmoid air cell. In FIG. 24A'', introducer needle is used to create internal channels in the Ethmoid sinus by puncturing walls of adjacent Ethmoid air cells e.g. anterior Ethmoid air cell 2300, posterior Ethmoid air cell 2302 etc. In FIG. 24A''', introducer needle 2308 and guide catheter 2306 are removed leaving behind internal channels that allow drainage of sinus secretions through the introducer needle puncture site in the intermediate Ethmoid air cell 2304. Sinus secretions from anterior Ethmoid air cell 2300 or posterior Ethmoid air cell 2302 flow into intermediate Ethmoid air cell 2304 from which they flow out of the Ethmoid sinus. The internal channels as well as the introducer needle puncture site in the intermediate Ethmoid air cell 2304 may be dilated using a balloon catheter as shown in FIGS. 24A-24B. In FIGS. 24A'-24A''', introducer needle 2308 was introduced into the Ethmoid sinus through intermediate Ethmoid air cell 2304. Similar procedures may be performed by introducing introducer needle 2304 into the Ethmoid sinus through anterior Ethmoid air cell 2300 or posterior Ethmoid air cell 2302. In one embodiment, anterior Ethmoid air cell 2300, posterior Ethmoid air cell 2302 and intermediate Ethmoid air cell 2304 are punctured separately through the basal lamella of a middle turbinate to create separate drainage channels for each Ethmoid air cell as shown in FIG. 24A''''.

Figure 25:
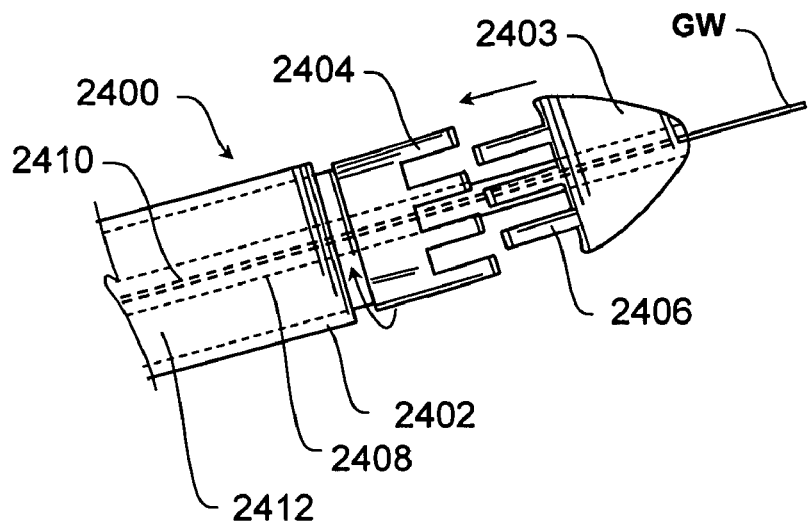
FIG. 25A shows a perspective view of an embodiment of an ostium enlarger and/or microshaver.
FIG. 25B shows one embodiment of the device of FIG. 25A being used to remove tissue or matter.
FIG. 25C shown another embodiment of the device of FIG. 25A being used to shave tissue or matter.
FIG. 25D is an exploded view of the device of FIG. 25C.
Figure 25:
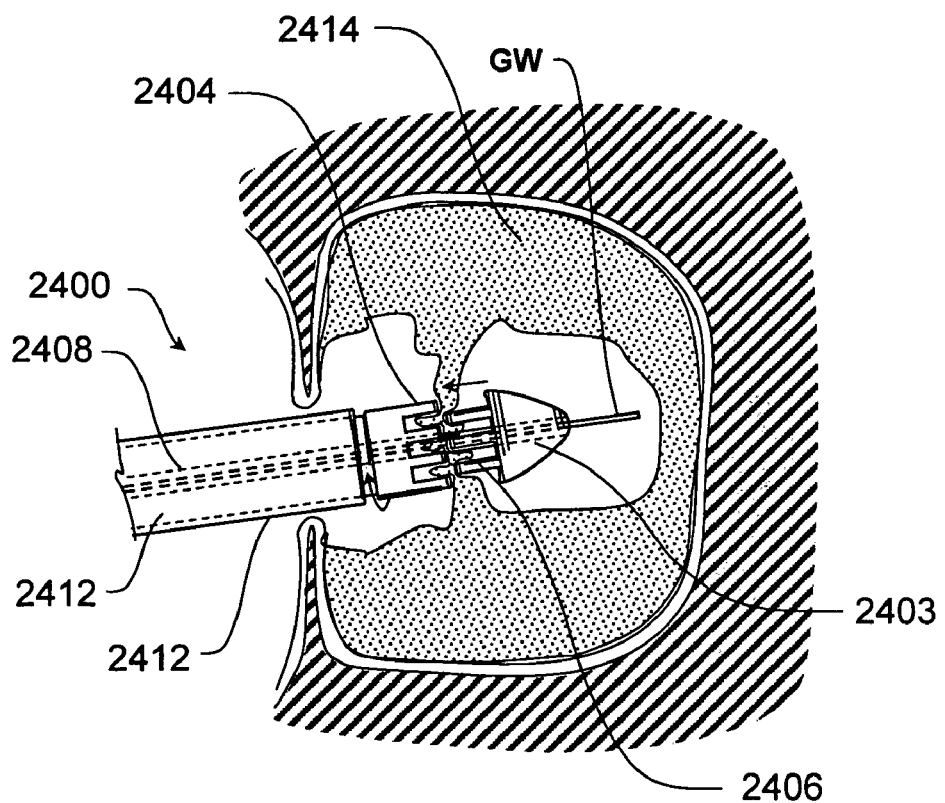
Figure 25:
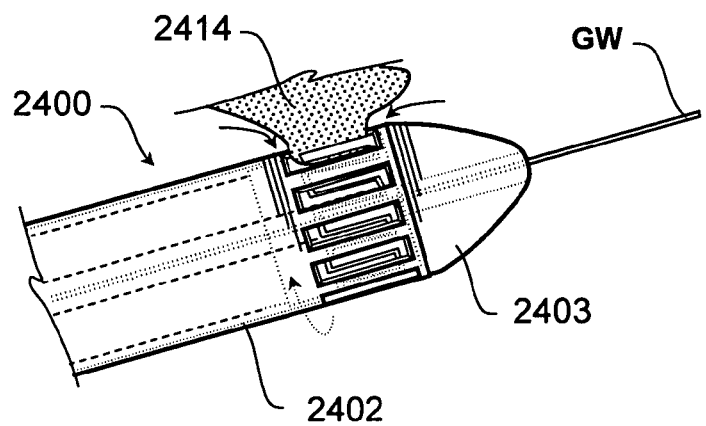
Figure 25:
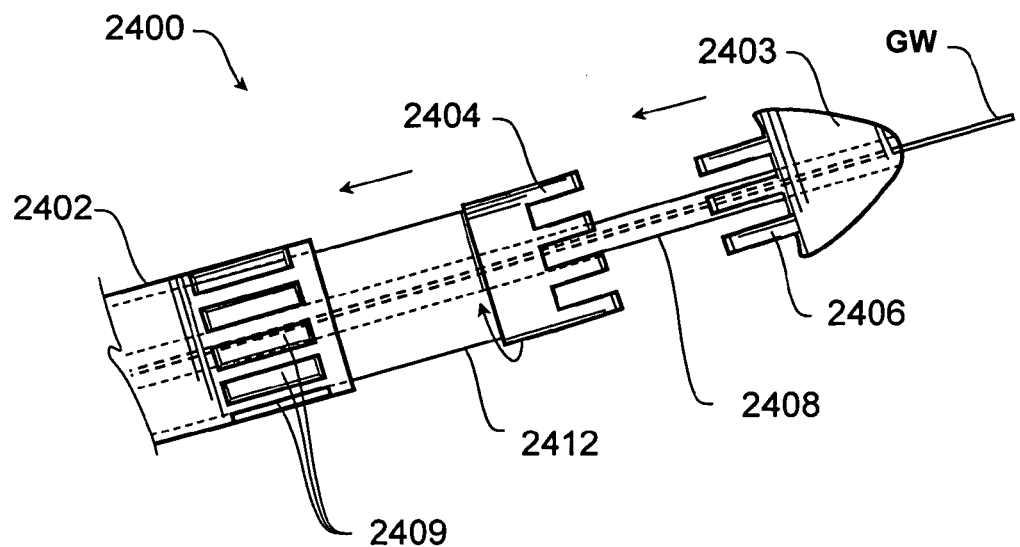

FIG. 25A shows a perspective view of an embodiment of a microshaver or ostium enlarger device 2400. Device 2400 comprises a proximal portion 2402 and a distal portion 2403. Proximal portion 2402 is hollow and comprises a proximal cutting surface 2404 e.g. sharp cutting teeth etc. located on the distal end of proximal portion 2402. Distal portion 2403 comprises a distal cutting surface 2406 e.g. sharp cutting teeth etc. located on the proximal end of distal portion 2403. Distal portion 2403 is further connected to a pull shaft 2408 that encloses a guidewire lumen 2410. Guidewire lumen 2410 allows microshaver 2400 to be introduced over a guidewire GW into a target anatomy. The region between pull shaft 2408 and proximal portion 2402 encloses a suction lumen 2412. Suction lumen 2412 can be used to remove solid debris or liquids from the target anatomy by suction. Proximal portion 2402, distal portion 2403 and pull shaft 2408 can be made of suitable biocompatible materials such as stainless steel.

FIG. 25B shows a crossection of a paranasal sinus showing one way in which the device 2400 of FIG. 25A may be used to remove tissue or matter. The device 2400 is introduced over a guidewire GW into paranasal sinus 2414. The device 2400 is then positioned such that the tissue or matter is located between proximal cutting surface 2404 and distal cutting surface 2406. Thereafter, in this embodiment, pull shaft 2408 is pulled in the proximal direction. This causes movement of distal region 2403 in the proximal direction with respect to proximal portion 2402. This in turn forces cylindrical distal cutter 2406 to be retracted into the interior of the cylindrical proximal cutter 2404, thereby cutting off or breaking tissue or matter that is captured therebetween. Optionally, in this embodiment, the cylindrical distal cutter 2406 cylindrical proximal cutter 2404 may be rotated relative to the other to further cut or shave tissue. Also, optionally in this embodiment, suction lumen 2412 can be used to remove any solid debris or liquids generated during the procedure.

FIGS. 25C and 25D show an example of another way in which the device 2400 may be used—i.e., to shave tissue or matter. Examples of anatomical structures that may be shaved by this device 2400 include bone, cartilage and soft tissues of Eustachian tubes, turbinates, lachrymal ducts, anatomical openings such as ostia of paranasal sinuses, ostia of lachrymal ducts, etc. and other regions in the ear, nose, throat or mouth. As shown in FIG. 25C, in this embodiment, there need not be a proximally moveable pull shaft 2408, but rather the distal cutting surface 2406 may remain positioned within the cylindrical proximal cutting surface 2404. The cutting surfaces are positioned adjacent to the tissue or matter to be shaved and the cylindrical distal cutter 2406 and/or cylindrical proximal cutter 2404 is/are rotated to shave the tissue or matter. Suction may be applied through lumen 2412 to draw the tissue or matter into slots 2409 such that it will be shaved by the rotating proximal cutter 2404.

Figure 26A:
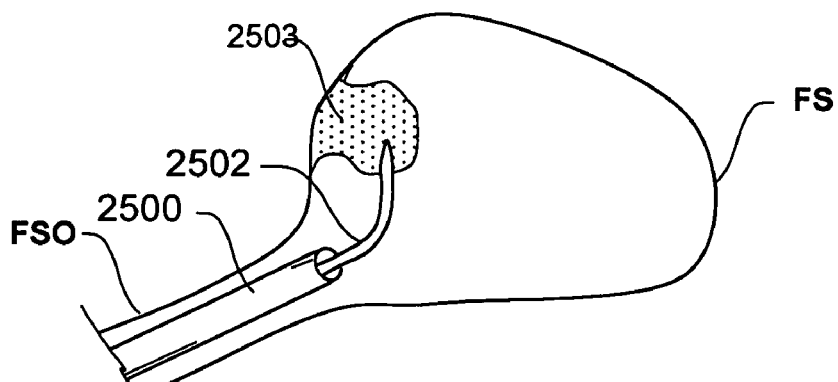
FIGS. 26A-26C show various steps of a method of treating a mucocyst by a puncturing needle and a balloon catheter.
Figure 26:
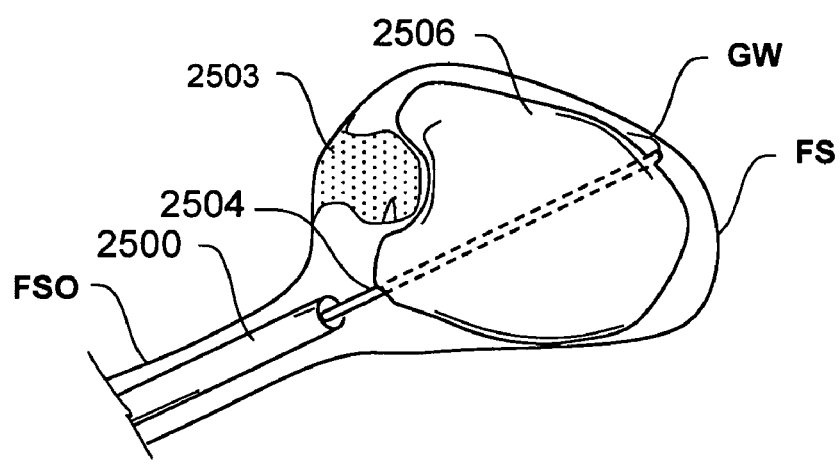
Figure 26:
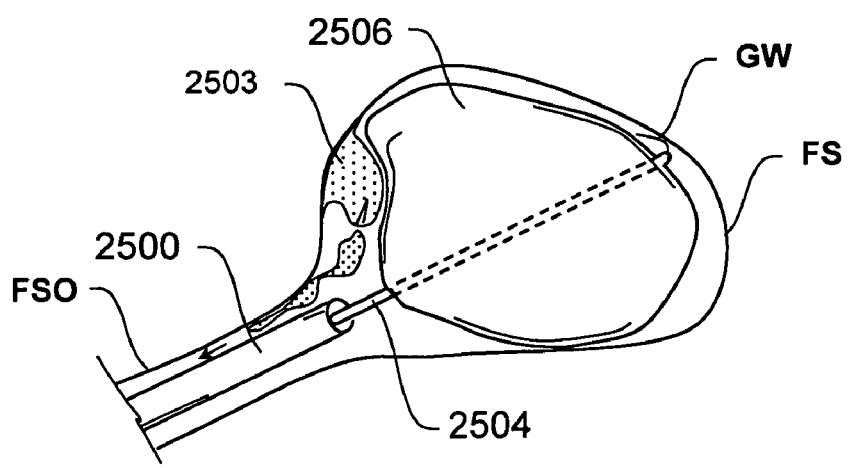

FIGS. 26A-26C show a device and method for treating a mucocyst of other flowable substance-containing structure (e.g., cyst, hematoma, pustule, etc.) located within a paranasal sinus, ear, nose or throat. In general, the device comprises an elongate shaft 2500, a penetrator such as a needle 2502 that is advanceable from and retractable into the shaft 2500 to form an opening in the mucocyst or other structure, and a compressor such as a balloon 2506 that is useable to compress the mucocyst or other structure to force its contents to flow out of the opening created by the needle 2502 or other penetrator. Specifically, as shown in the example of FIG. 26A, a guide catheter 2500 is introduced into an anatomical region through an anatomical opening. The outer diameter of guide catheter 2500 is less than the inner diameter of the anatomical opening. In FIGS. 26A-26C, frontal sinus FS is used as an example of an anatomical region. Other examples of anatomical regions are other paranasal sinuses, lachrymal passages, Eustachian tubes and other structures in the ear, nose, throat or mouth etc. Guide catheter 2500 may comprise a design selected from the various guide catheter designs disclosed herein and in the patent documents incorporated herein by reference. A puncturing needle 2502 is then introduced through guide catheter 2500 into the frontal sinus FS. Puncturing needle 2502 has a sharp distal tip and can be made from a variety of materials such as hardened tool steel, stainless steel etc. Puncturing needle 2502 is navigated through the frontal sinus FS such that the distal tip of puncturing needle 2502 punctures a mucocyst 2503 in the frontal sinus FS. Thereafter, puncturing needle 2502 is withdrawn. In FIG. 26B, a guidewire GW is introduced into the frontal sinus FS. Thereafter, a balloon catheter 2504 comprising a balloon 2506 is introduced over guidewire GW into the frontal sinus FS. Balloon 2506 can be made of suitable compliant or semi-compliant materials such as crosslinked polyethylene or other polyolefins, polyurethane, flexible polyvinylchloride, Nylon, etc. Balloon 2506 is then inflated. Inflated balloon 2506 compresses the punctured mucocyst 2503. This causes drainage of mucocyst secretions into the frontal sinus FS. In FIG. 26C, balloon 2506 is inflated further so that it occupies a volume in the frontal sinus FS and displaces the mucocyst secretions from the frontal sinus FS out through the frontal sinus ostium FSO.

Figure 27:
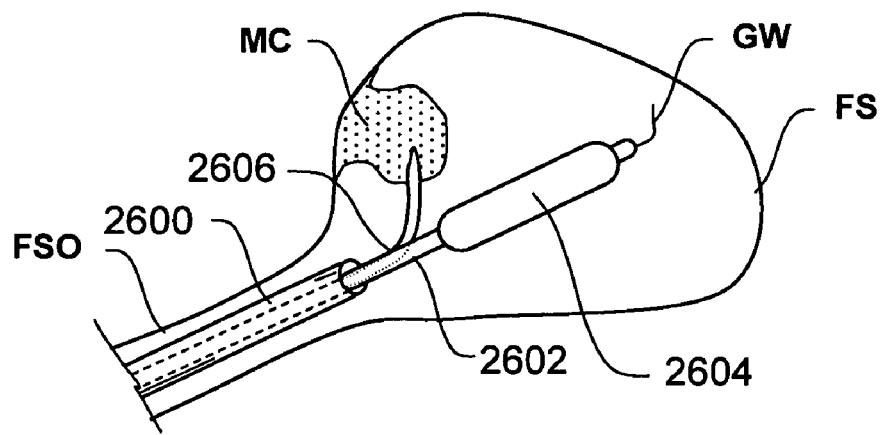
FIGS. 27A-27B show various steps of a method of treating a mucocyst by a balloon catheter comprising a deployable puncturing needle.
Figure 27:
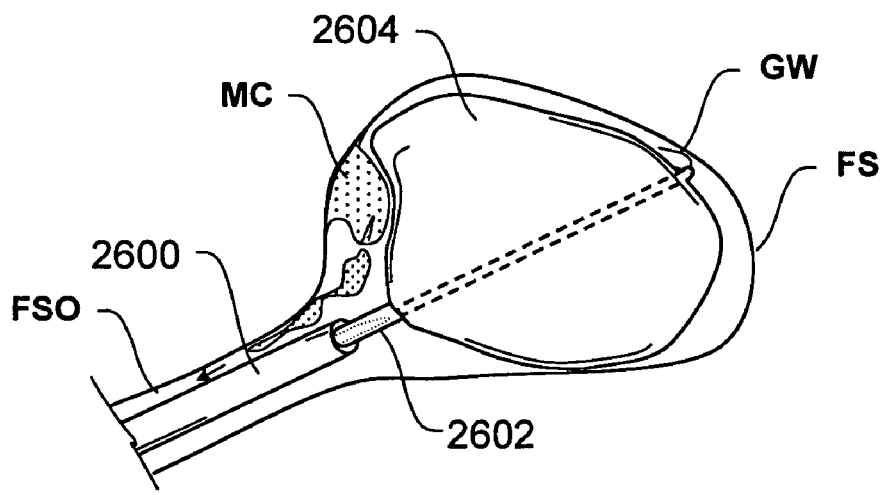

FIGS. 27A-27B show various steps of a method of treating a mucocyst by a balloon catheter comprising a deployable puncturing needle. In FIG. 27A, a guide catheter 2600 is introduced into an anatomical region through an anatomical opening. The outer diameter of guide catheter 2600 is less than the inner diameter of the anatomical opening. In FIGS. 27A-27B, frontal sinus FS is used as an example of an anatomical region. Other examples of anatomical regions are other paranasal sinuses, lachrymal passages, Eustachian tubes, other ear, nose, throat and mouth structures etc. Guide catheter 2600 may comprise a design selected from the various guide catheter designs disclosed herein and in the patent documents incorporated herein by reference. A balloon catheter 2602 comprising a balloon 2604 and a deployable puncturing needle 2606 is then introduced through guide catheter 2600 into the frontal sinus FS. Balloon 2604 can be made of suitable compliant or semi-compliant materials such as crosslinked polyethylene or other polyolefins, polyurethane, flexible polyvinylchloride, Nylon, etc. Deployable puncturing needle 2606 can be made from a variety of materials such as hardened tool steel, stainless steel etc. Balloon catheter 2604 is oriented in a desired orientation and deployable puncturing needle 2606 is advanced such that the distal tip of deployable puncturing needle 2606 punctures the mucocyst MC. Thereafter, deployable puncturing needle 2606 is withdrawn into balloon catheter 2602. In FIG. 27B, balloon 2604 is inflated. Inflated balloon 2604 compresses the punctured mucocyst MC. This causes drainage of mucocyst secretions into the frontal sinus FS. Balloon 2604 is then inflated further so that it occupies a volume in the frontal sinus FS and displaces the mucocyst secretions from the frontal sinus FS out through the frontal sinus ostium FSO. In one embodiment, deployable puncturing needle 2606 is located in a needle lumen. Deployable puncturing needle 2606 may be advanced or withdrawn by advancing or withdrawing deployable puncturing needle 2606 through the needle lumen.

Figure 28:
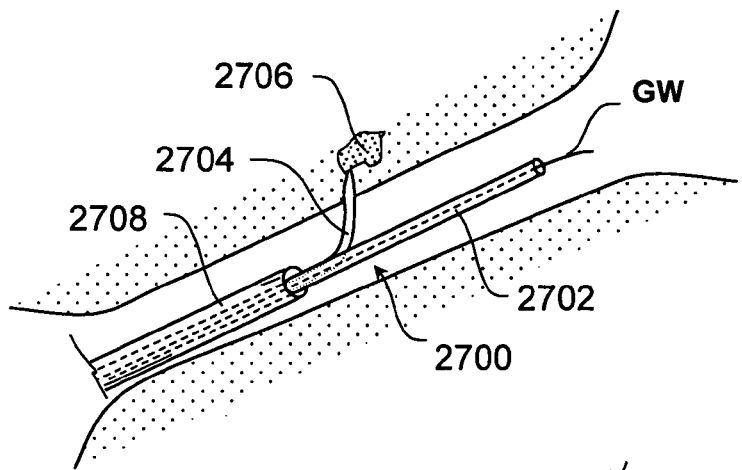
FIGS. 28A-28C show various embodiments of catheters comprising agent delivery needles.
Figure 28B:
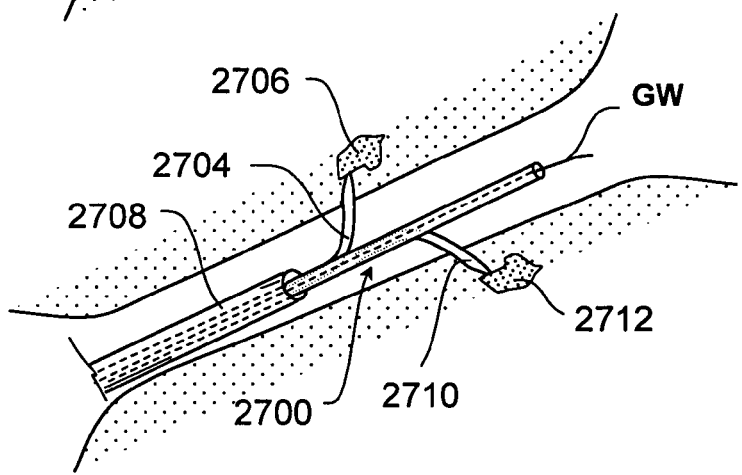
Figure 28:
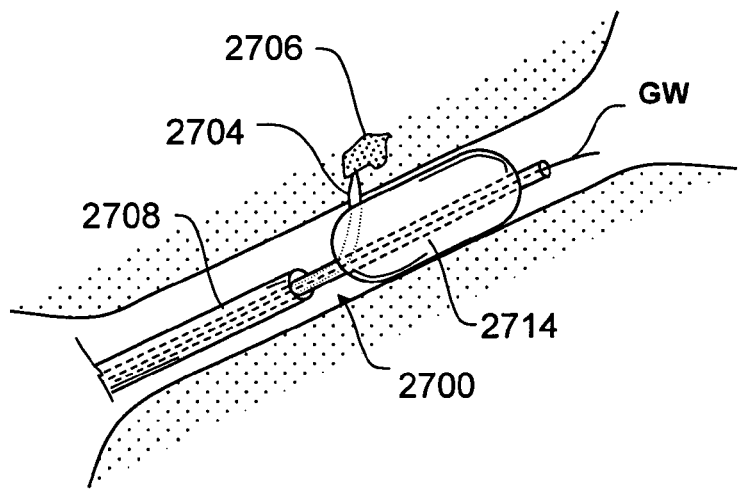

FIGS. 28A-28C show various embodiments of catheters comprising agent delivery needles. In FIG. 28A, catheter 2700 comprises a shaft 2702 having a guidewire lumen. Catheter 2700 further comprises a deployable injecting needle 2704 made from suitable biocompatible materials such as stainless steel. Deployable injecting needle 2704 comprises a lumen for injecting one or more diagnostic or therapeutic agents 2706 into the adjacent anatomy. Deployable injecting needle 2704 is deployed at any suitable angle to the longitudinal axis of shaft 2702, for example such angle may range from 0 degrees to 135 degrees. In one embodiment, deployable injecting needle 2704 is located in a needle lumen. Deployable injecting needle 2704 is deployed or withdrawn by relative motion of deployable injecting needle 2704 with respect to shaft 2702. In another embodiment, deployable injecting needle 2704 can be deployed or withdrawn by inflating or deflating a deploying balloon. The deploying balloon can be made from suitable materials such as polyimide, parylene (e.g. C,D,N), silicone, polyurethane, polyethylene terephthalate etc. Catheter 2700 is introduced into a target anatomy and deployable injecting needle 2704 is deployed. Deployable injecting needle 2704 penetrates into the adjacent anatomy. One or more diagnostic or therapeutic agents 2706 are then injected into the adjacent anatomy. In one embodiment, catheter 2700 may be introduced in an anatomical region through a guide catheter 2708. FIG. 28B shows a perspective view of catheter 2700 of FIG. 28A wherein catheter 2700 further comprises a second deployable injecting needle 2710. Second deployable injecting needle 2710 comprises a lumen for injecting one or more diagnostic or therapeutic agents 2712 into the adjacent anatomy. In one embodiment, diagnostic or therapeutic agents 2712 are the same as diagnostic or therapeutic agents 2706. FIG. 28C shows a perspective view of catheter 2700 of FIG. 28A wherein catheter 2700 further comprises a balloon 2714. In one embodiment, balloon 2714 is a dilating balloon made of suitable non-compliant materials e.g. polyethylene terephthalate etc. This embodiment can be used for both balloon dilation and agent delivery. In another embodiment, balloon 2714 is an anchoring balloon made of suitable non-compliant materials e.g. polyethylene terephthalate etc. or suitable compliant or semi-compliant materials such as crosslinked polyethylene or other polyolefins, polyurethane, flexible polyvinylchloride, Nylon etc. The anchoring balloon can be used to stabilize the position and orientation of catheter 2700 before agent delivery.

Examples of diagnostic or therapeutic agents that can be delivered by the catheters in FIGS. 28A-28C are pharmaceutically acceptable salt or dosage form of an antimicrobial agent (e.g., antibiotic, antiviral, anti-parasitic, antifungal, etc.), an anesthetic agent with or without a vasoconstriction agents (e.g. Xylocaine with or without Epinephrine, Tetracaine with or without epinephrine, etc.), an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), an allergen or another substance that causes secretion of mucous by tissues, hemostatic agents to stop bleeding, anti-proliferative agents, cytotoxic agents e.g. alcohol, biological agents such as protein molecules, stem cells, genes or gene therapy preparations, viral vectors carrying DNA, proteins or mRNA coding for important therapeutic functions or substances etc. Catheters in FIGS. 28A-28C can be used to diagnose or treat anatomical regions such as paranasal sinuses, regions in the Eustachian tubes, lachrymal ducts, ducts of salvary glands, anatomical openings such as ostia of paranasal sinuses, ostia of lachrymal ducts, other regions in the ear, nose, throat or mouth etc.

Figure 29:
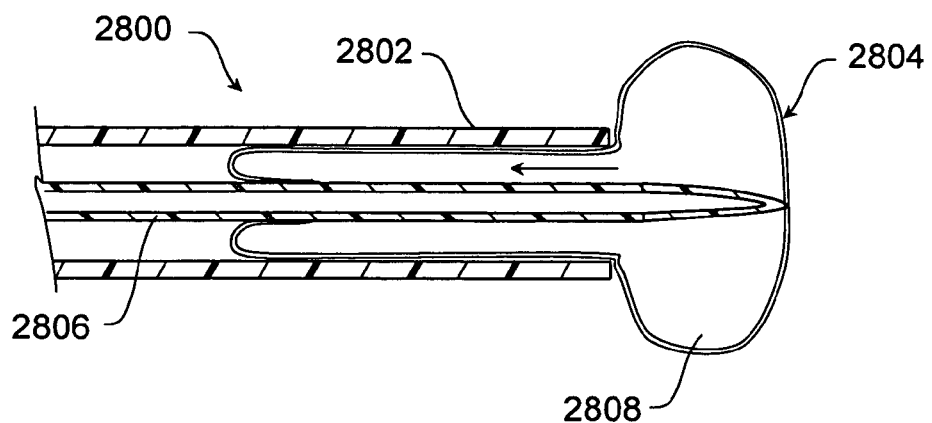
FIG. 29A illustrates an embodiment of a displacement catheter to displace and remove secretions in an anatomical region.
FIG. 29B shows a sectional view of an anatomical region showing a method of displacing secretions by the displacement catheter of FIG. 29A.
Figure 29:
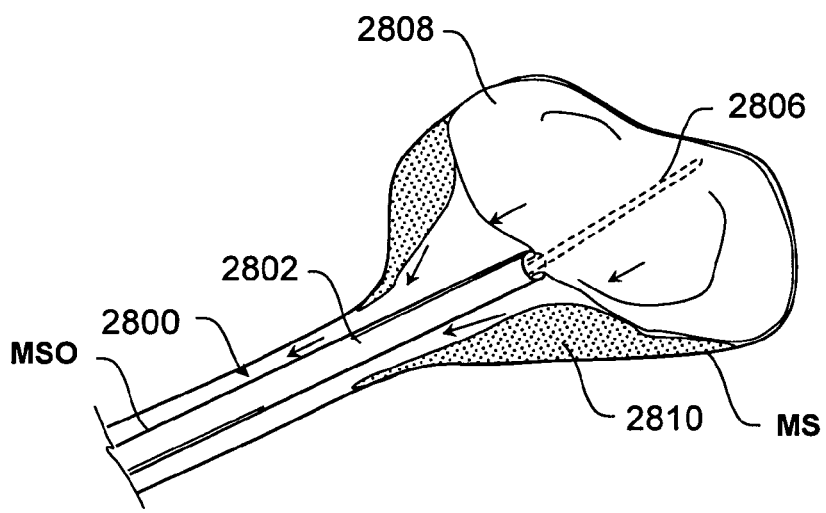

FIG. 29A illustrates an embodiment of a displacement catheter to displace and remove secretions in an anatomical region. Displacement catheter 2800 comprises an outer sheath 2802 that encloses a balloon catheter 2804. Outer sheath 2802 may be flexible or substantially rigid. Outer sheath 2802 may be made of suitable materials such as Pebax, HDPE etc. Outer sheath 2802 may comprise a hypotube made of suitable biocompatible materials such as stainless steel, Nitinol etc. Balloon catheter 2804 comprises a catheter shaft 2806 and a balloon 2808 located on the distal region of catheter shaft 2806. Catheter shaft 2806 may be made of suitable materials such as Pebax, HDPE etc. Balloon 2808 may be made from suitable compliant or semi-compliant material such as crosslinked polyethylene or other polyolefins, polyurethane, flexible polyvinylchloride, Nylon etc.

FIG. 29B shows a sectional view of an anatomical region showing a method of displacing secretions by the displacement catheter of FIG. 29A. Displacement catheter 2800 is introduced in an anatomical region. In FIG. 29B, a Maxillary sinus MS is used as an example of an anatomical region. Other examples of anatomical regions that can be treated using displacement catheter 2800 are other paranasal sinuses, lachrymal passages, Eustachian tubes etc. Displacement catheter 2800 can be advanced into an anatomical region through natural openings e.g. ostia of sinuses or artificially created openings. In this example, displacement catheter 2800 is advanced into the Maxillary sinus through a natural opening such as a maxillary sinus ostium MSO such that the distal end of displacement catheter is near the distal region of Maxillary sinus MS. Outer diameter of outer sheath 2802 is less than inner diameter of Maxillary sinus ostium MSO. Thereafter, outer sheath 2802 is withdrawn gradually by pulling outer sheath 2802 in the proximal direction over balloon catheter 2804. Simultaneously, balloon 2808 is inflated by a suitable inflating medium such as saline mixed with radiographic contrast. This causes distal region of balloon 2804 to inflate before the proximal region of balloon 2804. Balloon 2804 gradually begins to occupy available volume in the Maxillary sinus MS and thus displaces secretions 2810 out of the Maxillary sinus MS through the Maxillary sinus ostium MSO. In one embodiment of balloon 2804, distal region of balloon 2804 has a higher compliance than proximal regions of balloon 2804. In another embodiment, balloon 2804 comprises multiple compartments such that each compartment can be inflated independently of other compartments. Balloon 2804 may be detachably connected to catheter shaft 2806 to enable permanent occlusion of the anatomical region. Balloon 2804 may also comprise a variety of drug delivery mechanisms including drug eluting coatings, drug eluting pores for eluting a drug dissolved in the inflating medium etc.

Figure 30:
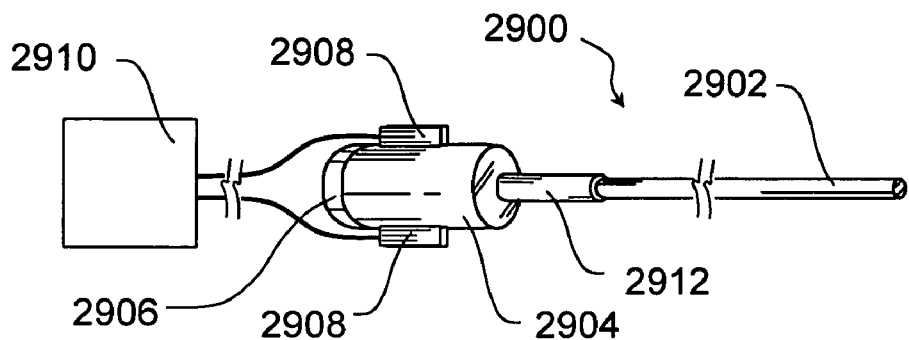
FIG. 30 shows a perspective view of an embodiment of an ultrasonic drilling device.
Figure 30:
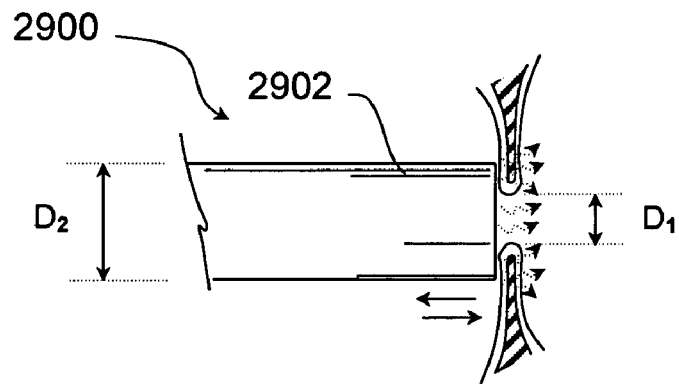
Figure 30:
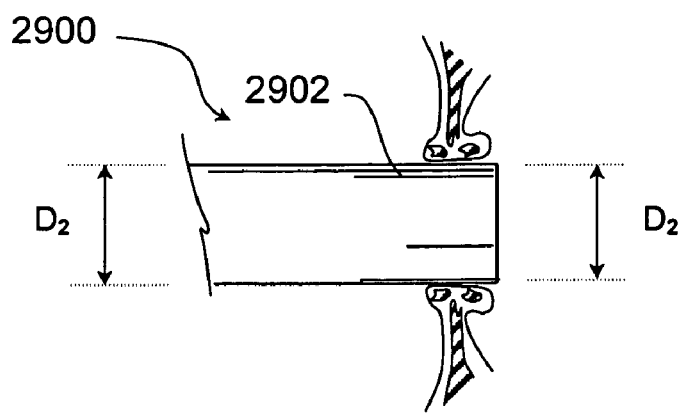

FIG. 30 shows a perspective view of an embodiment of an ultrasonic drilling device. Drilling device 2900 comprises a rigid or flexible drilling shaft 2902. Drilling shaft 2902 can be made of suitable materials such as tungsten carbide flexible wire. The proximal end of drilling shaft 2902 is connected to a piezoelectric crystal 2904 such as a quartz ($SiO_2$) or barium titanate ($BaTiO_3$) crystal. Piezoelectric crystal 2904 may have a layer of backing material 2906 on the proximal surface of piezoelectric crystal 2904. Piezoelectric crystal 2904 is connected by electrodes 2908 to an electric power source 2910. Electric power source 2910 delivers a suitable current via electrodes 2908 to piezoelectric crystal 2904 to cause piezoelectric crystal 2904 to vibrate at an ultrasonic frequency. The vibration of piezoelectric crystal 2904 is transmitted to drilling shaft 2902. In one embodiment, drilling shaft 2902 is connected to piezoelectric crystal 2904 by a coupler 2912.

FIGS. 30A-30B show a sectional view of an anatomical region showing a method of enlarging a natural or artificially created anatomical opening using the drilling device of FIG. 30. The drilling device may also be used to create new openings in an anatomical region. Distal part of drilling device 2900 comprising drilling shaft 2902 of diameter $D_2$ is positioned such that the distal end of drilling shaft 2902 touches an anatomical opening e.g. a sphenoid sinus ostium SSO to be dilated. The anatomical opening has an initial diameter $D_1$. Thereafter, current from electric power source 2910 is switched on, which in turn causes drilling shaft 2902 to vibrate in the axial direction. The vibration of drilling shaft 2902 causes distal tip of drilling shaft 2902 to impact the anatomical opening. In FIG. 30B, the impact of drilling shaft 2902 causes dilation of the anatomical opening from an initial diameter $D_1$ to a diameter $D_2$.

Similarly, other embodiments of drilling devices may be used to puncture, remodel or change the shape, size or configuration of anatomical structures such as paranasal sinuses, Eustachian tubes, middle ear, nasopharynx, Lachrymal ducts or other anatomical regions in the ear, nose, throat or mouth.

Such drilling devices may comprise for example elements for ablation or delivery of energy such as laser, RF, thermal shock waves etc.

Figure 31:
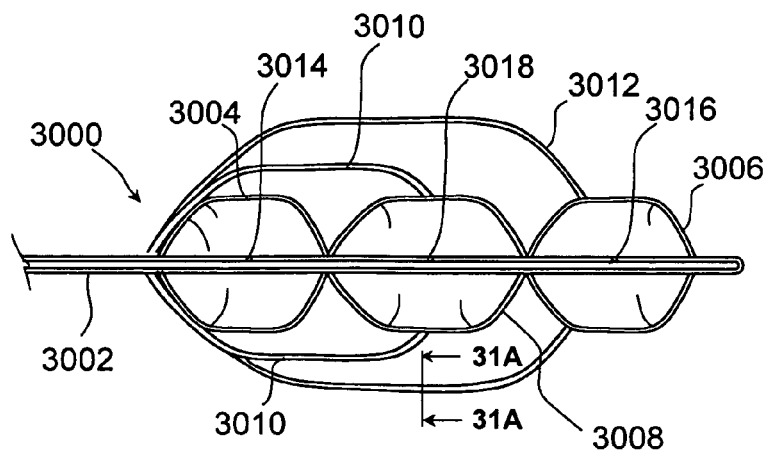
FIG. 31 shows a sectional view of an embodiment of a catheter for providing an internal cast for fractured bony cavities.
Figure 31:
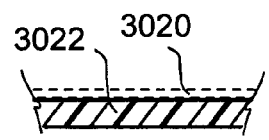

FIG. 31 shows a sectional view of an embodiment of a catheter for providing an internal cast for fractured bony cavities. Catheter 3000 comprises a shaft 3002 comprising a plurality of inflating elements e.g. inflating balloon in the distal region of shaft 3002. In the example shown in FIG. 31, catheter 3000 comprises a proximal interior balloon 3004, a distal interior balloon 3006 and an intermediate interior balloon 3008 located between proximal interior balloon 3004 and distal interior balloon 3006. Catheter 3000 further comprises an intermediate balloon 3010 covering proximal interior balloon 3004 and intermediate interior balloon 3008 as shown in FIG. 31. Catheter 3000 further comprises an outer balloon 3012 that covers intermediate balloon 3010 and a portion of distal interior balloon 3006 as shown in FIG. 31. The balloons on catheter 3000 can be inflated independently of each other. For example proximal interior balloon 3004 can be inflated by a proximal interior balloon lumen 3014, distal interior balloon 3006 can be inflated by a distal interior balloon inflation lumen 3016 and intermediate interior balloon 3008 can be inflated by an intermediate balloon inflation lumen 3018. The balloons on catheter 3000 may be made from suitable compliant or semi-compliant material such as crosslinked polyethylene or other polyolefins, polyurethane, flexible polyvinylchloride, Nylon etc. or from suitable non-compliant materials e.g. polyethylene terephthalate etc. The balloons on catheter 3000 may be coated with a variety of coatings including lubricious coatings, drug eluting coatings etc. FIG. 31A shows a crossection through the outer balloon 3012 in the catheter 3000 of FIG. 31 through plane 31A-31A. Outer balloon 3012 comprises a balloon material 3020 made from suitable compliant or semi-compliant material such as crosslinked polyethylene or other polyolefins, polyurethane, flexible polyvinylchloride, Nylon etc. or from suitable non-compliant materials e.g. polyethylene terephthalate etc. A coating 3022 is located on the outer surface of balloon material 3020. Examples of materials that can be used in coating 3022 are contrast agents, pharmaceutically acceptable salt or dosage form of an antimicrobial agent (e.g., antibiotic, antiviral, anti-parasitic, antifungal, etc.), an anesthetic agent with or without a vasoconstriction agents (e.g. Xylocaine with or without Epinephrine, Tetracaine with or without epinephrine, etc.), an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), an allergen or another substance that causes secretion of mucous by tissues, hemostatic agents to stop bleeding, anti-proliferative agents, cytotoxic agents e.g. alcohol, biological agents such as protein molecules, stem cells, genes or gene therapy preparations etc.

Figures 31, 31B:
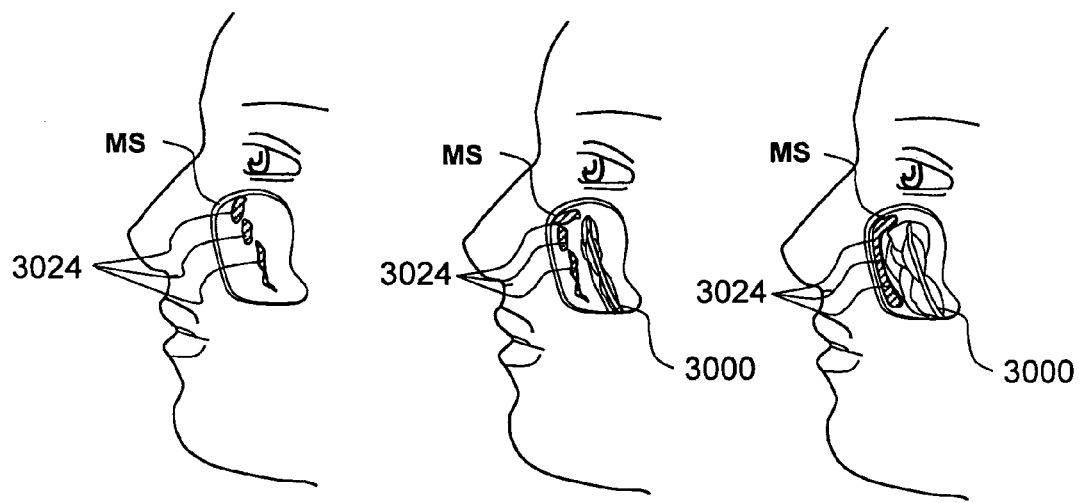

FIGS. 31B-31D shows various steps of a method of providing an internal cast for a fractured bony cavity using the catheter shown in FIG. 31. In FIGS. 31B-31D, Maxillary sinus MS is used as an example of bony cavity that can be treated using catheter 3000. FIG. 31B shows a patient with a fractured bony cavity e.g. a fractured Maxillary sinus MS having one or more fractured bones 3024. In FIG. 31C, catheter 3000 is introduced into the Maxillary sinus MS through a natural opening e.g. an ostium or an artificially created opening. In FIG. 31D, one or more balloons on catheter 3000 are sequentially inflated to push fractured bones 3024 into their original un-fractured configuration. Catheter 3000 may then be left in place for a desired period ranging from a few minutes to several days during which fractured bones 3024 begin to heal in their original un-fractured configuration. After catheter 3000 has been left in place for the desired period, catheter 3000 is removed by deflating the balloons and withdrawing catheter 3000 from the anatomy. Thus, catheter 3000 provides an internal cast for a fractured bony cavity. Various embodiments of catheter 3000 may be used for crating internal casts for fractured paranasal sinuses, lachrymal passages, Eustachian tubes, other structures in the ear, nose, throat, mouth etc.

Figure 32:
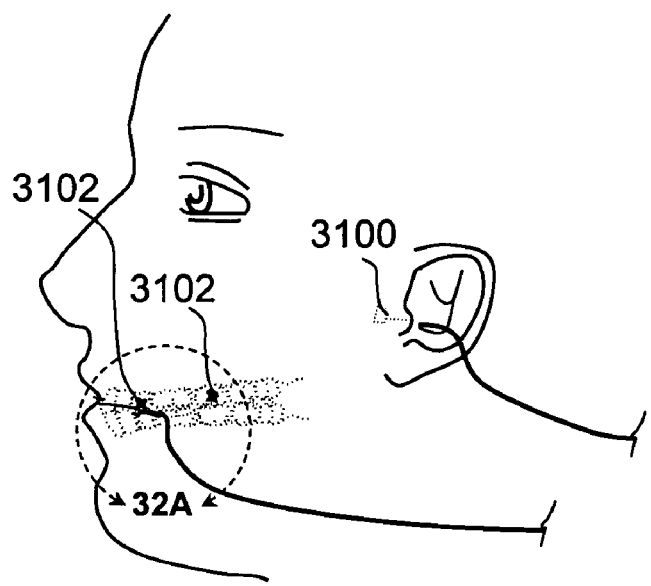
FIG. 32 shows an embodiment of a surgical navigation system comprising electromagnetic sensors.
Figure 32:
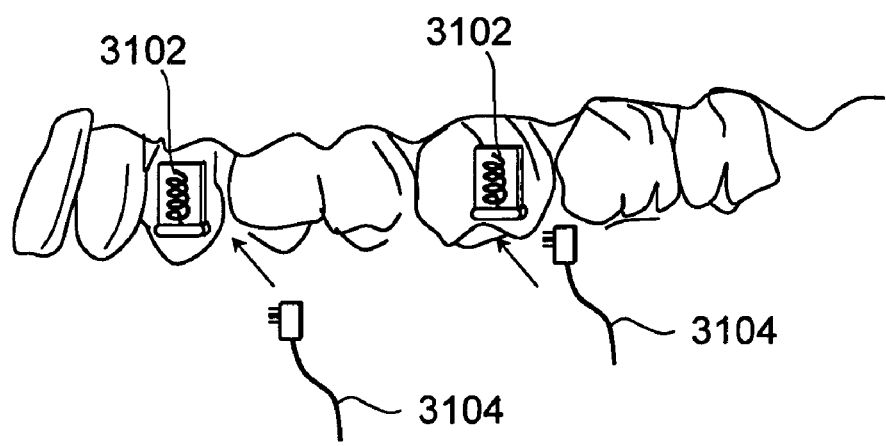

The various devices and methods disclosed herein may be used in conjunction with various surgical navigations systems. FIGS. 32 and 32A show an embodiment of a surgical navigation system comprising electromagnetic sensors. Examples of electromagnetic sensors that can be used with the present invention are electromagnetic sensors of an electromagnetic surgical navigation system such as GE InstaTrak™ 3500 plus system etc. FIG. 32 shows a perspective view of a patient's head showing the location of external ear canal electromagnetic sensors 3100 and teeth electromagnetic sensors 3102. External ear canal electromagnetic sensors 3100 are introduced through an ear canal into a region adjacent to a tympanum. Teeth electromagnetic sensors 3102 are attached to one or more teeth of the patient. In one embodiment, teeth electromagnetic sensors 3102 are attached to teeth using an adhesive. In an alternate embodiment, teeth electromagnetic sensors 3102 are attached to braces or caps which in turn are attached to teeth. The braces or caps can be made of suitable materials that cause minimal artifacts on CT or MRI images. An example of such a material is aluminum alloy 2017-T4 which causes minimal artifacts on a CT scan image. Other locations of electromagnetic sensors include skin (e.g. a skin patch comprising an electromagnetic sensor), a head frame etc. The patient's head is imaged using an imaging modality such as CT or MRI. External ear canal electromagnetic sensors 3100 and teeth electromagnetic sensors 3102 are passively imaged by the imaging modality and thus act as fiducial markers.

FIGS. 32 and 32A illustrate a surgical navigation system comprising fiducial markers that have electromagnetic sensors. Various other embodiments of fiducial markers such as passively imaged fiducial markers or active sensors or transmitters may be used in conjunction with the various methods and devices disclosed herein. The fiducial markers may be located on relevant anatomical regions such as teeth, ear canals, skull bones, frames fixed to rigid bones etc. The fiducial markers may be used with a variety of modalities including but not limited to electromagnetic, infrared, ultrasonic, radio-frequency, MRI, CT, Fluoroscopic or other 2D or 3D image guided systems for the head, neck or other anatomical regions manufactured by companies such as Biosense, Stryker, Brainlab, Xomed, GE/VTI etc.

FIG. 32A shows an enlarged view of region 32A in FIG. 32. Teeth electromagnetic sensors 3102 are connected to the electromagnetic surgical navigation system by removable leads 3104. In another embodiment, external ear canal electromagnetic sensors 3100 or teeth electromagnetic sensors 3102 are connected to the electromagnetic surgical navigation system by telemetry. During a procedure, external ear canal electromagnetic sensors 3100 and/or teeth electromagnetic sensors 3102 are actively imaged by suitable electromagnetic surgical navigation systems such as GE InstaTrak™ 3500 plus system etc. Thereafter, data from imaging modality such as CT or MRI and the electromagnetic surgical navigation system is merged to obtain a three dimensional map of the anatomy showing the electromagnetic sensors. The three dimensional map can then be used for image guided procedures such as diagnostic or therapeutic procedures of paranasal sinuses, Eustachian tubes, lachrymal ducts, other ear, nose, throat or mouth structures etc.

Other image guided surgery systems such as infrared sensor based systems e.g. Stryker Leibinger® Navigation System can also be used in conjunction with one or more methods or devices disclosed herein.

Figure 33:
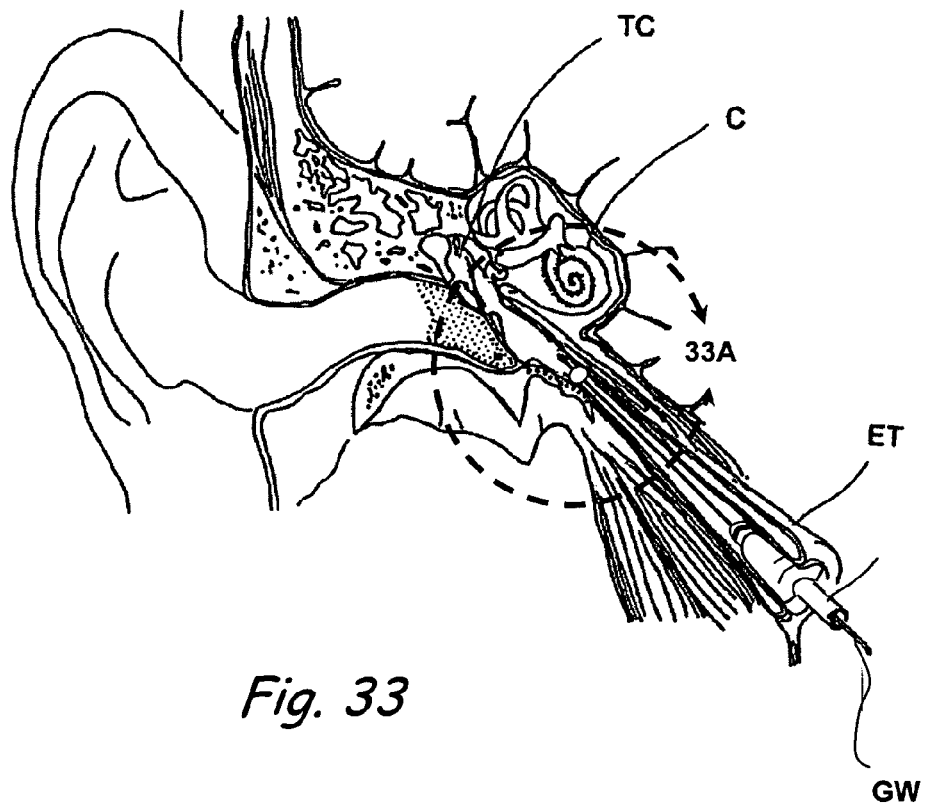
FIG. 33 shows a section of the anatomical region around a Eustachian tube (ET) showing a diagnostic or therapeutic procedure being performed by devices inserted through the pharyngeal ostium of the Eustachian tube.

FIG. 33 shows a section of the anatomical region around a Eustachian tube (ET) showing a diagnostic or therapeutic procedure being performed by devices inserted through the pharyngeal ostium of the Eustachian tube. FIG. 33 shows a guidewire GW inserted into a desired region in the ET through the Nasopharynx and a diagnostic or therapeutic being performed by a device introduced into the Eustachian tube over guidewire GW.

Figure 33A:
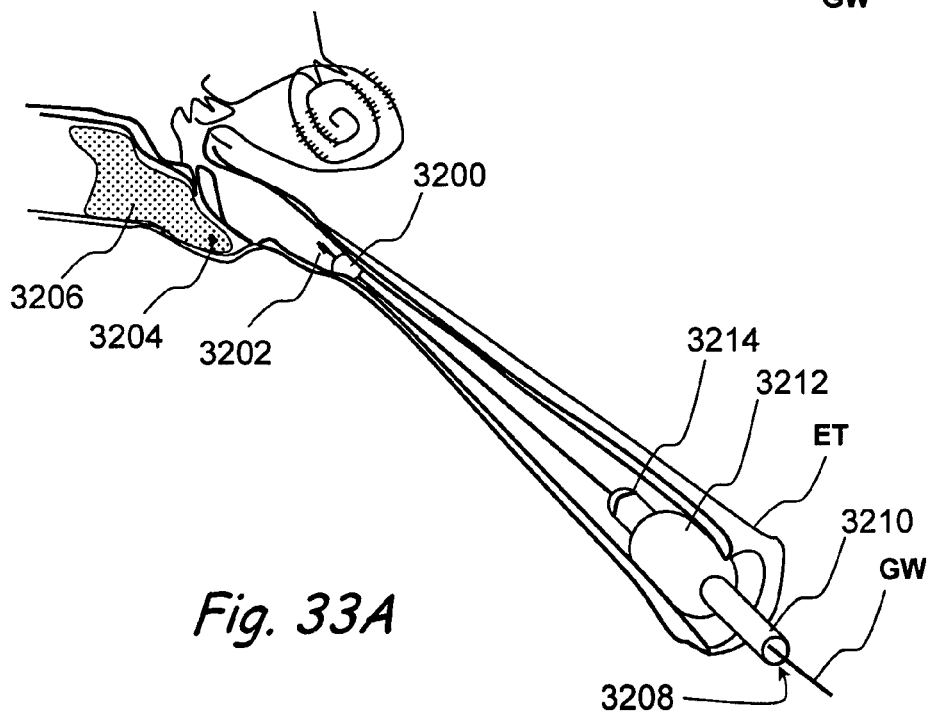
FIG. 33A shows an enlarged view of region 33A in FIG. 33.
Figure 33:
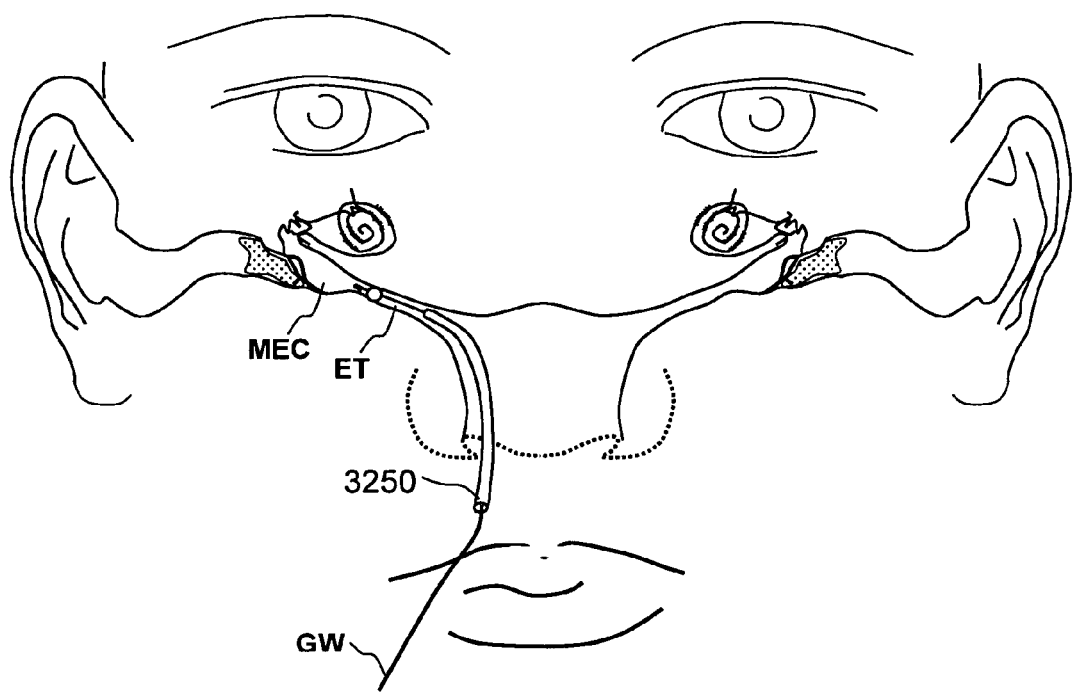

FIG. 33A shows an enlarged view of region 33A in FIG. 33 showing the anatomical region around a Eustachian tube (ET) showing a diagnostic or therapeutic procedure being performed by devices inserted through the pharyngeal ostium of the Eustachian tube. In one embodiment, guidewire GW comprises an anchoring balloon 3200 located on the distal region of guidewire GW. Anchoring balloon 3200 is inflated after positioning guidewire GW at a target location. Anchoring balloon 3200 anchors guidewire GW to the adjacent anatomy and prevents accidental repositioning of guidewire GW during a diagnostic or therapeutic procedure. Anchoring balloon 3200 may be made from suitable compliant or semi-compliant material such as crosslinked polyethylene or other polyolefins, polyurethane, flexible polyvinylchloride, Nylon etc. Guidewire GW may comprise anchoring elements other than anchoring balloon 3200 such as a notch on guidewire GW, a bent region on guidewire GW, a self expanding element, a hook, a coiled element etc. In another embodiment, guidewire GW comprises a sensor 3202 located on the distal region of guidewire GW. Sensor 3202 enables guidewire GW to be used in conjunction with a suitable surgical navigation system. In one embodiment, sensor 3202 is an electromagnetic sensor used in conjunction with an electromagnetic surgical navigation system such as GE InstaTrak™ 3500 plus system etc. One or more sensor 3202 or other types of surgical navigation sensors or transmitters may also be located on other diagnostic or therapeutic devices disclosed herein. Sensor 3202 may be used in conjunction with a stationary sensor 3204 located in the external ear. The combination of sensor 3202 and stationary sensor 3204 enables guidewire GW to be accurately positioned in a target region. In an embodiment, a radioopaque plug 3206 is inserted from the external ear to a region adjacent to an eardrum. Radioopaque plug 3206 serves as a fiducial marker during preoperative scanning of the patient and thus enables a physician to accurately position a diagnostic or therapeutic device close to the eardrum. Other image guidance methods and devices can also be used in conjunction with diagnostic or therapeutic procedures disclosed herein. FIG. 33A also shows a diagnostic or therapeutic device 3208 comprising a shaft 3210 and a working element 3212 e.g. a dilating balloon being introduced over guidewire GW. Diagnostic or therapeutic device 3208 may comprise a radiopaque marker 3214.

FIG. 33B shows a front view of a human head with a portion of the face removed to show an embodiment of a method of introducing a guidewire into a Eustachian tube. In FIG. 33B, a guide catheter 3250 is introduced through a nostril into the Nasopharynx. Distal portion of guide catheter 3250 may comprise a bent or angled region. For example, such bent or angled region may form e an internal angle ranging from 45 degrees to 150 degrees. Guide catheter 3250 can be constructed using one of the various designs disclosed herein and in the patent documents incorporated herein by reference. Guide catheter 3250 is positioned in the Nasopharynx such that the distal tip of guide catheter 3250 is located near a nasopharyngeal opening of a Eustachian tube. Thereafter, a guidewire GW is introduced through guide catheter 3250 into the Eustachian tube. Guidewire GW can then be used to advance one or more diagnostic or therapeutic devices into the Eustachian tube to perform one or more diagnostic or therapeutic procedures.

Figure 34:
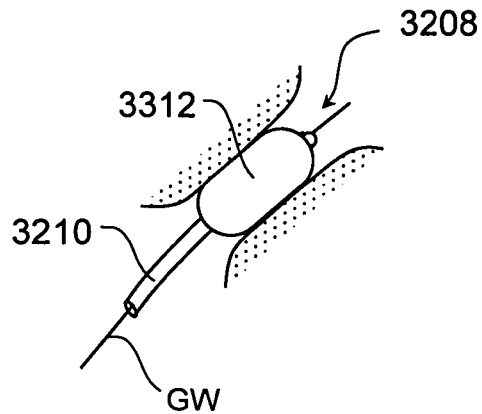
FIGS. 34A-34D illustrate various examples of working elements that could be located on the diagnostic or therapeutic device in FIG. 33.
Figure 34:
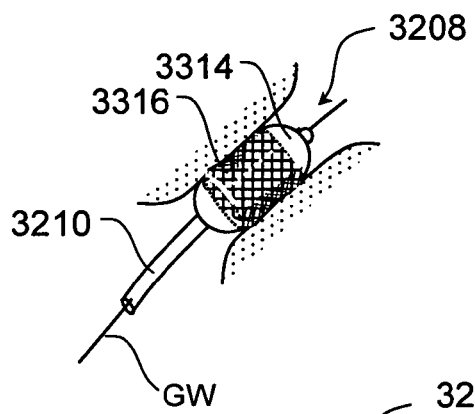
Figure 34:
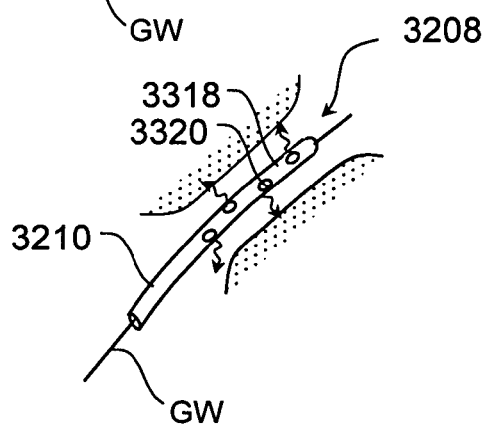
Figure 34:
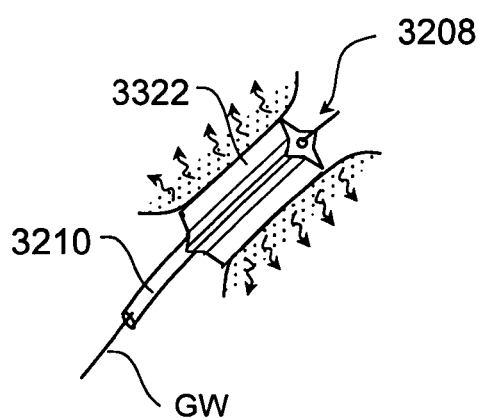

FIGS. 34A-34D illustrate various examples of working elements that can be located on the diagnostic or therapeutic device in FIG. 33. FIG. 34A shows an example of a working element comprising a dilating balloon. Dilating balloon 3312 can be made from a suitable non-compliant materials e.g. polyethylene terephthalate, Nylon etc. Similarly, devices shown in FIGS. 14, 15, 16, 17 and 18 may also be used to treat a Eustachian tube as shown in FIG. 33.

FIG. 34B shows an example of a working element comprising a dilating balloon loaded with a balloon-expandable stent. Dilating balloon 3314 can be made from a suitable non-compliant materials e.g. polyethylene terephthalate, Nylon etc. Several types of stent designs can be used to construct stent 3316 such as metallic tube designs, polymeric tube designs, chain-linked designs, spiral designs, rolled sheet designs, single wire designs etc. These designs may have an open celled or closed celled structure. A variety of fabrication methods can be used for fabricating stent 3316 including but not limited to laser cutting a metal or polymer element, welding metal elements etc. A variety of materials can be used for fabricating stent 3316 including but not limited to metals, polymers, foam type materials, plastically deformable materials, super elastic materials etc. A variety of features can be added to stent 3316 including but not limited to radiopaque coatings, drug elution mechanisms to elute anti-inflammatory agents, antibiotics etc. In one embodiment, stent 3316 is bioabsorbable. Working elements may also comprise a self-expanding stent instead of a pressure-expandable stent.

FIG. 34C shows an example of a working element comprising a lavage element. Lavage element 3318 comprises a plurality of lavage openings 3320. Lavage openings are connected to a lavage lumen in shaft 3210 through which suitable lavage media such as solutions containing contrast agents, pharmaceutically acceptable salt or dosage form of an anti-microbial agent (e.g., antibiotic, antiviral, anti-parasitic, anti-fungal, etc.), an anesthetic agent with or without a vasoconstriction agents (e.g. Xylocaine with or without Epinephrine, Tetracaine with or without epinephrine, etc.), an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an anti-histamine, cytokine inhibitor, leucotriene inhibitor, IgE inhibitor, immunomodulator), an allergen or another substance that causes secretion of mucous by tissues, hemostatic agents to stop bleeding, anti-proliferative agents, cytotoxic agents e.g. alcohol, biological agents such as protein molecules, stem cells, genes or gene therapy preparations etc. can be delivered. In one embodiment, a fraction of lavage openings 3320 are connected to an aspiration lumen to aspirate the lavage media out of the Eustachian tube.

FIG. 34D shows an example of a working element comprising a substance delivery reservoir. Substance delivery reservoir 3322 may be fully or partially biodegradable or non-biodegradable. In one embodiment, substance delivery reservoir 3322 is made of a suitable biocompatible material such as hydrogel (e.g. collage hydrogel). In another embodiment, substance delivery reservoir 3322 comprises a porous matrix formed of a porous material such as a flexible or rigid polymer foam, cotton wadding, gauze, etc. Examples of biodegradable polymers that may be foamed or otherwise rendered porous include polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. Examples of non-biodegradable polymers that may be foamed or otherwise rendered porous include polyurethane, polycarbonate, silicone elastomers etc. Substance delivery reservoir 3322 may also include one or more embodiments disclosed in U.S. patent application Ser. No. 10/912,578 entitled "Implantable Device and Methods for Delivering Drugs and Other Substances to Treat Sinusitis and Other Disorders" filed on Aug. 4, 2004, the entire disclosure of which is expressly incorporated herein by reference. The substance delivery reservoir 3322 or any substance delivery devices described in this application may be used to deliver various types of therapeutic or diagnostic agents. The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or nan-fluid. For example, in some applications where it is desired to treat or prevent a microbial infection, the substance delivered may comprise pharmaceutically acceptable salt or dosage form of an antimicrobial agent (e.g., antibiotic, antiviral, antiparacytic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc.

Some nonlimiting examples of antimicrobial agents that may be used in this invention include acyclovir, amantadine, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin (e.g., Bactroban Nasal®, Glaxo SmithKline, Research Triangle Park, N.C.), nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform); non-pathogenic or "friendly" microbes that cause the production of hydrogen peroxide or other substances that kill or inhibit the growth of pathogenic microbes (e.g., lactobacillus); antimicrobial proteins or peptides such as those described in U.S. Pat. No. 6,716,813 (Lin et al,.) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal administration may be used, such as beclomethasone (Vancenase® or Beconase®), flunisolide (Nasalide®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide) Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitoers such as an agent designated as "R-112" manufactured by Rigel Pharmaceuticals, Inc, or South San Francisco, Calif.

Additionally or alternatively, in some applications, such as those where it is desired to shrink mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine (Mucomyst™, Mucosil™) and guaifenesin.

In one particular embodiment, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chrom®) and nedocromil.

Additionally or alternatively, in some applications such as those where it is desired to prevent or inhibit the effect of histamine, the substances delivered in this invention may include various antihistamines such as azelastine (e.g., Astylin®), diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin/EDTA, hyaluronidase, and tosyllysylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anti-cholinergic agents that tend to dry up nasal secretions such as ipratropium (Atrovent Nasal®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include anti-tumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201(Aug. 17, 2000) which is expressly incorporated herein by reference, biological response modifiers (e.g., interferon, *bacillus* calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

Additionally or alternatively to being combined with a device and/or a substance releasing modality, it may be ideal to position the device in a specific location upstream in the mucous flow path (i.e. frontal sinus or ethmoid cells). This could allow the deposition of fewer drug releasing devices, and permit the "bathing" of all the downstream tissues with the desired drug. This utilization of mucous as a carrier for the drug may be ideal, especially since the concentrations for the drug may be highest in regions where the mucous is retained; whereas non-diseased regions with good mucous flow will be less affected by the drug. This could be particularly useful in chronic sinusitis, or tumors where bringing the concentration of drug higher at those specific sites may have greater therapeutic benefit. In all such cases, local delivery will permit these drugs to have much less systemic impact. Further, it may be ideal to configure the composition of the drug or delivery system such that it maintains a loose affinity to the mucous permitting it to distribute evenly in the flow. Also, in some applications, rather than a drug, a solute such as a salt or other mucous soluble material may be positioned at a location whereby mucous will contact the substance and a quantity of the substance will become dissolved in the mucous thereby changing some property (e.g., pH, osmolarity, etc) of the mucous. In some cases, this technique may be used to render the mucous hyperosmolar so that the flowing mucous will draw water and/or other fluid from polyps, edematous mucosal tissue, etc., thereby providing a drying or desiccating therapeutic effect.

Additionally or alternatively to substances directed towards local delivery to affect changes within the sinus cavity, the nasal cavities provide unique access to the olfactory system and thus the brain. Any of the devices and methods described herein may also be used to deliver substances to the brain or alter the functioning of the olfactory system. Such examples include, the delivery of energy or the deposition of devices and/or substances and/or substance delivering implant(s) to occlude or alter olfactory perception, to suppress appetite or otherwise treat obesity, epilepsy (e.g., barbiturates such as phenobarbital or mephoobarbital; iminostilbenes such as carbamazepine and oxcarbazepine; succinimides such as ethylsuximide; valproic acid; benzodiazepines such as clonazepam, clorazepate, diazepam and lorazepam, gabapentin, lamotrigine, acetazolamide, felbamate, levetiraceam, tiagabine, topiramate, zonisamide, etc.), personality or mental disorders (e.g., antidepressants, anti-anxiety agents, antipsychotics, etc.), chronic pain, Parkinson's disease (e.g., dopamine receptor agonists such as bromocriptine, pergolide, ropinitrol and pramipexole; dopamine precursors such as levodopa; COMT inhibitors such as tolcapone and entacapone; selegiline; muscarinic receptor antagonists such as trihexyphenidyl, benztropine and diphenhydramine) and Alzheimer's disease, Huntington's disease or other dementias, disorders of cognition or chronic degenerative diseases (e.g. tacrine, donepezil, rivastigmine, galantamine, fluoxetine, carbamazepine, clozapine, clonazepam and proteins or genetic therapies that inhibit the formation of beta-amyloid plaques), etc.

The working element need not necessarily be a substance delivery reservoir 3322. For example, another type of working element useable in this invention is a laser device. In one embodiment, the laser device may comprise an optical fiber that delivers laser energy through the distal region of the optical fiber. Typical examples of lasers that can be used in the present invention are Nd:YAG lasers, Ho:NAG lasers, short pulsed laser systems such as excimer lasers (wavelength: 308 nm, pulse length full width at half maximum height: 60 ns), dye lasers (wavelength: 504 nm, pulse length full width at half maximum height: 1200 ns), tunable die lasers, KTP lasers, argon lasers, Alexandrite lasers (wavelength: 755 nm, pulse length full width at half maximum height: 300-500 ns) etc. Such a laser device may also be used in conjunction with or as a part of any method, system or device disclosed in this patent application for laser-assisted ablation or cutting, laser-assisted cauterization or other laser-assisted methods of treating sinusitis, mucocysts, tumors, polyps, occlusions, obstructions, edema or other conditions of the paranasal sinuses, Eustachian tubes, Lachrymal ducts, salivary glands and other hard or soft ear, nose, throat or mouth structures.

Such devices, systems and methods may also be used for performing other diagnostic or therapeutic procedures of Eustachian tubes, tympanums and middle ear structures. Examples of such procedures are biopsies, microendoscopy of the Eustachian tube and the middle ear structures, diagnosis and/or treatment of roundwindow ruptures, auditory-ossicle dislocations after tympanoplasty, prothesis dislocation after stapeclotomy, neuroradiologically undetectable liquorrhea caused by otobasal fractures, progressive disorders of the sound-conducting apparatus, Dysplasia of the ear, chronic otitis media mesotympanalis, cholesteatoma, presurgical evaluation of pathologic findings of both the mucosal lining and the ossicular chain, epitympanic retraction pockets of the ear drum, all chronic and recurrent ventilation or drainage disorders of Eustachian tubes etc.

Figure 35:
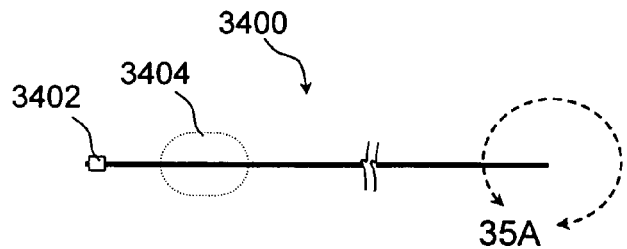
FIG. 35 shows a perspective view of an embodiment of a guidewire comprising a sensor used for surgical navigation.
Figure 35:
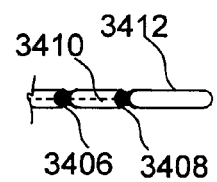
Figure 35:
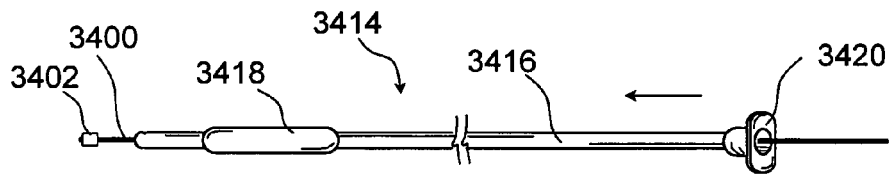
Figure 35:
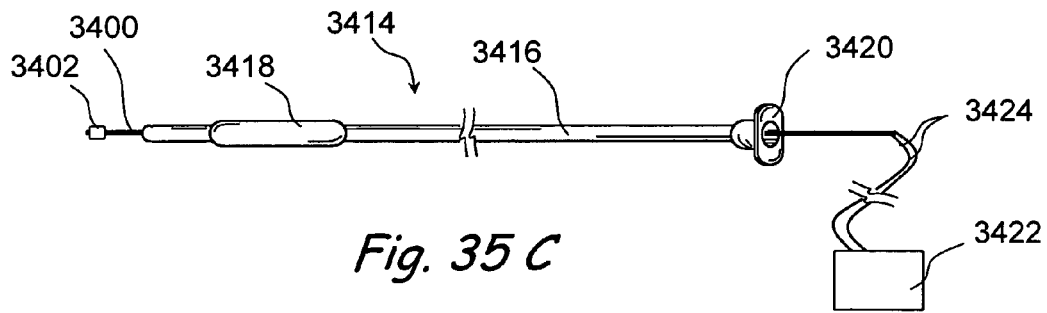
Figure 35:
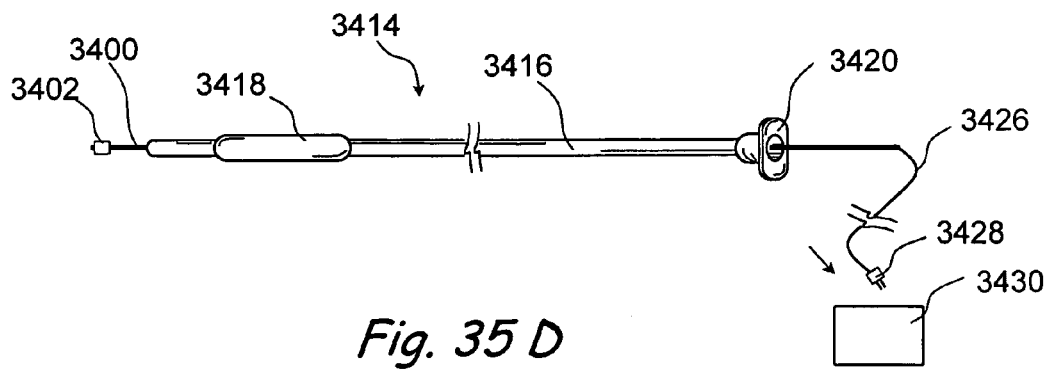

FIG. 35 shows a perspective view of an embodiment of a guidewire comprising a sensor used for surgical navigation. Guidewire 3400 comprises a sensor 3402 located on the distal region of guidewire 3400. Sensor 3402 enables guidewire 3400 to be used in conjunction with a suitable surgical navigation system. In one embodiment, sensor 3402 is an electromagnetic sensor used in conjunction with an electromagnetic surgical navigation system such as GE InstaTrak™ 3500 plus system. In one embodiment, guidewire 3400 comprises an anchoring balloon 3404 located on the distal region of guidewire 3400. Anchoring balloon 3404 is inflated after positioning guidewire 3400 at a target location. Anchoring balloon 3404 anchors guidewire 3400 to adjacent anatomy and prevents accidental repositioning of guidewire 3400 during a diagnostic or therapeutic procedure. Anchoring balloon 3404 may be made from suitable compliant or semi-compliant material such as crosslinked polyethylene or other polyolefins, polyurethane, flexible polyvinylchloride, Nylon etc. In one embodiment, guidewire 3400 comprises a soft distal tip. In another embodiment, guidewire 3400 comprises a curved distal end e.g. a "J" shaped distal end. Sensors similar to sensor 3402 may be present on other diagnostic or therapeutic devices disclosed herein such as balloon catheters etc. Similarly, the devices disclosed herein may comprise other types of sensors or transmitters such as electromagnetic, RF, piezoelectric, magnetic etc. The sensors or transmitters may be in the form of a variety of configurations including but not limited to single coils, multiple coils, antennae etc. The sensors or transmitters may be oriented in a variety of configurations including but not limited to nested, paired, orthogonal to each other, etc.

FIG. 35A shows an enlarged view of an embodiment of a low profile proximal region of the guidewire in FIG. 35. The proximal region of guidewire 3400 comprises a distal electrical contact 3406 and a proximal electrical contact 3408. Distal electrical contact 3406 and proximal electrical contact 3408 are connected to sensor 3402 by conducting wires that run along guidewire 3400 to provide electrical energy to sensor 3402. Distal electrical contact 3406 and proximal electrical contact 3408 are connected to an external electrical supply by detachable electrodes. Distal electrical contact 3406 and proximal electrical contact 3408 can be made of suitable conducting materials such as stainless steel, silver-palladium alloys, silver-platinum alloys etc. Distal electrical contact 3406 and proximal electrical contact 3408 are separated from each other by a first insulating element 3410. In one embodiment, guidewire 3400 further comprises a second insulating element 3412 located on the proximal end of guidewire 3400. A low profile proximal region allows for the introduction of diagnostic or therapeutic devices over guidewire 3400.

FIG. 35B shows a perspective view of a method of advancing a diagnostic or therapeutic device over the guidewire in FIG. 35. In this example, the diagnostic or therapeutic device is a balloon catheter 3414 comprising a shaft 3416 having a balloon 3418 at the distal region of shaft 3416 and a hub 3420 at the proximal end of shaft 3416. Balloon catheter is advanced into a target anatomical region over the guidewire 3400. In this example, guidewire 3400 comprises a low profile proximal end so that devices can be introduced in an over-the-wire manner into a target anatomy.

FIG. 35C shows a perspective view of an embodiment of a combination of a guidewire comprising a sensor having a diagnostic or therapeutic device preloaded on the guidewire. In this example, the diagnostic or therapeutic device is balloon catheter 3414. The proximal end of guidewire 3400 is connected to an external electrical supply 3422 by conducting wires 3424. In this example, guidewire 3400 does not have a low profile proximal end so that devices cannot be introduced in an over-the-wire manner into a target anatomy. Thus, balloon catheter 3414 is preloaded on guidewire 3400 by inserting proximal end of balloon catheter 3414 over distal end of guidewire 3400.

FIG. 35D shows a perspective view of a second embodiment of a combination of a guidewire comprising a sensor having a diagnostic or therapeutic device preloaded on the guidewire. In this example, the diagnostic or therapeutic device is balloon catheter 3414. The proximal end of guidewire 3400 is connected by conducting wires 3426 to plug 3428. Plug 3428 detachably fits into an external power supply 3430. In this example, guidewire 3400 does not have a low profile proximal end so that devices cannot be introduced in an over-the-wire manner into a target anatomy. Thus, balloon catheter 3414 is preloaded on guidewire 3400 by inserting proximal end of balloon catheter 3414 over distal end of guidewire 3400.

One or more flexible regions especially flexible distal regions on the diagnostic or therapeutic devices disclosed herein may comprise bending or deflecting elements. Examples of such bending or deflecting elements are one or more pull wires etc. made of suitable materials such as stainless steel flat wire etc. The abovementioned devices and methods may also be used for diagnosing or treating other conditions caused by narrowing or blockage of structures in the ear, nose, throat or mouth such as choanal atresia.

Various devices described herein such as catheters may comprise one or more lumens such as end-to-end lumens, zipper lumens, rapid exchange lumens, parallel lumen surrounded by a jacket etc.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method for enlarging a natural paranasal sinus ostium that has not previously been surgically altered, said method comprising the steps of:
    A) inserting and advancing an elongate guide having a present shape, a distal end and a lumen through a nostril of a subject to a position within or near the natural paranasal sinus ostium;
    B) advancing a dilator through the lumen of the elongate guide and positioning the dilator and guide such that the dilator is located beyond the distal end of the guide and within the natural paranasal sinus ostium; and
    C) using the dilator to dilate the natural paranasal sinus ostium causing breakage or rearrangement of bone that underlines the mucosa of the natural paranasal sinus ostium.

2. A method according to claim 1 wherein the guide has a curve and wherein Step B comprises advancing the dilator through the lumen of the guide and around the curve.

3. A method according to claim 2 wherein at least a portion of the guide catheter is malleable and wherein the method further comprises the step of:
    shaping a malleable portion of the guide catheter.

4. A method according to claim 1 wherein the dilator comprises a balloon catheter, and wherein Step B comprises advancing the balloon catheter through the lumen of the guide and positing the dilator and guide such that a balloon of the balloon catheter is positioned within the ostium.

5. A method according to claim 4 wherein at least a portion of the guide is malleable and wherein the method further comprises shaping a malleable portion of the guide.

6. A method according to claim 5 wherein the guide comprises a flexible guide catheter and a malleable outer tube through which the dilator extends.

7. A method according to claim 6 wherein the method further comprises the step of:
    shaping the malleable outer tube.

8. A method according to claim 1 wherein Step A comprises:
    inserting the elongate guide to a first position; and
    advancing a guidewire through the lumen of the elongate guide such that the guidewire extends into or through the ostium;
    and wherein Step B further comprises;
    advancing a dilator over the guidewire to a position where the dilator is positioned within the natural paranasal sinus ostium.

9. A method according to claim 8 further comprising the steps of:
    removing the dilator; and
    advancing a tubular sheath over the guidewire.

10. A method according to claim 9 further comprising the step of:
    removing the guidewire leaving the tubular sheath in place.

11. A method according to claim 10 further comprising the step of infusing or aspirating matter through said tubular sheath.

12. A method according to claim 10 further comprising the step of inserting a different guidewire through the tubular sheath.

13. A method according to claim 8 wherein
    the elongate guide is inserted to a first position;
    a tubular sheath having a lumen and a curved portion is inserted through the lumen of the elongate guide to a position where the curved portion of the tubular sheath extends out of the distal end of the elongate guide; and
    the guidewire is advanced through the lumen of the curved tubular sheath such that the guidewire extends into or through the ostium.

14. A method according to claim 1 wherein the dilator comprises a balloon that is positionable in the ostium and expandable therein to dilate the ostium.

15. A method according to claim 1 wherein the dilator comprises i) a catheter shaft having a distal end, said catheter shaft being advancable, distal end first, through the ostium and into the paranasal sinus, ii) an intrasinus balloon on a portion of the catheter shaft that becomes inserted within the paranasal sinus, said intrasinus balloon having a proximal end, the proximal end of the intrasinus balloon having an indented central portion surrounded by a peripheral portion and iii) a dilator located proximal to the intrasinus balloon, said dilator being useable to dilate the ostium, and, wherein the method further comprises:

advancing the dilation catheter to a position where the intrasinus balloon is within the paranasal sinus;

inflating the intrasinus balloon; and pulling the dilation catheter in the proximal direction until the peripheral portion of the proximal surface of the intrasinus balloon is in contact with the inner surface of the paranasal sinus adjacent to the ostium to dilate the ostium.

16. A method according to claim 1 wherein the dilator comprises: i) a catheter shaft, ii) a balloon attached to the catheter shaft, said balloon having an outer surface and iii) at least one substance reservoir on the outer surface of the balloon, said substance reservoir comprising a porous matrix in which a therapeutic or diagnostic substance is disposed, and, wherein the method further comprises inflating the balloon to dilate the ostium and compress the at least one substance reservoir against osteal tissue such that a therapeutically or diagnostically effective amount of the substance contacts the tissue.

17. A method according to claim 16 wherein a plurality of substance reservoirs are disposed circumferentially about the outer surface of the balloon.

18. A method according to claim 16 wherein the at least one substance reservoir comprises a coating on the outer surface of the balloon.

19. A method according to claim 1 wherein the dilator comprises i) a catheter shaft, ii) a non-compliant inner balloon attached to said catheter shaft and iii) a compliant outer balloon attached to said catheter shaft and surrounding said inner balloon, and, wherein the method further comprises:

inflating the compliant outer balloon and moving the dilator as necessary to position the inflated compliant outer balloon in the ostium such that the ostium creates an indentation in the compliant outer balloon; and inflating the noncompliant inner balloon to dilate the ostium.

20. A method according to claim 19 wherein the outer balloon is radiopaque and the method further comprises using radiographic imaging to observe the indentation in the compliant balloon created by the ostium.

21. A method according to claim 19 wherein the method further comprises inflating the compliant outer balloon with a radiopaque fluid to facilitate radiographic visualization of the indentation in the compliant balloon created by the ostium.

* * * * *

UNITED STATES PATENT AND TRADEMARK OFFICE
CERTIFICATE OF CORRECTION

PATENT NO. : 7,462,175 B2
APPLICATION NO. : 11/037548
DATED : December 9, 2008
INVENTOR(S) : Chang et al.

It is certified that error appears in the above-identified patent and that said Letters Patent is hereby corrected as shown below:

Col 43 line 61, delete "present" and substitute therefore --preset--

Signed and Sealed this

Twenty-second Day of December, 2009

David J. Kappos
*Director of the United States Patent and Trademark Office*